(12) United States Patent
Park et al.

(10) Patent No.: US 9,567,287 B2
(45) Date of Patent: Feb. 14, 2017

(54) COMPOUND FOR ORGANIC LIGHT-EMITTING DIODE AND ORGANIC LIGHT-EMITTING DIODE INCLUDING THE SAME

(71) Applicant: Samsung Display Co. Ltd., Yongin-si, Gyeonggi-do (KR)

(72) Inventors: Jun-Ha Park, Yongin-si (KR); Seok-Hwan Hwang, Yongin-si (KR); Young-Kook Kim, Yongin-si (KR); Hye-Jin Jung, Yongin-si (KR); Eun-Young Lee, Yongin-si (KR); Jin-O Lim, Yongin-si (KR); Sang-Hyun Han, Yongin-si (KR); Eun-Jae Jeong, Yongin-si (KR); Soo-Yon Kim, Yongin-si (KR); Se-Jin Cho, Yongin-si (KR); Jong-Hyuk Lee, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 821 days.

(21) Appl. No.: 13/633,850

(22) Filed: Oct. 2, 2012

(65) Prior Publication Data

US 2013/0270524 A1    Oct. 17, 2013

(30) Foreign Application Priority Data

Apr. 17, 2012 (KR) .................. 10-2012-0039968

(51) Int. Cl.
*H01L 51/54* (2006.01)
*C09K 11/06* (2006.01)
(Continued)

(52) U.S. Cl.
CPC ........... *C07C 211/61* (2013.01); *C07C 255/58* (2013.01); *C07D 209/86* (2013.01); *C07D 209/88* (2013.01);
(Continued)

(58) Field of Classification Search
CPC ........... C07D 209/00; C07D 209/8688; C07D 213/00; C07D 213/36; C07D 213/38; C07D 251/00; C07D 251/02; C07D 251/08; C07D 251/10; C07D 251/12; C07D 251/22; C07D 251/24; C07D 277/00; C07D 277/60; C07D 277/62; C07D 277/64; C07D 277/66; C07D 401/00; C07D 401/02; C07D 401/04; C07D 401/10; C07D 401/12; C07D 401/14; C07D 403/00; C07D 403/02; C07D 403/04; C07D 403/10; C07D 403/12; C07D 403/14; C07D 413/00; C07D 413/02; C07D 413/04; C07D 413/10; C07D 413/12; C07D 413/14; C07D 487/00; C07D 487/02; C07D 487/04; C07D 491/00; C07D 491/02; C07D 491/04; C07D 491/16; C07D 471/00; C07D 471/02; C07D 471/04; C07C 211/00; C07C 211/43; C07C 211/57; C07C 211/61; C07C 251/00; C07C 251/24; C07C 2103/00; C07C 2103/02; C07C 2103/04; C07C 2103/06; C07C 2103/10; C07C 2103/12; C07C 2103/18; C07C 2103/22; C07C 2103/24; C07C 2103/26; C07C 2103/40; C07C 2103/48; C07C 2103/50; C07C 2103/52; C07C 2103/54; C07B 2200/05; C09K 11/06; C09K 2211/00; C09K 2211/10; C09K 2211/1003; C09K 2211/1007; C09K 2211/1011; C09K 2211/1014; C09K 2211/1029; C09K 2211/1088; H01L 51/0032; H01L 51/005; H01L 51/0051; H01L 51/0059; H01L 51/006; H01L 51/0061; H01L 51/0072; H01L 51/50; H01L 51/5012; H01L 51/5016; H01L 51/5048; H01L 51/5052; H01L 51/5056; H01L 51/506; H01L 51/5088

(Continued)

(56) References Cited

U.S. PATENT DOCUMENTS

| 4,356,429 A | 10/1982 | Tang |
| 4,885,211 A | 12/1989 | Tang et al. |

(Continued)

FOREIGN PATENT DOCUMENTS

| JP | 05-234681 | 9/1993 |
| JP | 8-12600 | 1/1996 |

(Continued)

OTHER PUBLICATIONS

Machine translation of KR2009-0029893. Date of publication: Mar. 24, 2009.*

(Continued)

*Primary Examiner* — Andrew K Bohaty
(74) *Attorney, Agent, or Firm* — Lewis Roca Rothgerber Christie LLP

(57) ABSTRACT

A compound represented by Formula 1 below may be used in an organic light emitting diode. Additionally, in some embodiments, an organic light-emitting diode includes a first electrode, a second electrode, and an organic layer between the first electrode and the second electrode and including the compound represented by Formula 1.

(Continued)

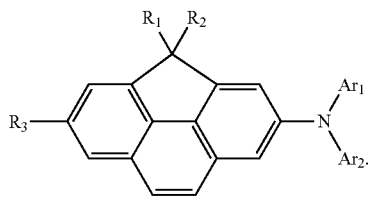

Formula 1

18 Claims, 1 Drawing Sheet

(51) Int. Cl.

| | | |
|---|---|---|
| C07C 211/61 | (2006.01) | |
| C07C 255/58 | (2006.01) | |
| C07D 251/24 | (2006.01) | |
| C07D 471/04 | (2006.01) | |
| C07D 209/86 | (2006.01) | |
| C07D 209/88 | (2006.01) | |
| C07D 213/38 | (2006.01) | |
| C07D 403/12 | (2006.01) | |
| C07D 401/14 | (2006.01) | |
| C07D 401/04 | (2006.01) | |
| C07D 235/06 | (2006.01) | |
| C07D 401/12 | (2006.01) | |
| C07D 403/04 | (2006.01) | |
| C07D 403/10 | (2006.01) | |
| C07D 403/14 | (2006.01) | |
| C07D 413/04 | (2006.01) | |
| C07D 487/04 | (2006.01) | |
| C07D 491/16 | (2006.01) | |
| C07D 277/66 | (2006.01) | |
| H01L 51/00 | (2006.01) | |
| H05B 33/10 | (2006.01) | |
| H01L 51/50 | (2006.01) | |

(52) U.S. Cl.
CPC ........... *C07D 213/38* (2013.01); *C07D 235/06* (2013.01); *C07D 251/24* (2013.01); *C07D 277/66* (2013.01); *C07D 401/04* (2013.01); *C07D 401/12* (2013.01); *C07D 401/14* (2013.01); *C07D 403/04* (2013.01); *C07D 403/10* (2013.01); *C07D 403/12* (2013.01); *C07D 403/14* (2013.01); *C07D 413/04* (2013.01); *C07D 471/04* (2013.01); *C07D 487/04* (2013.01); *C07D 491/16* (2013.01); *C09K 11/06* (2013.01); *H01L 51/006* (2013.01); *H01L 51/0061* (2013.01); *H01L 51/0072* (2013.01); *H05B 33/10* (2013.01); *C07B 2200/05* (2013.01); *C07C 2103/18* (2013.01); *C07C 2103/24* (2013.01); *C07C 2103/26* (2013.01); *C07C 2103/40* (2013.01); *C07C 2103/50* (2013.01); *C07C 2103/54* (2013.01); *C07C 2103/94* (2013.01); *C09K 2211/1007* (2013.01); *C09K 2211/1011* (2013.01); *C09K 2211/1014* (2013.01); *C09K 2211/1029* (2013.01); *C09K 2211/1088* (2013.01); *H01L 51/5012* (2013.01); *H01L 51/5056* (2013.01)

(58) Field of Classification Search
USPC ....... 428/690, 691, 917, 411.4, 336; 427/58, 427/66; 313/500–512; 257/40, 88–104, 257/E51.001–E51.052; 252/301.16–301.35; 564/427; 558/418; 546/255, 87, 256; 548/442, 420; 549/43, 549/460; 544/180
See application file for complete search history.

(56) References Cited

U.S. PATENT DOCUMENTS

| | | | |
|---|---|---|---|
| 5,151,629 | A | 9/1992 | VanSlyke |
| 5,635,308 | A | 6/1997 | Inoue et al. |
| 5,972,247 | A | 10/1999 | Shi et al. |
| 6,242,115 | B1* | 6/2001 | Thomson .............. C07C 211/54 257/94 |
| 6,465,115 | B2 | 10/2002 | Shi et al. |
| 6,596,415 | B2 | 7/2003 | Shi et al. |
| 7,781,579 | B2 | 8/2010 | Park et al. |
| 7,833,635 | B2 | 11/2010 | Park et al. |
| 7,854,999 | B2 | 12/2010 | Park et al. |
| 7,875,367 | B2 | 1/2011 | Park et al. |
| 2001/0024738 | A1 | 9/2001 | Hawker et al. |
| 2004/0207318 | A1* | 10/2004 | Lee et al. ...................... 313/506 |
| 2005/0106418 | A1 | 5/2005 | Kim et al. |
| 2005/0139823 | A1* | 6/2005 | Hirakata et al. ................ 257/40 |
| 2005/0158583 | A1 | 7/2005 | Kim et al. |
| 2007/0290610 | A1* | 12/2007 | Park et al. .................... 313/504 |
| 2009/0092853 | A1* | 4/2009 | Park et al. .................... 428/690 |
| 2009/0200928 | A1* | 8/2009 | Hwang et al. ................ 313/504 |
| 2009/0284140 | A1 | 11/2009 | Osaka et al. |

FOREIGN PATENT DOCUMENTS

| | | |
|---|---|---|
| JP | 11-003782 | 1/1999 |
| JP | 11-135261 | 5/1999 |
| JP | 2000-3782 | 1/2000 |
| KR | 10-2007-0119470 | 12/2007 |
| KR | 10-2008-0030260 | 4/2008 |
| KR | 10-2008-0036483 | 4/2008 |
| KR | 10-2008-0039057 | 5/2008 |
| KR | 10-2008-0079095 | 8/2008 |
| KR | 20090029893 A * | 3/2009 |
| KR | 10-2010-0026373 A | 3/2010 |

OTHER PUBLICATIONS

U.S. Office action dated Apr. 6, 2011, for cross reference U.S. Appl. No. 12/076,776, (8 pages).
U.S. Office action dated Oct. 28, 2011, for cross reference U.S. Appl. No. 12/076,776, (9 pages).
U.S. Office action dated Jun. 29, 2012, for cross reference U.S. Appl. No. 12/076,776, (14 pages).
U.S. Office action dated Jul. 2, 2015, for cross reference U.S. Appl. No. 13/673,973, (24 pages).
Kuwabara, et al., *Thermally Stable Multilayered Organic Electroluminescent Devices Using Novel Starburst Molecules, 4,4',4"-Tri(N-carbazolyl)triphenylamine (TCTA) and 4,4', 4"-Tris (3-methylphenylphenyl-amino)triphenylarnine (m-MTDATA), as Hole-Transport Materials,* Advanced Materials, Sep. 1994, vol. 6, No. 9, pp. 677-679.
Patent Abstracts of Japan, and English machine translation of Japanese Publication 11-135261 dated May 21, 1999, (37 pages).

* cited by examiner

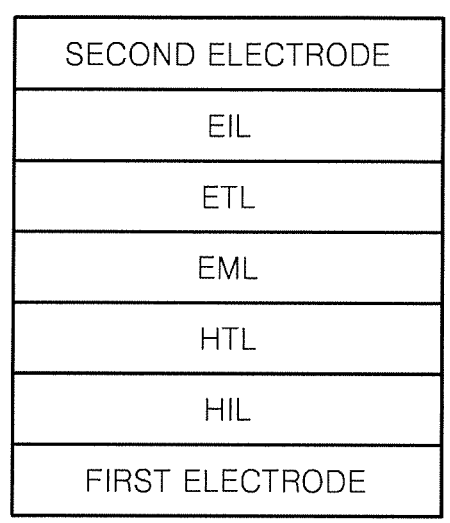

COMPOUND FOR ORGANIC LIGHT-EMITTING DIODE AND ORGANIC LIGHT-EMITTING DIODE INCLUDING THE SAME

CROSS-REFERENCE TO RELATED PATENT APPLICATION

This application claims priority to and the benefit of Korean Patent Application No. 10-2012-0039968, filed on Apr. 17, 2012 in the Korean Intellectual Property Office, the entire content of which is incorporated herein by reference.

BACKGROUND

1. Technical Field

One or more embodiments of the present invention relate to compounds for organic light-emitting devices and to organic light-emitting devices including the compounds.

2. Description of the Related Art

Organic light-emitting diodes (OLEDs) are self-emitting devices having advantages such as wide viewing angles, good contrast, quick response times, high brightness, and good driving voltage. OLEDs can provide multicolored images.

In general, an OLED has a structure including a substrate, an anode, a hole transport layer (HTL), an emission layer (EML), an electron transport layer (ETL), and a cathode, which are sequentially stacked on the substrate. In this regard, the HTL, the EML, and the ETL are organic thin films formed of organic compounds.

An operating principle of an OLED having the above-described structure is as follows.

When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

The most important factor for determining the luminous efficiency of an OLED is the light-emitting material. Fluorescent materials or phosphorescent materials have been used as the light-emitting material, but OLEDs including such light-emitting materials do not exhibit satisfactory efficiency, driving voltage and lifetime.

SUMMARY

Embodiments of the present invention provide novel compounds for an organic light-emitting diode which have good electrical properties, good charge transporting abilities, good luminous properties and high glass transition temperatures. The compounds are capable of preventing crystallization, and may be used as electron transporting materials suitable for use in fluorescent and phosphorescent devices of all colors, such as red, green, blue, white, and the like. The compounds may also be used as light-emitting materials of green, blue, or white color having higher luminous efficiency and longer lifetimes than those of conventional host materials. The compounds also have appropriate color coordinates.

Embodiments of the present invention also provide an organic light-emitting diode including the compound described above and having high efficiency, low voltage, high brightness, and long lifetime.

According to an aspect of the present invention, a compound for an organic light-emitting diode is represented by Formula 1 below:

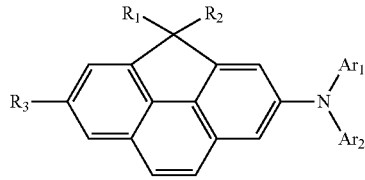

Formula 1

In Formula 1, $R_1$ and $R_2$ are each independently a halogen, a cyano group, a substituted or unsubstituted $C_1$-$C_{60}$ alkyl group, a substituted or unsubstituted $C_6$-$C_{60}$ aryl group, a substituted or unsubstituted $C_3$-$C_{60}$ heteroaryl group, or a substituted or unsubstituted $C_6$-$C_{60}$ condensed polycyclic group.

$R_3$ is hydrogen, deuterium, a halogen, a cyano group, a substituted or unsubstituted $C_6$-$C_{60}$ aryl group, a substituted or unsubstituted $C_3$-$C_{60}$ heteroaryl group, or a substituted or unsubstituted $C_6$-$C_{60}$ condensed polycyclic group.

$Ar_1$ and $Ar_2$ are each independently a substituted or unsubstituted $C_6$-$C_{60}$ aryl group, a substituted or unsubstituted $C_3$-$C_{60}$ heteroaryl group, or a substituted or unsubstituted $C_6$-$C_{60}$ condensed polycyclic group.

According to another aspect of the present invention, an organic light-emitting diode includes a first electrode; a second electrode; and an organic layer between the first electrode and the second electrode. The organic layer includes the compound of Formula 1.

According to another aspect of the present invention, a flat panel display device includes the organic light-emitting diode, and a first electrode of the organic light-emitting diode is electrically connected to a source electrode or a drain electrode of a thin film transistor.

BRIEF DESCRIPTION OF THE DRAWINGS

The above and other features and advantages of the present invention will become more apparent by reference to the following detailed description when considered in conjunction with the attached drawing in which:

FIG. 1 is a schematic diagram of a structure of an organic light-emitting diode according to an embodiment of the present invention.

DETAILED DESCRIPTION OF THE INVENTION

Hereinafter, exemplary embodiments of the present invention will be described. As used herein, the term "and/or" includes any and all combinations of one or more of the associated listed items. Expressions such as "at least one of," when preceding a list of elements, modify the entire list of elements and do not modify the individual elements of the list.

According to an embodiment of the present invention, a compound is represented by Formula 1 below:

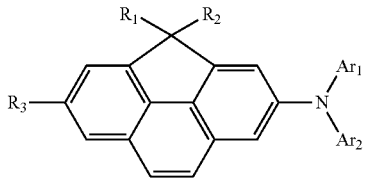

Formula 1

In Formula 1, $R_1$ and $R_2$ are each independently a halogen, a cyano group, a substituted or unsubstituted $C_1$-$C_{60}$ alkyl group, a substituted or unsubstituted $C_6$-$C_{60}$ aryl group, a substituted or unsubstituted $C_3$-$C_{60}$ heteroaryl group, or a substituted or unsubstituted $C_6$-$C_{60}$ condensed polycyclic group.

$R_3$ is hydrogen, deuterium, a halogen, a cyano group, a substituted or unsubstituted $C_6$-$C_{60}$ aryl group, a substituted or unsubstituted $C_3$-$C_{60}$ heteroaryl group, or a substituted or unsubstituted $C_6$-$C_{60}$ condensed polycyclic group.

$Ar_1$ and $Ar_2$ are each independently a substituted or unsubstituted $C_6$-$C_{60}$ aryl group, a substituted or unsubstituted $C_3$-$C_{60}$ heteroaryl group, or a substituted or unsubstituted $C_6$-$C_{60}$ condensed polycyclic group.

The compounds of Formula 1 have higher driving voltages and efficiency than conventional hole transporting materials. Thus, an OLED including a compound of Formula 1 exhibits good driving lifetime and increased power efficiency. Therefore, an OLED with low power consumption may be manufactured.

The compounds of Formula 1 have asymmetrical structures in which one amine group is substituted in a central fused aromatic ring, which leads to a relatively high Tg and an improved hole transporting ability.

In a symmetric structure in which two amine groups are substituted in the central fused aromatic ring, free rotation of amine bonds increases. Thus, compounds having a symmetric structure have relatively low Tgs as compared to the compounds of Formula 1 having an asymmetric structure. In addition, the symmetric structure increases the electron-donating properties of the amine groups, and thus makes the HOMO (highest occupied molecular orbital) energy level of the molecules unstable, resulting in an increased HOMO energy level. Therefore, when a compound having a symmetric structure is used as a material for forming the hole transport layer (HTL), there is a large difference in the HOMO energy level between the compound with the symmetric structure and a host. Accordingly, compounds having a symmetric structure may be used to form the hole injection layer (HIL) rather than the HTL.

The substituents of the compound of Formula 1 will now be described in more detail.

According to one embodiment, in Formula 1, $R_1$ and $R_2$ may be each independently a halogen, a cyano group, a substituted or unsubstituted $C_1$-$C_{30}$ alkyl group, a substituted or unsubstituted $C_6$-$C_{30}$ aryl group, a substituted or unsubstituted $C_3$-$C_{30}$ heteroaryl group, or a substituted or unsubstituted $C_6$-$C_{30}$ condensed polycyclic group. $R_3$ may be hydrogen, deuterium, a halogen, a cyano group, a substituted or unsubstituted $C_6$-$C_{30}$ aryl group, a substituted or unsubstituted $C_3$-$C_{30}$ heteroaryl group, or a substituted or unsubstituted $C_6$-$C_{30}$ condensed polycyclic group. $Ar_1$ and $Ar_2$ may be each independently a substituted or unsubstituted $C_6$-$C_{30}$ aryl group, a substituted or unsubstituted $C_3$-$C_{30}$ heteroaryl group, or a substituted or unsubstituted $C_6$-$C_{30}$ condensed polycyclic group.

According to another embodiment, in Formula 1, $R_1$ and $R_2$ may be each independently hydrogen, deuterium, a halogen, a cyano group, a substituted or unsubstituted $C_1$-$C_{20}$ alkyl group, or a moiety represented by any one of Formulae 2a through 2c below.

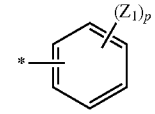

2a

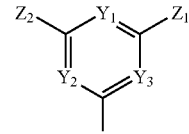

2b

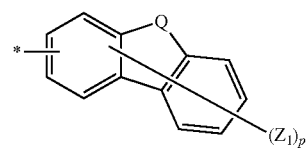

2c

In Formulae 2a through 2c, $Y_1$, $Y_2$, and $Y_3$ are each independently a linking group represented by —N=, —N($R_{20}$)—, or —C($R_{21}$)=.

Q is a linking group represented by —C($R_{30}$)($R_{31}$)—, —N($R_{32}$)—, —S—, or —O—.

$Z_1$, $Z_2$, $R_{20}$, $R_{21}$, $R_{30}$, $R_{31}$, and $R_{32}$ are each independently a hydrogen atom, deuterium, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, or an amino group that is substituted with a $C_6$-$C_{20}$ aryl group or a $C_3$-$C_{20}$ heteroaryl group, a halogen, a cyano group, a nitro group, a hydroxyl group, or a carboxyl group.

Also, p is an integer of 1 to 7, and * denotes a binding site.

In another embodiment, in Formula 1, $R_3$ may be hydrogen, deuterium, a halogen, or a moiety represented by any one of Formulae 3a through 3c below.

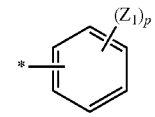

3a

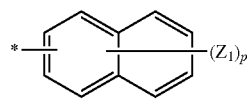

3b

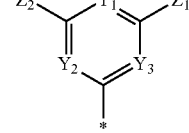

3c

In Formulae 3a through 3c, $Y_1$, $Y_2$, and $Y_3$ are each independently a linking group represented by —N=, —N($R_{20}$)—, or —C($R_{21}$)=.

$Z_1$, $Z_2$, $R_{20}$, and $R_{21}$ are each independently a hydrogen atom, deuterium, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, a halogen, a cyano group, a nitro group, a hydroxyl group, or a carboxyl group.

Also, p is an integer of 1 to 7, and * denotes a binding site.

In Formula 1, $Ar_1$ and $Ar_2$ may be any one of Formulae 4a through 4g below.

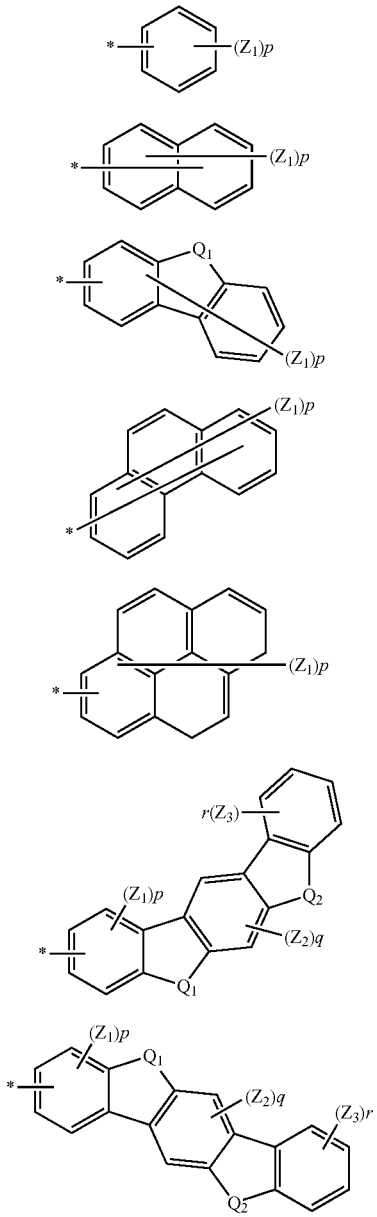

In Formulae 4a through 4g, $Q_1$ and $Q_2$ are each independently a linking group represented by —C($R_{30}$)($R_{31}$)—, —N($R_{32}$)—, —S—, or —O—.

$Z_1$, $Z_2$, $Z_3$, $R_{30}$, $R_{31}$, and $R_{32}$ are each independently a hydrogen atom, deuterium, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, an amino group that is substituted with a $C_6$-$C_{20}$ aryl group or a $C_3$-$C_{20}$ heteroaryl group, a substituted or unsubstituted $C_6$-$C_{20}$ condensed polycyclic group, a halogen, a cyano group, a nitro group, a hydroxyl group, or a carboxyl group.

Also, p is an integer of 1 to 9, q is 1 or 2, r is an integer of 1 to 4, and * denotes a binding site.

In Formula 1, $R_1$ and $R_2$ may be linked to each other to form a ring, or $Ar_1$ and $Ar_2$ may be linked to each to form a ring.

Hereinafter, representative groups of the substituents as used herein will be described. The number of carbon atoms that define the substituents is non-limiting, and do not limit the properties of the substituents.

The unsubstituted $C_1$-$C_{60}$ alkyl group is a linear or branched alkyl group. Nonlimiting examples of the unsubstituted $C_1$-$C_{60}$ alkyl group include methyl, ethyl, propyl, isobutyl, sec-butyl, pentyl, iso-amyl, hexyl, heptyl, octyl, nonanyl, dodecyl, and the like. To obtain the substituted alkyl group, at least one hydrogen atom of the unsubstituted $C_1$-$C_{60}$ alkyl group may be substituted with deuterium, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_4$-$C_{16}$ heteroaryl group.

The unsubstituted $C_2$-$C_{60}$ alkenyl group is group containing at least one carbon-carbon double bond in the center or at a terminal end of the unsubstituted $C_2$-$C_{60}$ alkyl group. Nonlimiting examples of the unsubstituted $C_2$-$C_{60}$ alkenyl group include ethenyl, propenyl, butenyl, and the like. To obtain the substituted alkenyl group, at least one hydrogen atom of the unsubstituted $C_2$-$C_{60}$ alkenyl group may be substituted with the substituents described above with respect to the substituted $C_1$-$C_{60}$ alkyl group.

The unsubstituted $C_2$-$C_{60}$ alkynyl group is a group containing at least one carbon-carbon triple bond in the center or at a terminal end of the $C_2$-$C_{60}$ alkyl group defined above. Nonlimiting examples of the unsubstituted $C_2$-$C_{60}$ alkynyl group include acetylene, propylene, phenylacetylene, naphthylacetylene, isopropylacetylene, t-butylacetylene, diphenylacetylene, and the like. To obtain the substituted alkynyl group, at least one hydrogen atom of the unsubstituted $C_2$-$C_{60}$ alkynyl group may be substituted with the substituents described above with respect to the substituted $C_1$-$C_{60}$ alkyl group.

The unsubstituted $C_3$-$C_{60}$ cycloalkyl group denotes a $C_3$-$C_{60}$ ring-type alkyl group. To obtain the substituted cycloalkyl group, at least one hydrogen atom of the unsubstituted $C_3$-$C_{60}$ cycloalkyl group may be substituted with the substituents described above with respect to the substituted $C_1$-$C_{60}$ alkyl group.

The unsubstituted $C_3$-$C_{60}$ alkoxy group has the Formula —OA in which A is the unsubstituted $C_1$-$C_{60}$ alkyl group. Nonlimiting examples of the $C_1$-$C_{60}$ alkoxy group include methoxy, ethoxy, propoxy, isopropyloxy, butoxy, pentoxy, and the like. To obtain the substituted alkoxy group, at least one hydrogen atom of the unsubstituted $C_1$-$C_{60}$ alkoxy group may be substituted with the substituents described above with respect to the substituted $C_1$-$C_{60}$ alkyl group.

The unsubstituted $C_6$-$C_{60}$ aryl group refers to a $C_6$-$C_{60}$ carbocyclic aromatic system containing at least one ring. When the aryl group contains at least two rings, the rings may be fused with each other or linked to each other by a single bond. The term "aryl" refers to an aromatic system, including, for example, phenyl, naphthyl, anthracenyl, and the like. To obtain the substituted aryl group, at least one hydrogen atom of the unsubstituted $C_6$-$C_{60}$ aryl group may be substituted with the substituents described above with respect to the substituted $C_1$-$C_{60}$ alkyl group.

Nonlimiting examples of the unsubstituted $C_6$-$C_{60}$ aryl group include a phenyl group, a $C_1$-$C_{10}$ alkylphenyl group (e.g., an ethylphenyl group), a halophenyl group (e.g., an o-, m- and p-fluorophenyl group, and a dichlorophenyl group), a cyanophenyl group, a dicyanophenyl group, a trifluoromethoxyphenyl group, a biphenyl group, a halobiphenyl group, a cyanobiphenyl group, a $C_1$-$C_{10}$ alkylbiphenyl group, a $C_1$-$C_{10}$ alkoxybiphenyl group, an o-, m-, and p-tolyl group, an o-, m- and p-cumenyl group, a mesityl group, a phenoxyphenyl group, an ($\alpha,\alpha$-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (e.g., a fluoronaphthyl group), a $C_1$-$C_{10}$ alkylnaphthyl group (e.g., a methylnaphthyl group), a $C_1$-$C_{10}$ alkoxynaphthyl group (e.g., a methoxynaphthyl group), a cyanonaphthyl group, an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl, a pyranthrenyl group, and an ovalenyl group.

The unsubstituted $C_3$-$C_{60}$ heteroaryl group indicates a group having 1, 2 or 3 hetero atom(s) selected from N, O, P, and S. When the $C_3$-$C_{60}$ heteroaryl group contains at least two rings, the rings may be fused with each other or linked to each other by a single bond. Nonlimiting examples of the unsubstituted $C_3$-$C_{60}$ heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, and a dibenzothiophene group. To obtain the substituted heteroaryl group, at least one hydrogen atom of the unsubstituted $C_3$-$C_{60}$ heteroaryl group may be substituted with the substituents described above with respect to the substituted $C_1$-$C_{60}$ alkyl group.

The unsubstituted $C_6$-$C_{60}$ aryloxy group has the formula —$OA_1$ in which $A_1$ is the $C_6$-$C_{60}$ aryl group as described above. Nonlimiting examples of the unsubstituted $C_6$-$C_{60}$ aryloxy group include a phenoxy group and the like. To obtain the substituted aryloxy group, at least one hydrogen atom of the unsubstituted $C_6$-$C_{60}$ aryloxy group may be substituted with the substituents described above with respect to the substituted $C_1$-$C_{60}$ alkyl group.

The unsubstituted $C_6$-$C_{60}$ arylthio group has the formula —$SA_1$ in which $A_1$ is the $C_6$-$C_{60}$ aryl group described above. Nonlimiting examples of the unsubstituted $C_6$-$C_{60}$ arylthio group include a benzenethio group, a naphthylthio group, or the like. To obtain the substituted arylthio group, at least one hydrogen atom of the unsubstituted $C_6$-$C_{60}$ arylthio group may be substituted with the substituents described above with respect to the substituted $C_1$-$C_{60}$ alkyl group.

The unsubstituted $C_6$-$C_{60}$ condensed polycyclic group indicates a substituent having at least two rings in which at least one aromatic ring and at least one non-aromatic ring are fused with each other, or a substituent having an unsaturated group but not having a conjugated system in the ring. The unsubstituted $C_6$-$C_{60}$ condensed polycyclic group differs from the aryl and heteroaryl groups in that it is overall non-aromatic.

In some embodiments, the compound of Formula 1 may be one of Compounds 1 through 51 below, but is not limited thereto.

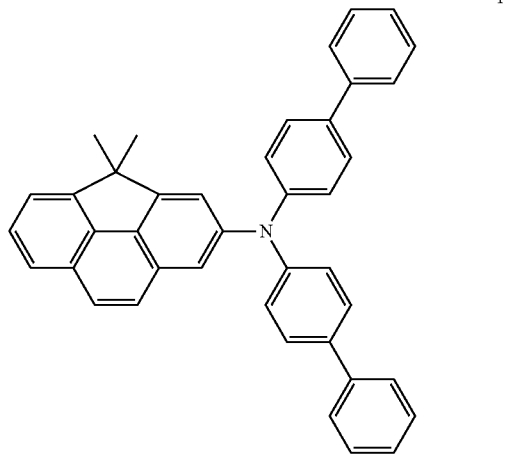

1

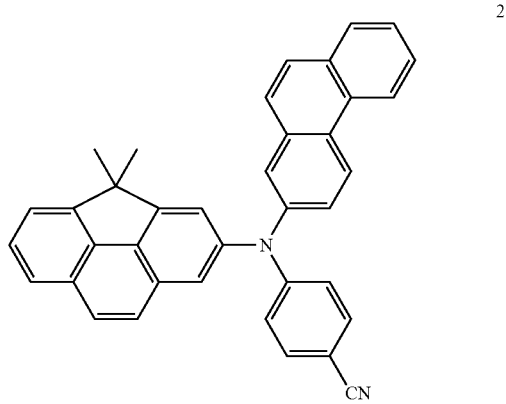

2

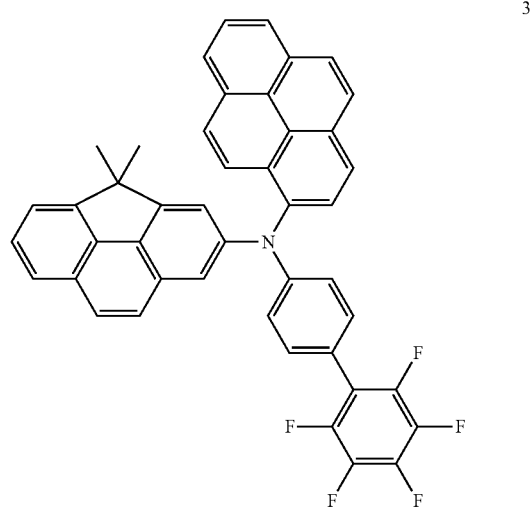

3

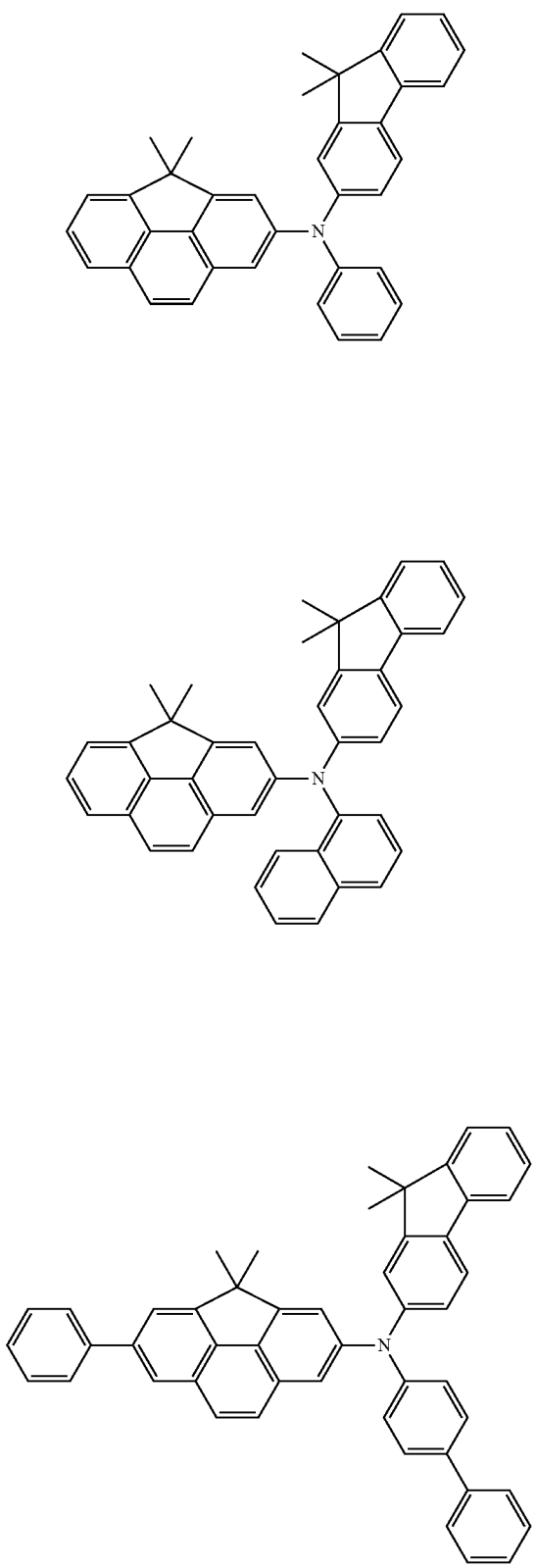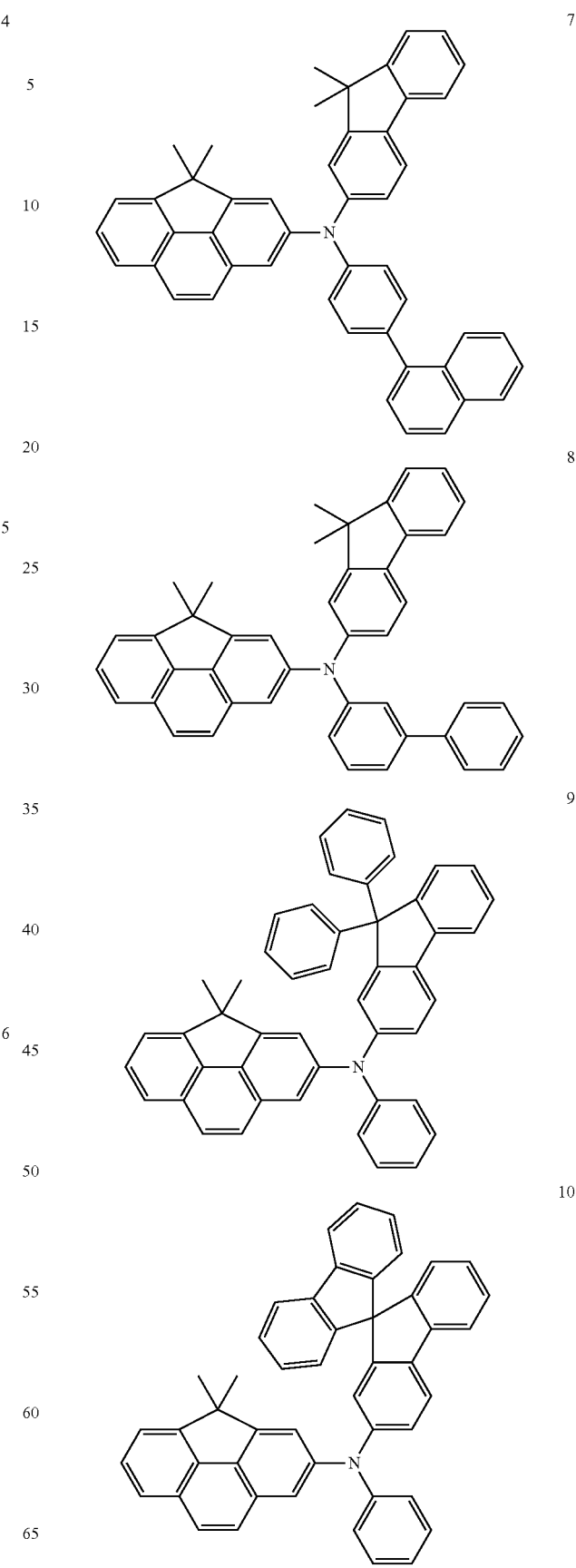

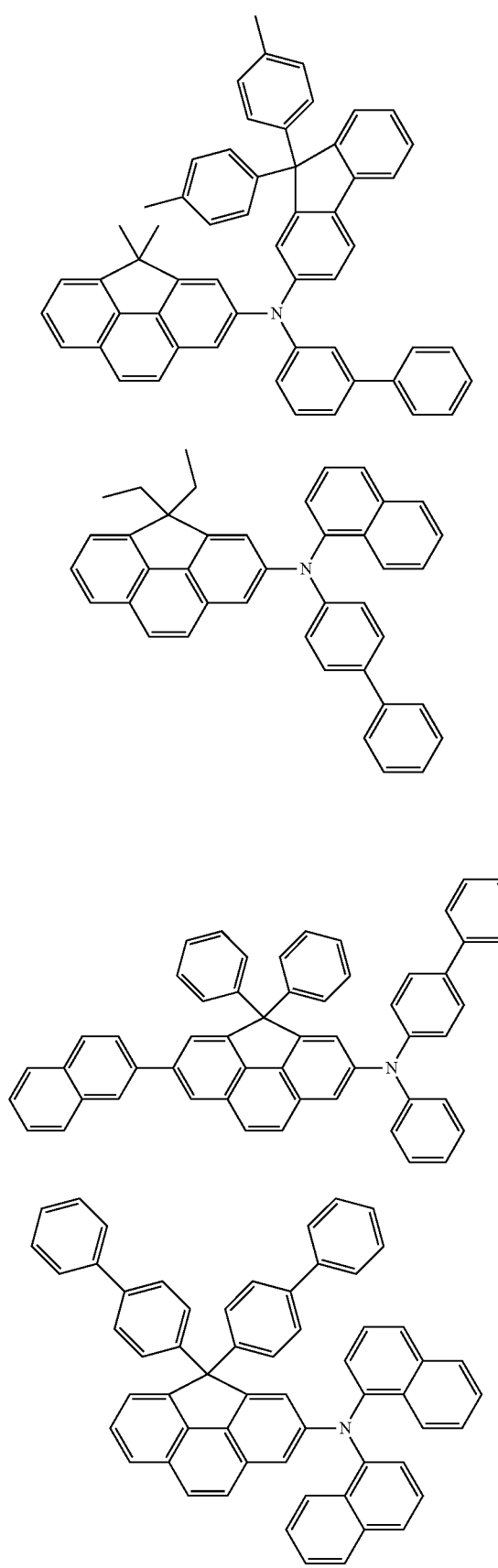
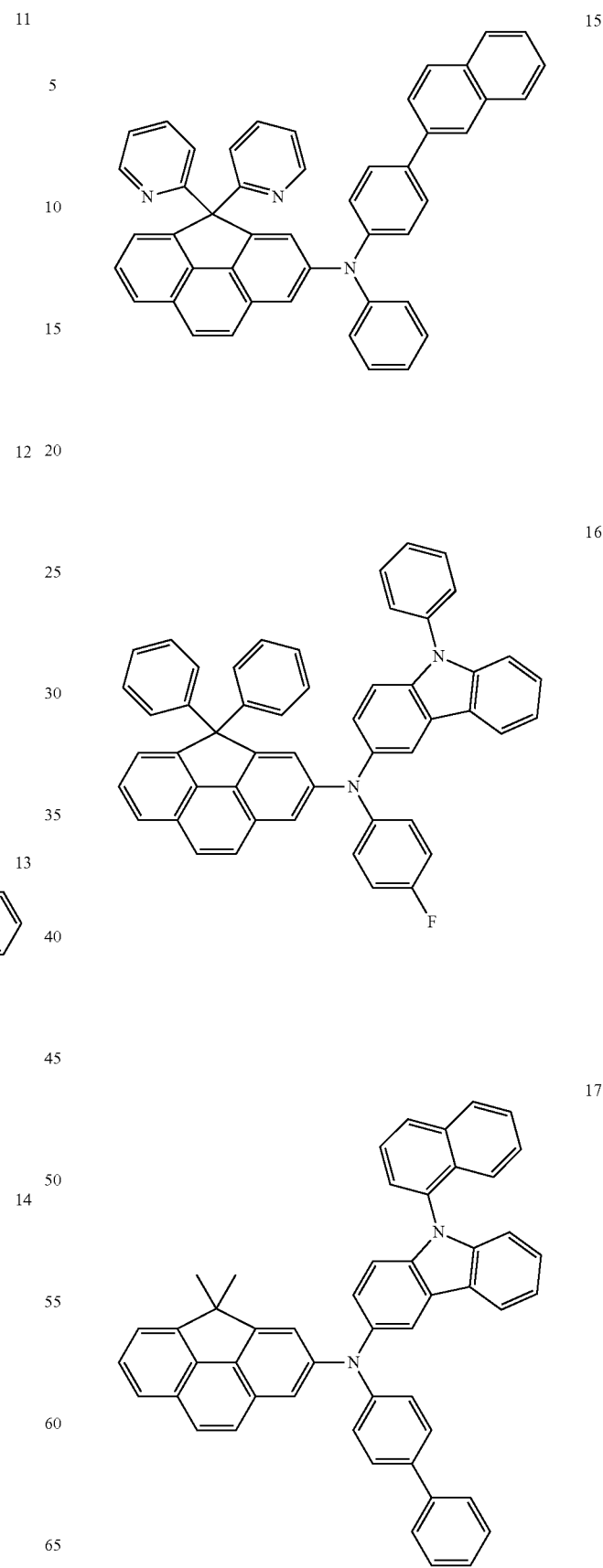

18
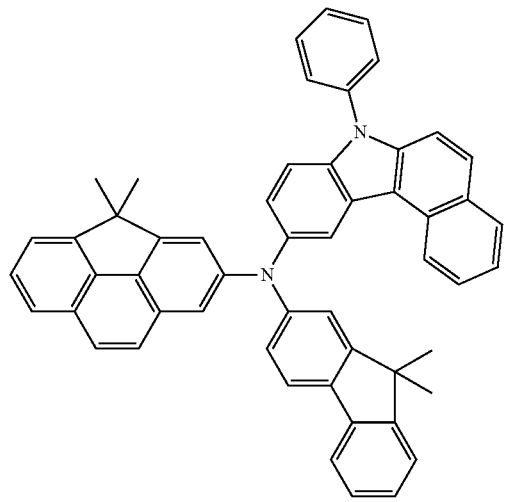
19
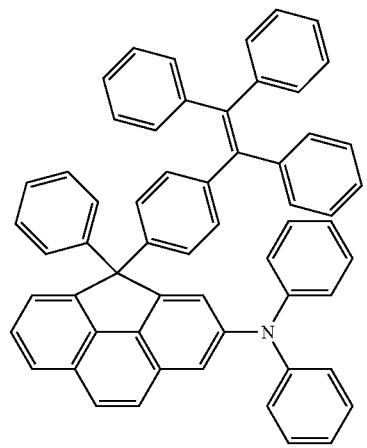
20
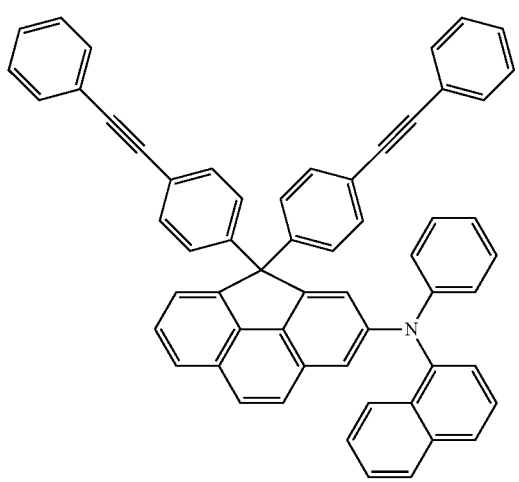
21
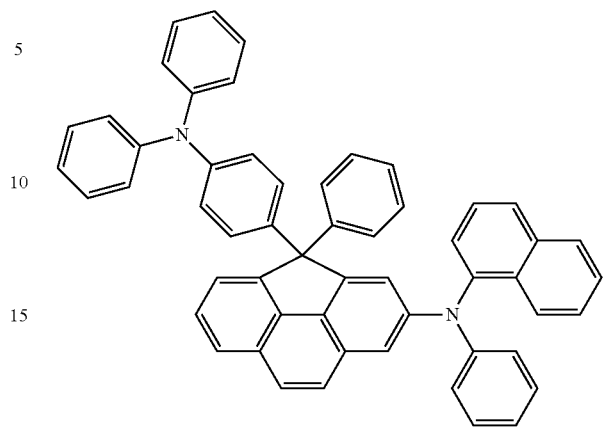
22
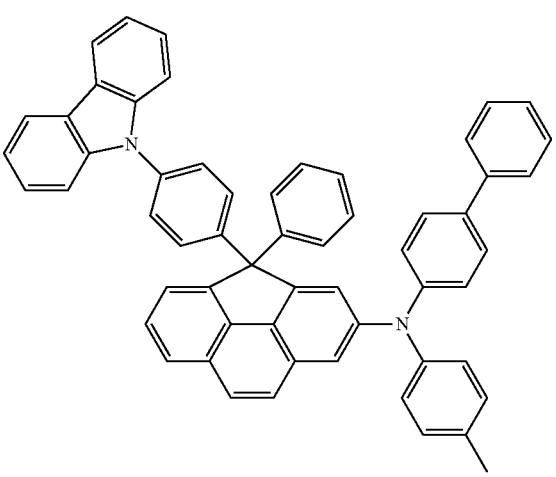
23

24
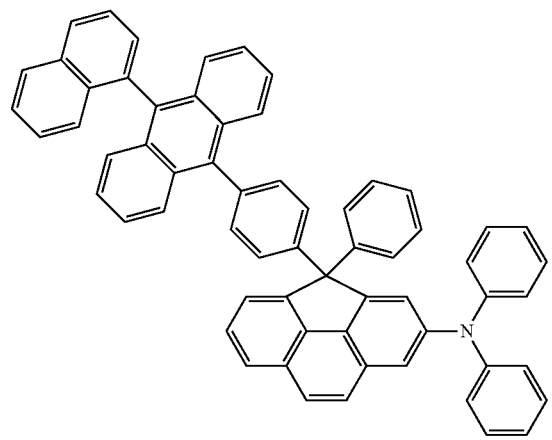
25
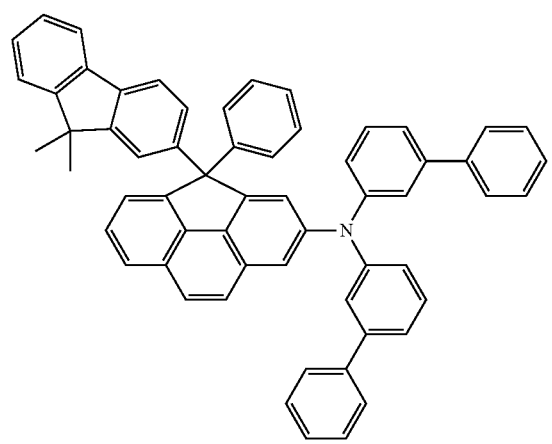
26
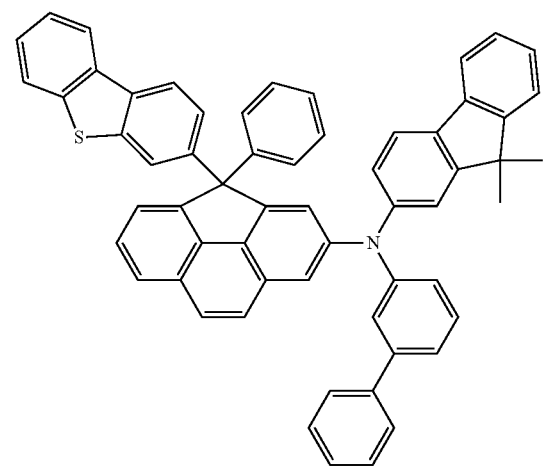
27
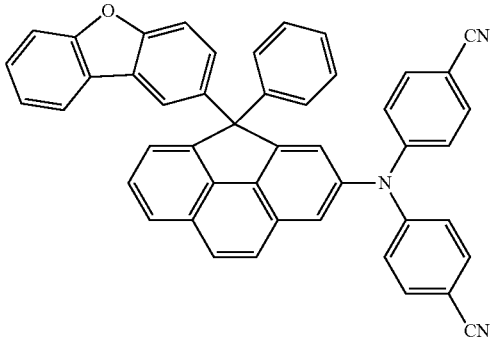
28
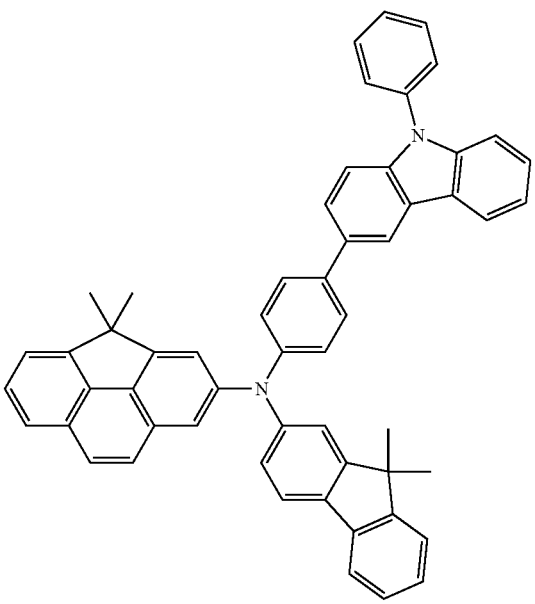
29
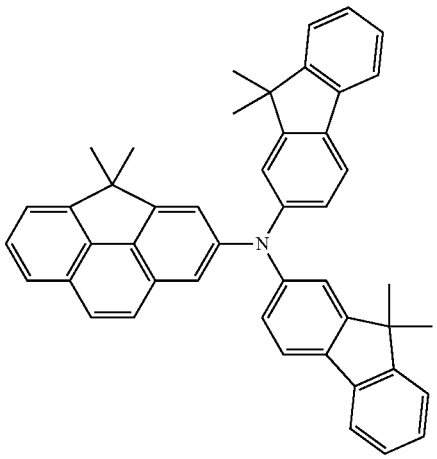

30
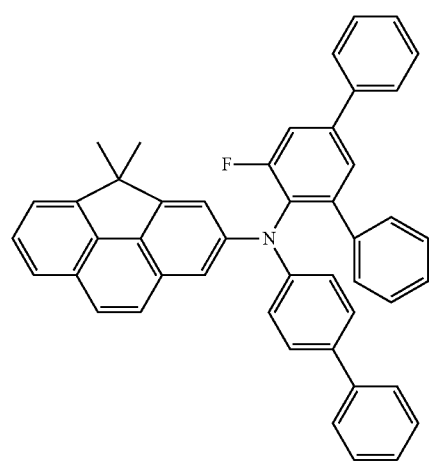
33
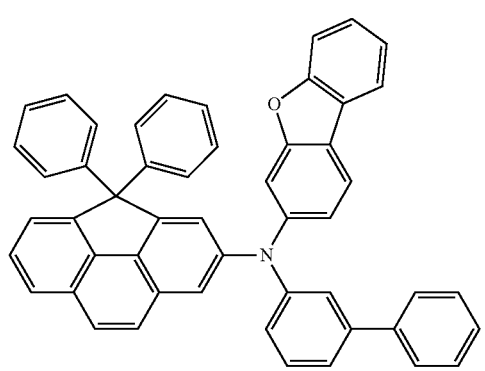
31
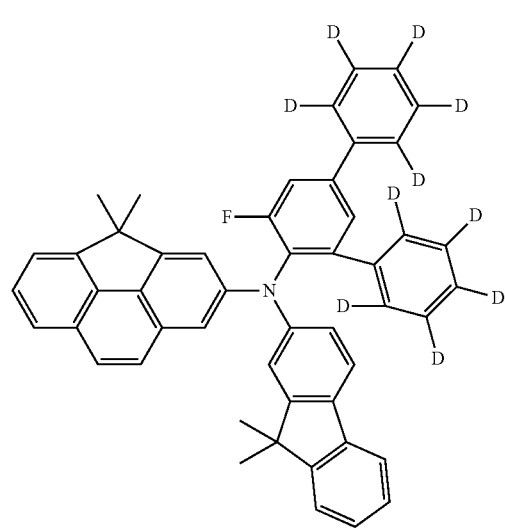
34
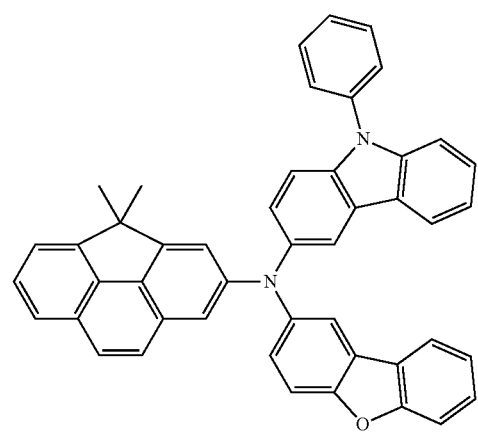
32
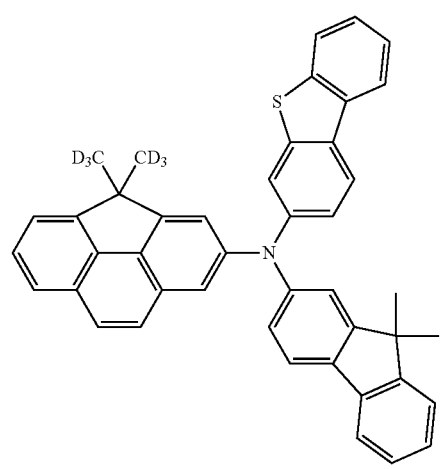
35
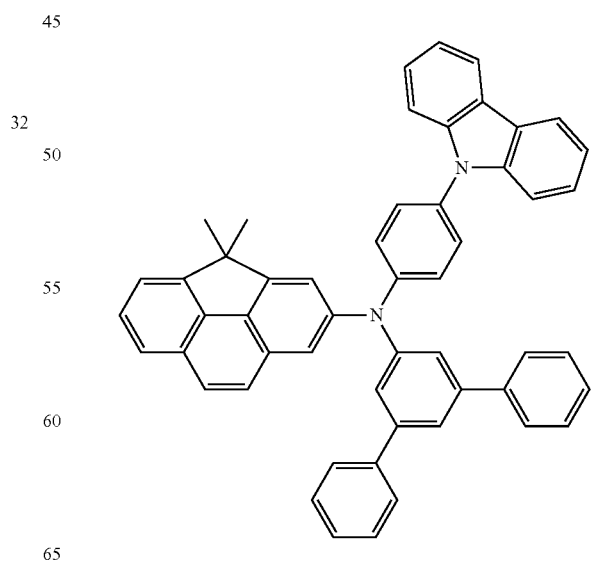

36
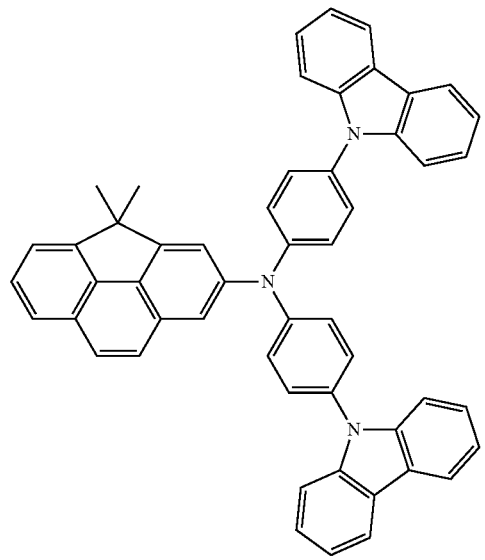
37
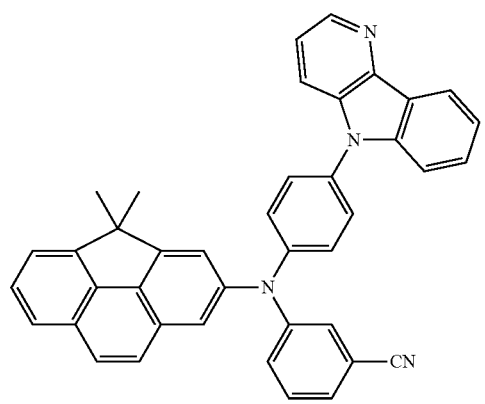
38
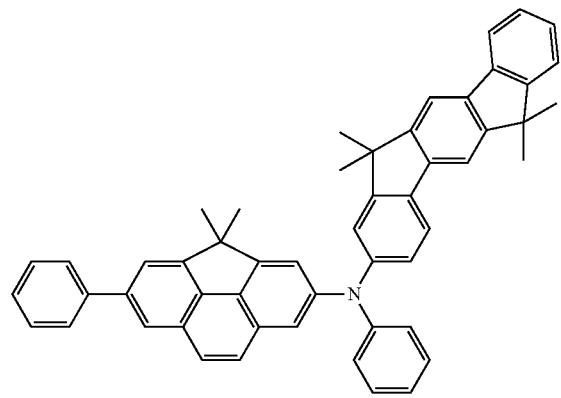
39
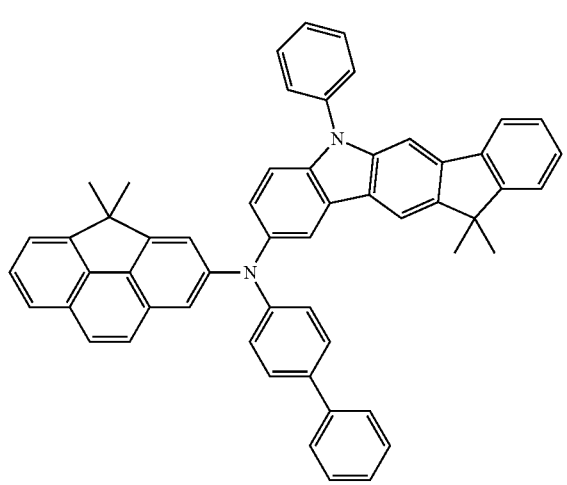
40
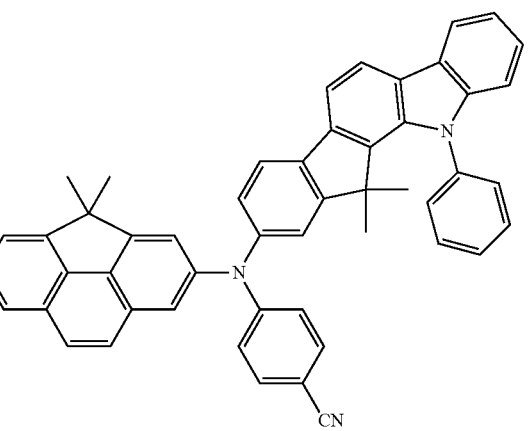
41

42
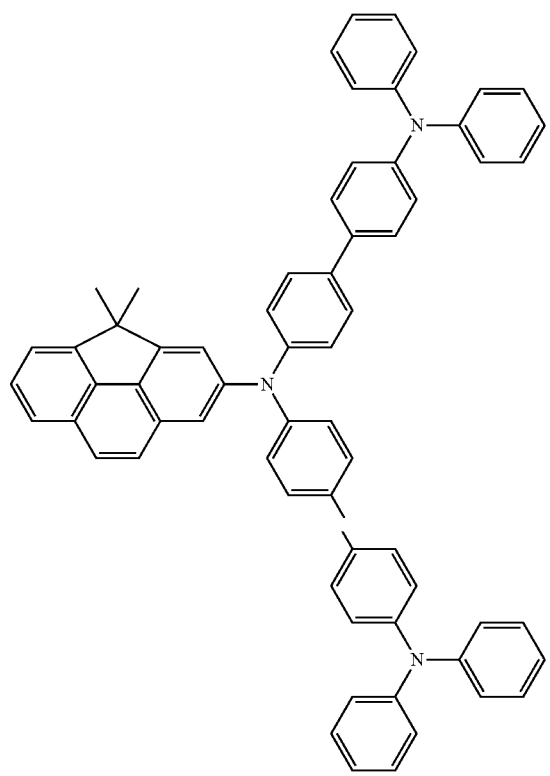
43
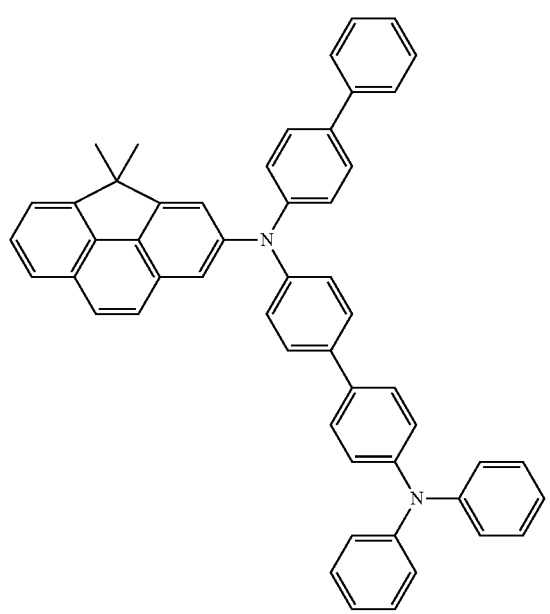
44
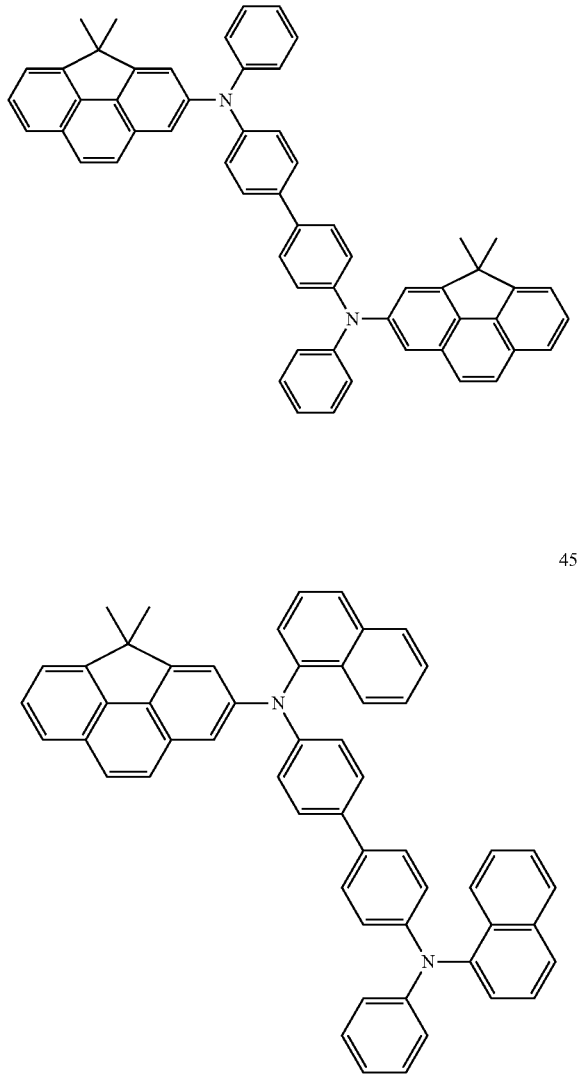
45
46
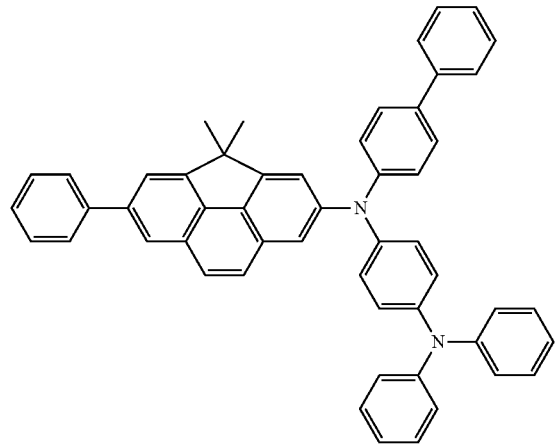

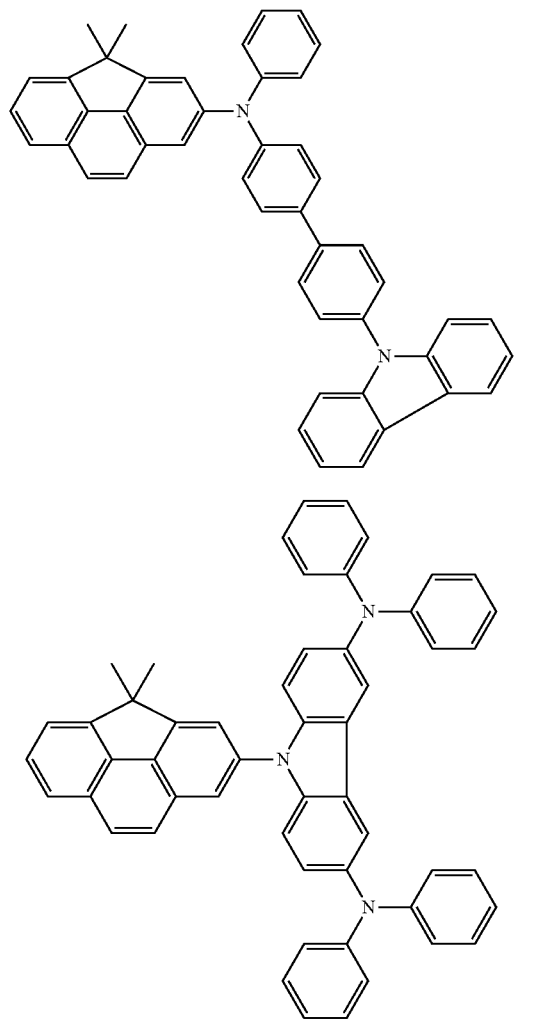
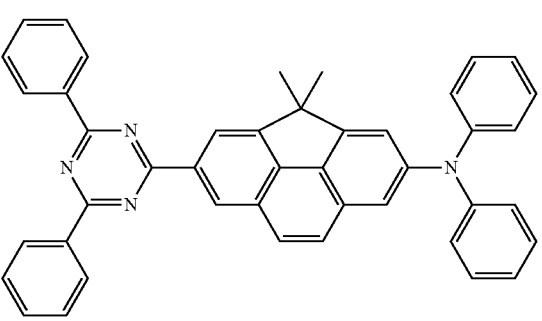
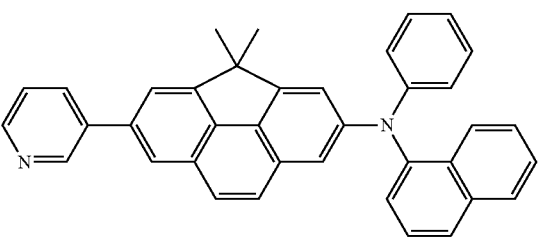
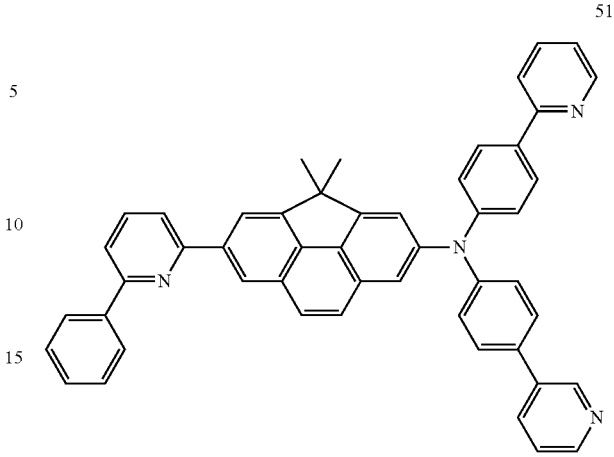

According to another embodiment of the present invention, an OLED includes a first electrode; a second electrode; and an organic layer between the first electrode and the second electrode. The organic layer includes the compound of Formula 1 described above.

The organic layer may include at least one of a hole injection layer (HIL), a hole transport layer (HTL), a functional layer having both hole injection and hole transport abilities (hereinafter, referred to as an "H-functional layer"), a buffer layer, an electron blocking layer (EBL), an emission layer (EML), a hole blocking layer (HBL), an electron transport layer (ETL), an electron injection layer (EIL), and/or a functional layer having both electron transport and electron injection abilities (hereinafter, referred to as "E-functional layer").

In some embodiments, the organic layer may be an EML, and the compound of Formula 1 may be used as a fluorescent host, a phosphorescent host, or a fluorescent dopant.

In one embodiment, the OLED may include an EIL, an ETL, an EML, a HIL, a HTL, or an H-functional layer. The EML may include the compound of Formula 1; and an anthracene-based compound, an arylamine-based compound, or a styryl-based compound.

In one embodiment, the OLED may include an EIL, an ETL, an EML, a HIL, a HTL, or an H-functional layer. Any one of a red layer, a green layer, a blue layer, or a white layer of the EML may include a phosphorescent compound. The HIL, the HTL, or the H-functional layer may include a charge-generating material. In this regard, the charge-generating material may be a p-dopant. Nonlimiting examples of the p-dopant include quinone derivatives, metal oxides, and cyano-containing compounds.

In one embodiment, the organic layer may include an ETL, and the ETL may include an electron transporting organic compound and a metal complex. The metal complex may be a Li complex.

The term "organic layer," as used herein, refers to a single layer and/or a plurality of layers positioned between the first electrode and the second electrode.

The organic layer may include an EML including the compound of Formula 1. Alternatively, the organic layer may include at least one of a HIL, a HTL, and/or an H-functional layer, and at least one of the HIL, the HTL, and/or the H-functional layer may include the compound of Formula 1.

FIG. 1 is a schematic diagram illustrating the structure of an organic light-emitting diode according to an embodiment of the present invention. Hereinafter, a structure and manufacturing method of an OLED will be described in more detail with reference to FIG. 1.

A substrate (not shown) may be any substrate generally used in OLEDs, and may be, for example, a glass substrate or a transparent plastic substrate having good mechanical strength, thermal stability, transparency, surface smoothness, ease of handling, and waterproofness.

The first electrode may be formed by applying a first electrode material on the substrate by deposition or sputtering. When the first electrode is an anode, the first electrode material may be selected from materials having a high work function so as to facilitate hole injection. The first electrode may be a reflective electrode or a transparent electrode. Nonlimiting examples of the first electrode material include indium-tin oxide (ITO), indium-zinc-oxide (IZO), tin oxide ($SnO_2$), and zinc oxide (ZnO), which are transparent and have high conductivity. Also, when magnesium (Mg), aluminum (Al), aluminum-lithium (Al—Li), calcium (Ca), magnesium-indium (Mg—In), or magnesium-silver (Mg—Ag) is used as the first electrode material, the first electrode may be formed as a reflective electrode.

The first electrode may be formed as a single layer or have a multi-layered structure with at least two layers. For example, the first electrode may have a three-layered structure including ITO/Ag/ITO, but is not limited thereto.

The organic layer is formed on the first electrode.

The organic layer may include a HIL, a HTL, a buffer layer (not shown), an EML, an ETL, or an EIL.

The HIL may be formed on the first electrode by using various methods, such as vacuum deposition, spin coating, casting, or LB deposition.

When the HIL is formed by vacuum deposition, the deposition conditions may vary according to the compound used as the material for forming the HIL, the structure of the desired HIL, and the thermal characteristics. For example, the deposition conditions may be, but are not limited to, a deposition temperature of about 100° C. to about 500° C., a degree of vacuum of about $10^{-8}$ torr to about $10^{-3}$ torr, and a deposition speed of about 0.01 Å/sec to about 100 Å/sec.

When the HIL is formed by spin coating, the coating conditions may vary according to the compound used as the material for forming the HIL, the structure of the desired HIL, and the thermal characteristics. For example, the coating conditions may be, but are not limited to, a coating speed of about 2,000 rpm to about 5,000 rpm and a heat treatment temperature for removing the solvent after coating of about 80° C. to about 200° C.

The material for forming the HIL may be a known hole injection material. Nonlimiting examples of the hole injection material include, but are not limited to, N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4"-tris(3-methylphenylphenylamino)triphenylamine (m-MTDATA), N,N'-di(1-naphthyl)-N,N'-diphenylbenzidine (NPB), TDATA, 2-TNATA, polyaniline/dodecylbenzenesulfonic acid (Pani/DBSA), poly(3,4-ethylenedioxythiophene)/poly(4-styrenesulfonate (PEDOT/PSS), polyaniline/camphor sulfonic acid (Pani/CSA), and (polyaniline)/poly(4-styrenesulfonate) (PANI/PSS).

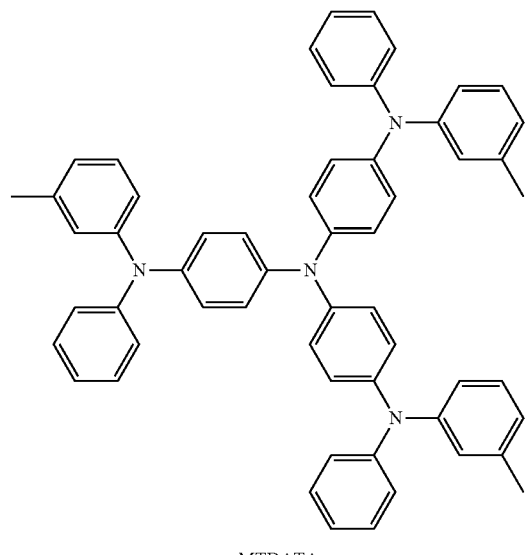

m-MTDATA

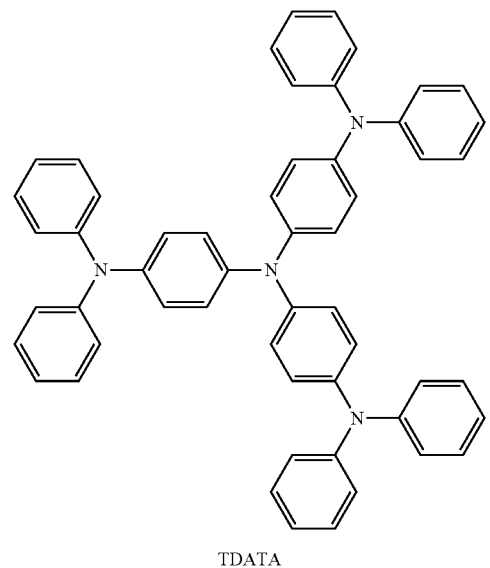

TDATA

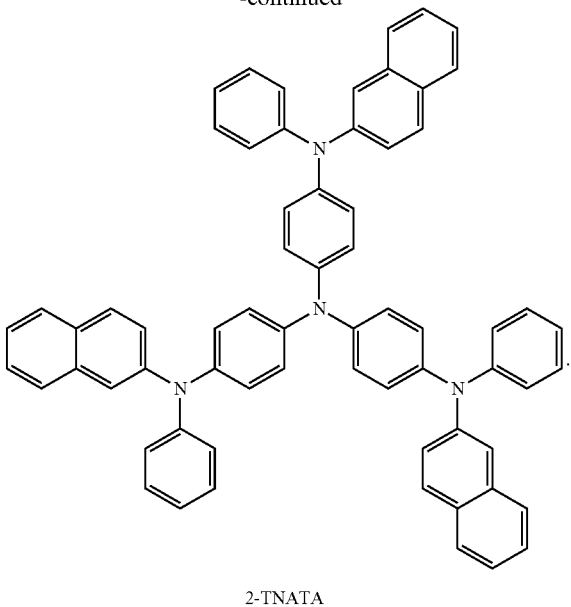

2-TNATA

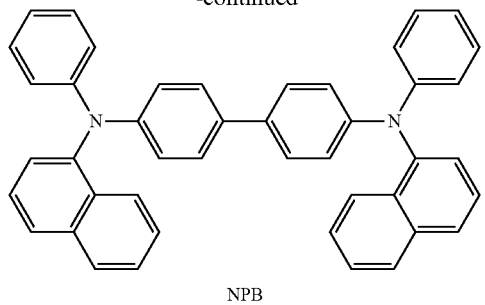

NPB

The thickness of the HTL may be about 50 Å to about 2,000 Å. In some embodiments, the thickness of the HTL may be about 100 Å to about 1,500 Å. When the thickness of the HTL is within these ranges, satisfactory hole transport properties may be obtained without a substantial increase in driving voltage.

The H-functional layer may include at least one of the hole injection materials and the hole transporting materials described above. The thickness of the H-functional layer may be about 500 Å to about 10,000 Å. In some embodiments, the thickness of the HTL may be about 100 Å to about 1,000 Å. When the thickness of the H-functional layer is within these ranges, satisfactory hole injection and hole transport properties may be obtained without a substantial increase in driving voltage.

At least one of the HIL, the HTL, and/or the H-functional layer may include at least one compound represented by Formula 300 below and/or a compound represented by Formula 350 below:

The thickness of the HIL may be about 100 Å to about 10,000 Å. In some embodiments, the thickness of the HIL may be about 100 Å to about 1,000 Å. When the thickness of the HIL is within these ranges, satisfactory hole injection properties may be obtained without a substantial increase in driving voltage.

Next, the HTL may be formed on the HIL by various methods, such as vacuum deposition, spin coating, casting, or LB deposition. When the HTL is formed by vacuum deposition or spin coating, the deposition or coating conditions may vary according to the compounds used. However, in general, the deposition or coating conditions may be similar or identical to the conditions used for forming the HIL.

A material for forming the HTL may be the compound of Formula 1 or a known hole transporting material. Nonlimiting examples of the hole transporting material include, but are not limited to, carbazole derivatives such as N-phenylcarbazole and polyvinylcarbazole, N,N'-bis(3-methylphenyl)-N,N'-diphenyl-[1,1-biphenyl]-4,4'-diamine (TPD), 4,4',4"-tris(N-carbazolyl)triphenylamine (TCTA), and N,N'-di(1-naphthyl)-N,N'-diphenylbenzidine (NPB).

Formula 300

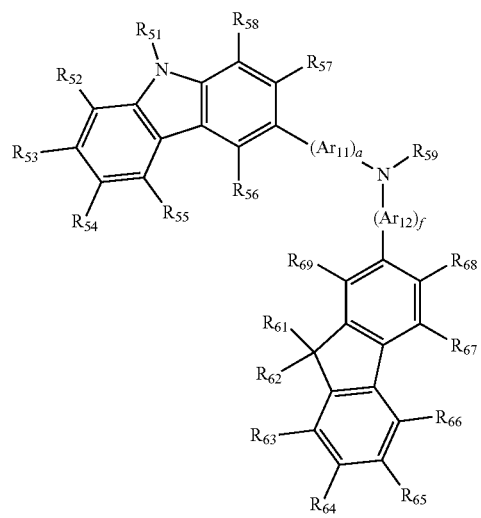

Formula 350

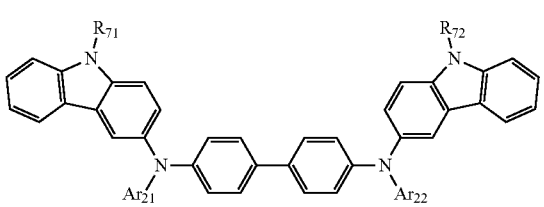

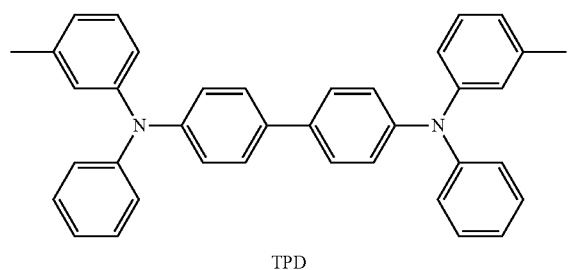

TPD

In Formulae 300 and 350, $Ar_{11}$, $Ar_{12}$, $Ar_{21}$, and $Ar_{22}$ are each independently a substituted or unsubstituted $C_6$-$C_{60}$ arylene group.

In Formula 300, e and f may be each independently an integer of 0 to 5, for example, 0, 1, or 2. For example, e may be 1 and f may be 0, but e and f are not limited thereto.

In Formulae 300 and 350, $R_{51}$ through $R_{58}$, $R_{61}$ through $R_{69}$, $R_{71}$, and $R_{72}$ may be each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, or a substituted or unsubstituted $C_6$-$C_{60}$ arylthio group. For example, $R_{51}$ through $R_{58}$, $R_{61}$ through $R_{69}$, $R_{71}$, and $R_{72}$ may be each independently one of hydrogen; deuterium; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid group or a salt thereof; a $C_1$-$C_{10}$ alkyl group (for example, a methyl group, an ethyl group, a propyl group, a butyl group, a pentyl group, a hexyl group, and the like); a $C_1$-$C_{10}$ alkoxy group (for example, a methoxy group, an ethoxy group, a propoxy group, a butoxy group, a pentoxy group, and the like); a $C_1$-$C_{10}$ alkyl group or a $C_1$-$C_{10}$ alkoxy group substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, and a phosphoric acid group or a salt thereof; a phenyl group; a naphthyl group; an anthryl group; a fluorenyl group; a pyrenyl group; or a phenyl group, a naphthyl group, an anthryl group, a fluorenyl group, or a pyrenyl group substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, or a $C_1$-$C_{10}$ alkoxy group.

In Formula 300, $R_{59}$ may be one of a phenyl group; a naphthyl group; an anthryl group; a biphenyl group; a pyridyl group; or a phenyl group, a naphthyl group, an anthryl group, a biphenyl group or a pyridyl group substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a substituted or unsubstituted $C_1$-$C_{20}$ alkyl group, or a substituted or unsubstituted $C_1$-$C_{20}$ alkoxy group.

In one embodiment, the compound of Formula 300 may be a compound represented by Formula 300A below, but is not limited thereto:

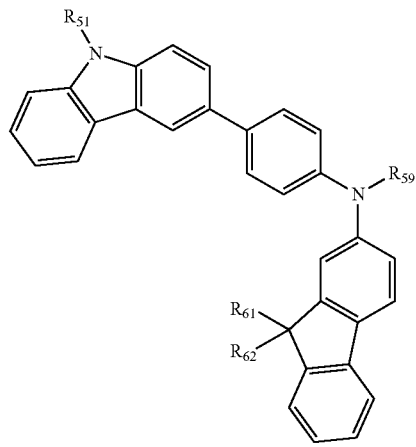

Formula 300A

In Formula 300A, $R_{51}$, $R_{60}$, $R_{61}$, and $R_{59}$ are the same as defined above.

For example, at least one of the HIL, the HTL, or the H-functional layer may include at least one of Compounds 301 through 320 below, but is not limited thereto.

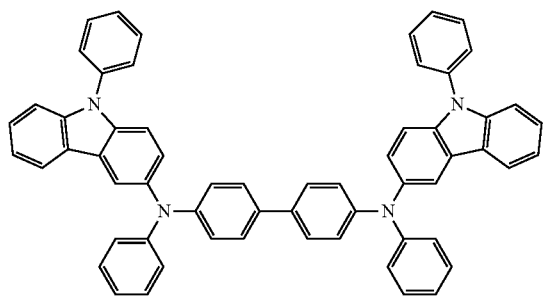

301

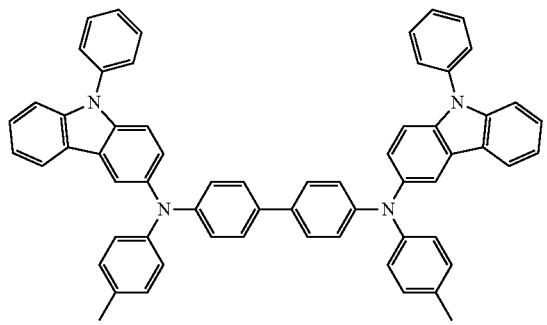

302

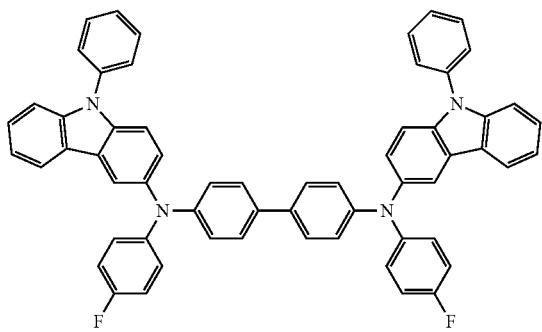
303
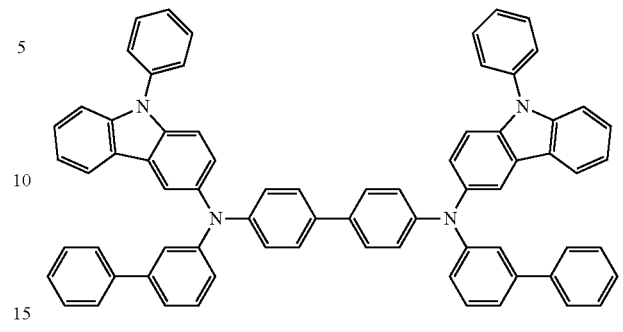
307
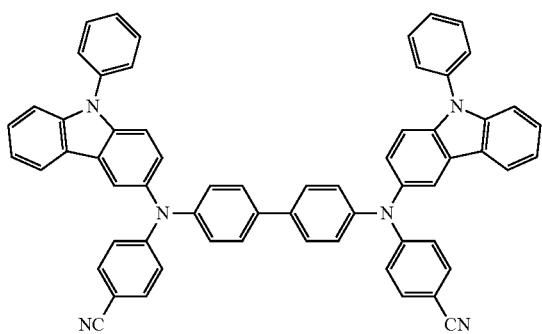
304
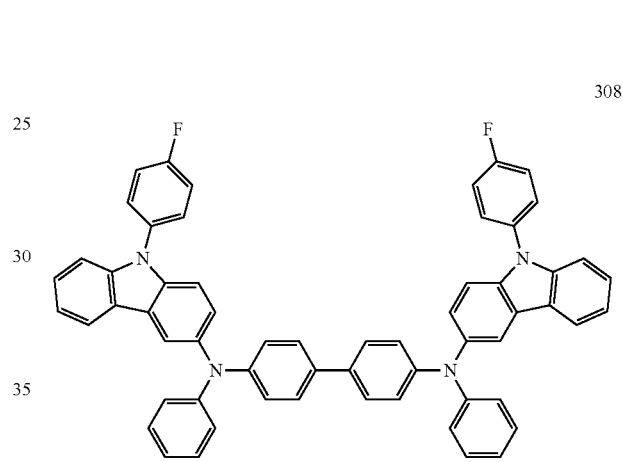
308
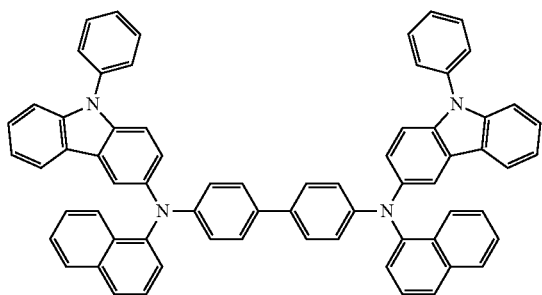
305
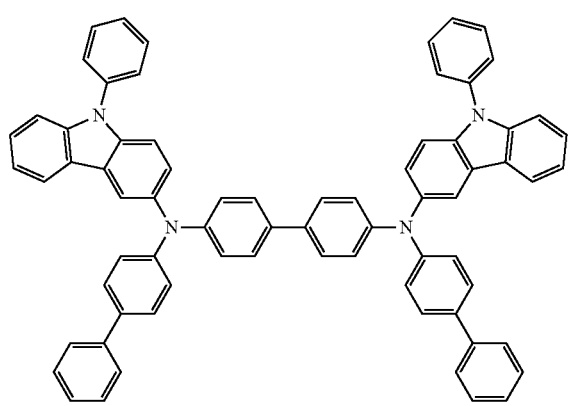
306
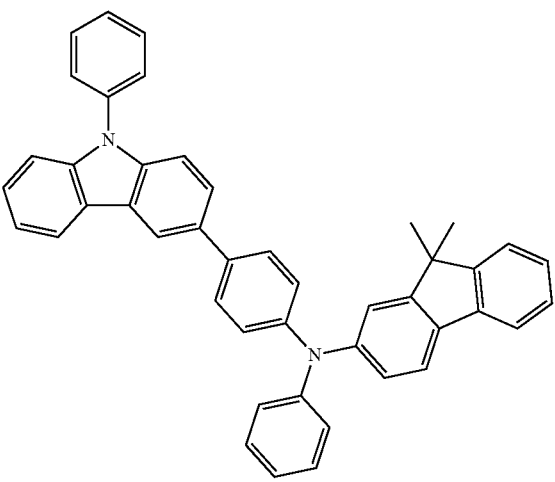
309

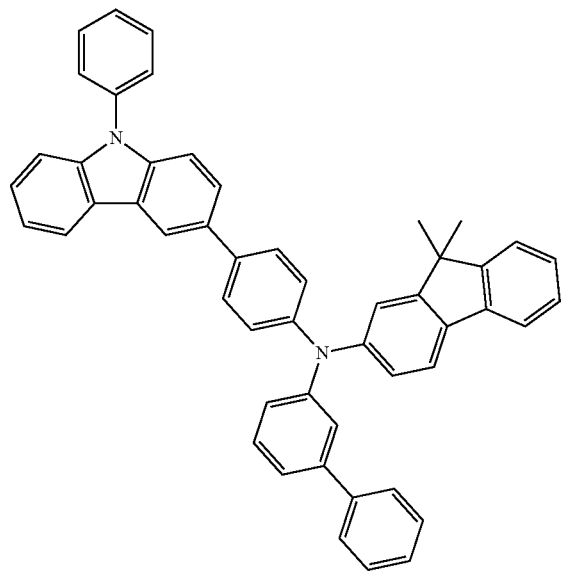
310
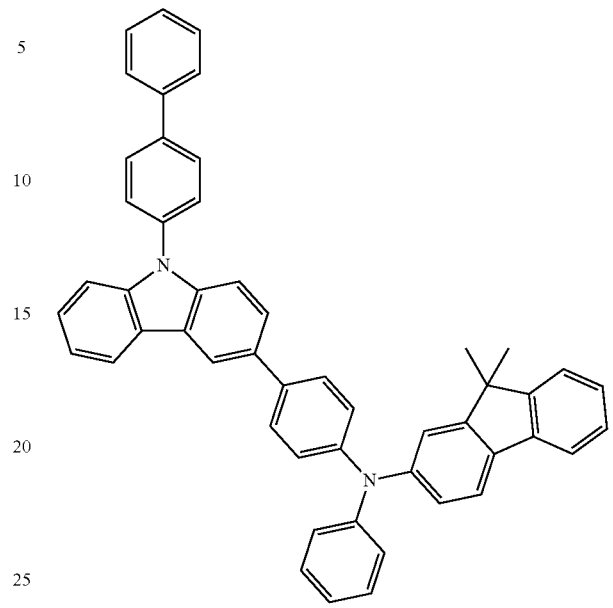
312
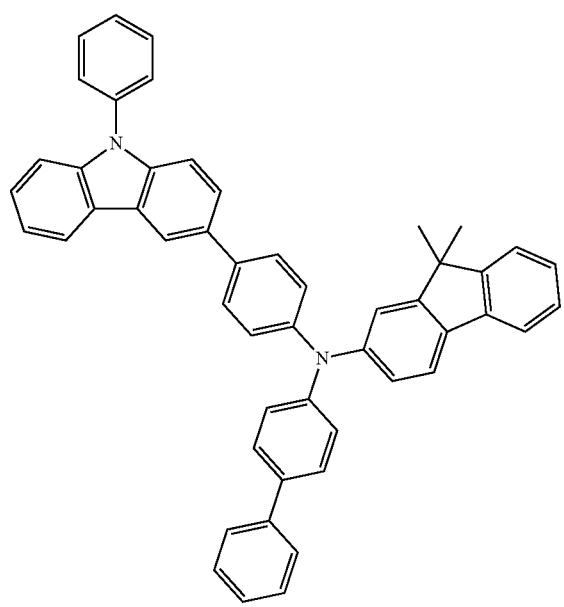
311
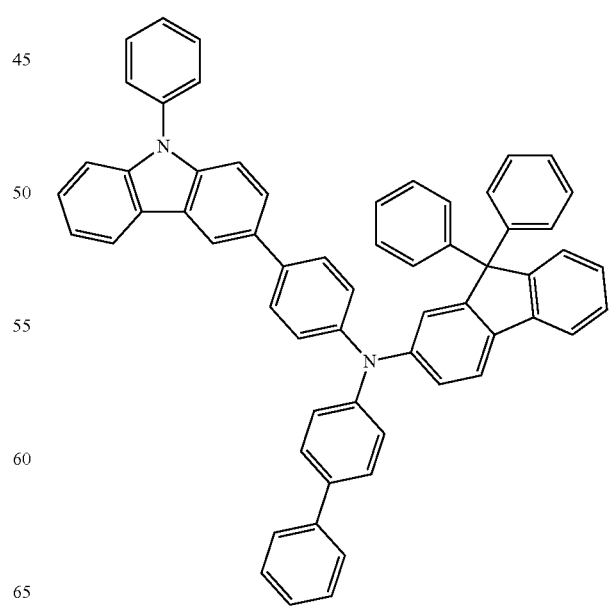
313

314
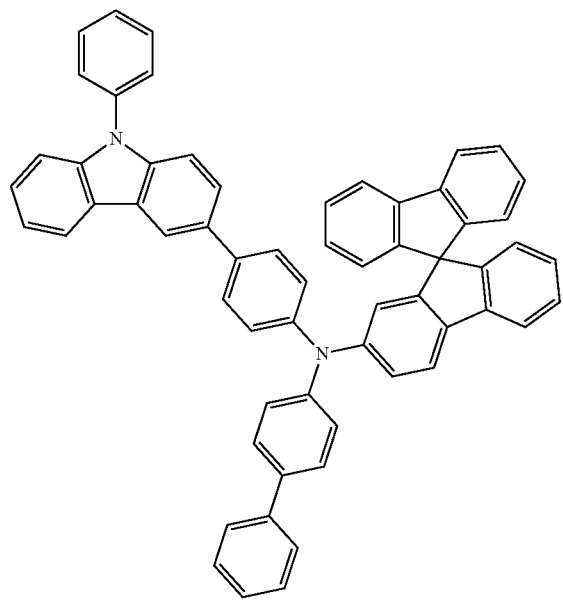
315
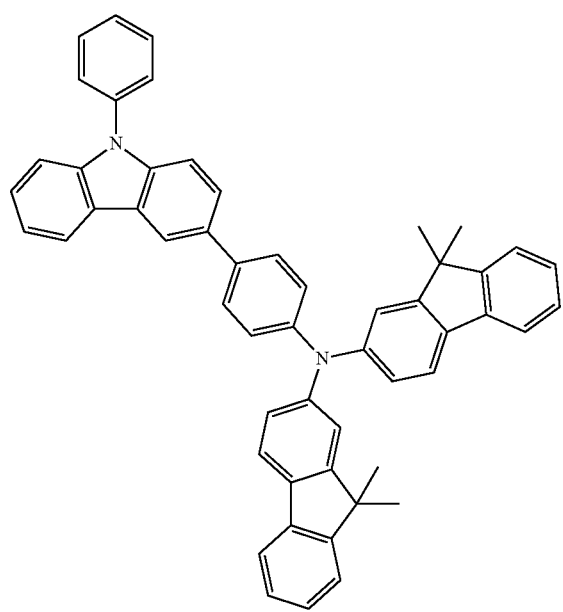
316
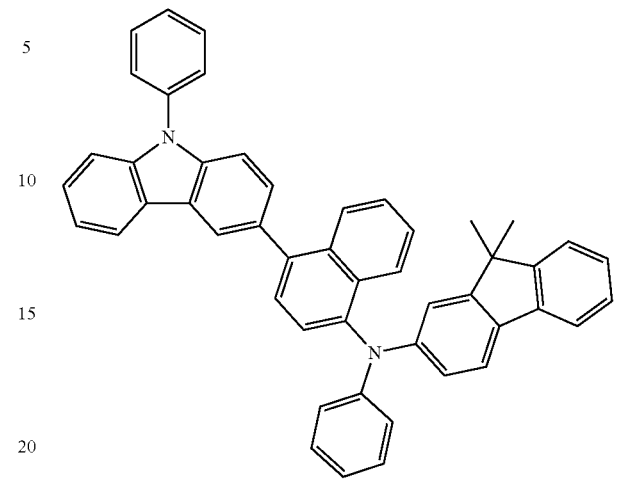
317
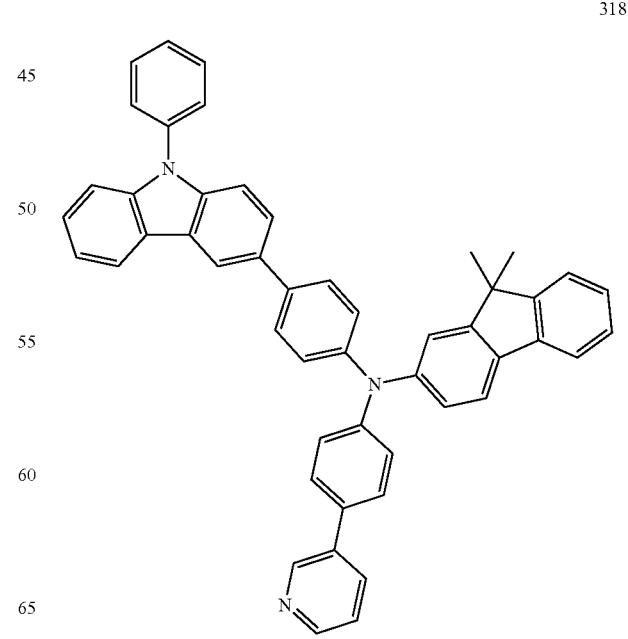

319

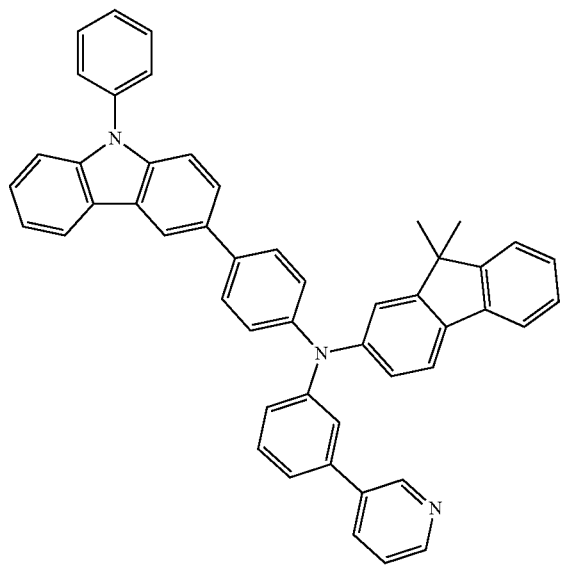

Compound 200

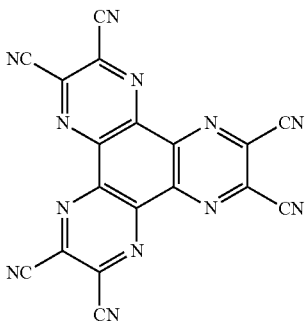

F4-CTNQ

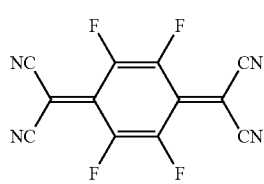

320

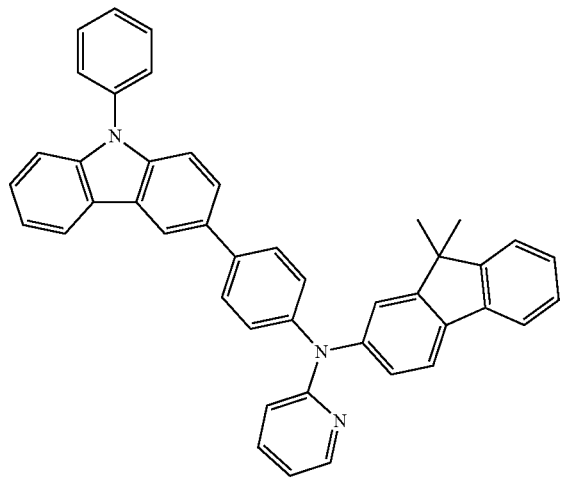

At least one of the HIL, the HTL, and the H-functional layer may further include a charge-generating material so as to increase the conductivity of the layers, in addition to the hole injection material, the hole transporting material and/or the material having hole injection and hole transport abilities.

The charge-generating material may be, for example, a p-dopant. The p-dopant may be one selected from quinone derivatives, metal oxides, and cyano-containing compounds, but is not limited thereto. Nonlimiting examples of the p-dopant include quinone derivatives such as tetra-cyano-quinodimethane (TCNQ) and 2,3,5,6-tetrafluoro-tetra-cyano-1,4-benzoquinodimethane (F4-CTNQ); metal oxides such as an tungsten oxide and molybdenum oxide; and cyano-containing compounds such as Compound 200 below and the like.

When the HIL, the HTL or the H-functional layer further includes the charge-generating material, the charge-generating material may be homogeneously or inhomogeneously dispersed in these layers.

The buffer layer may be positioned between the EML and at least one of the HIL, the HTL, or the H-functional layer. The buffer layer may increase efficiency by compensating for an optical resonance distance according to the wavelength of light emitted from the EML. The buffer layer may include a hole injection material and a hole transporting material. Also, the buffer layer may include the same material as one of the materials included in the HIL, the HTL, or the H-functional layer (which are formed below the buffer layer).

Next, the EML may be formed on the HTL, the H-functional layer, or the buffer layer by vacuum deposition, spin coating, casting, or LB deposition. When the EML is formed by vacuum deposition or spin coating, the deposition or coating conditions may vary according to the compounds used. However, in general, the conditions may be similar or identical to the conditions for forming the HIL.

The EML may include one of the compounds of Formula 1 according to embodiments of the present invention.

The EML may further include a host.

Nonlimiting examples of the host include $Alq_3$, 4,4'-N,N'-dicabazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di(naphth-2-yl) anthracene (TBADN), E3, and distyrylarylene (DSA), dmCBP (refer to the following formula), and Compounds 501 through 509 below.

TPBI
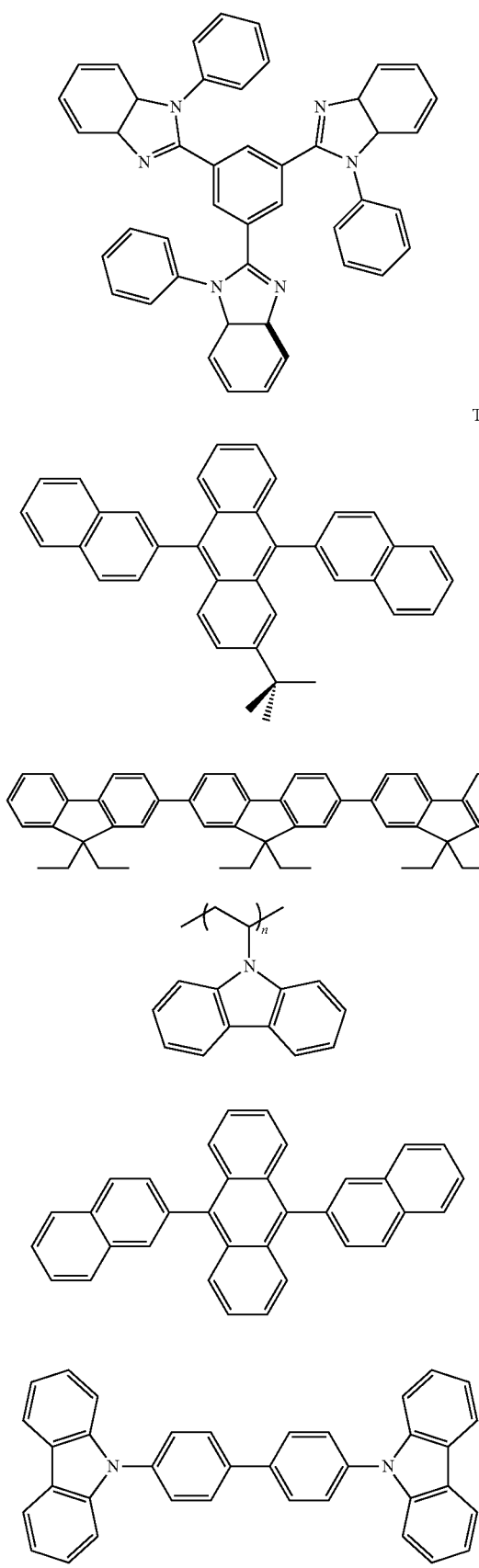
TBADN
E3
PVK
ADN
CBP
dmCMP
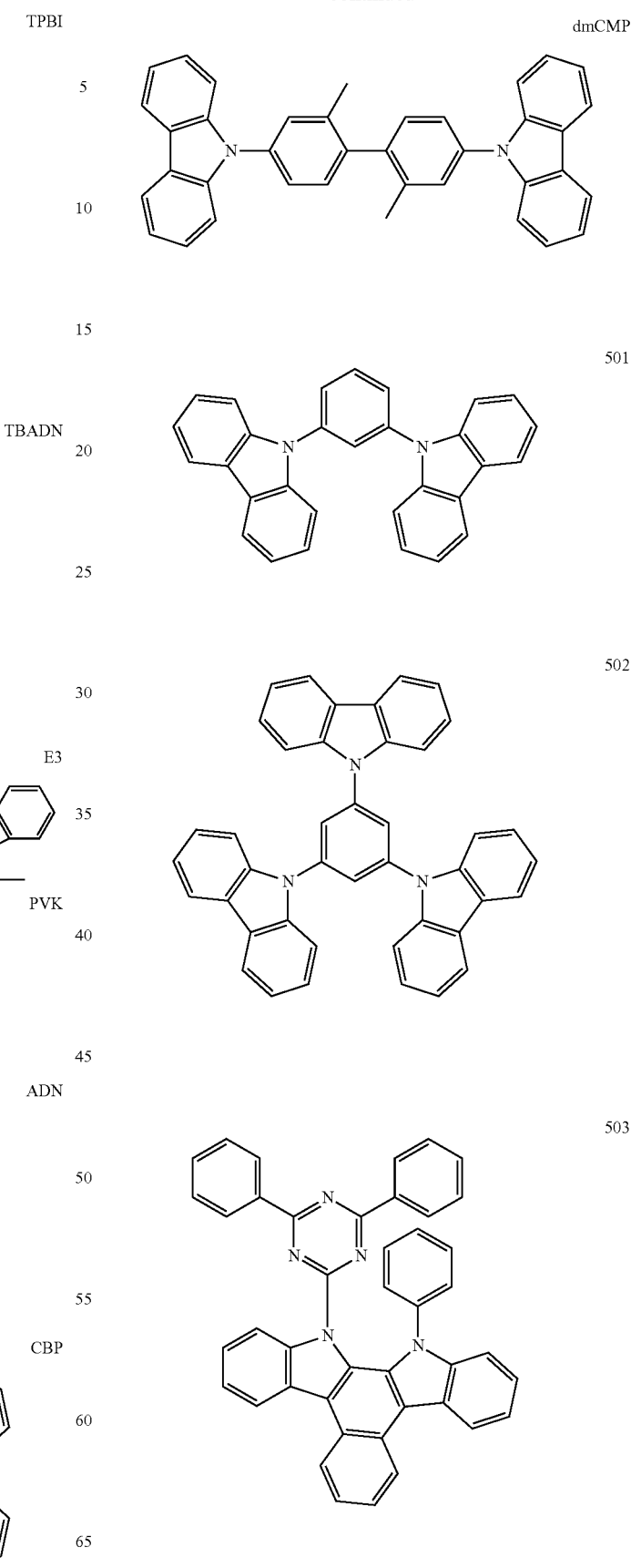
501
502
503

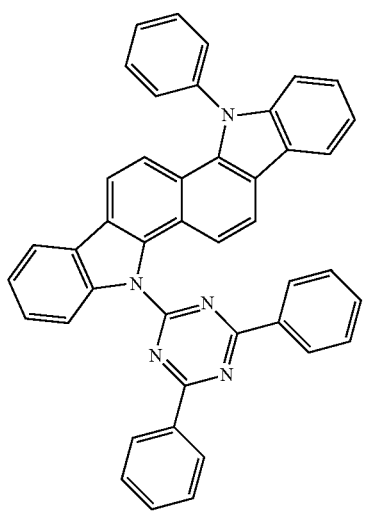

504

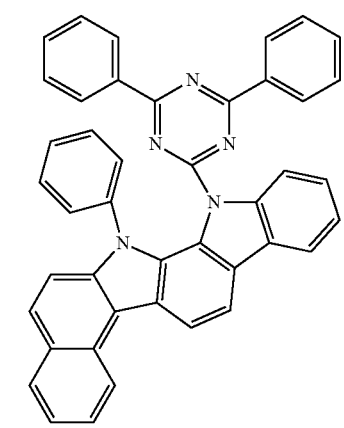

505

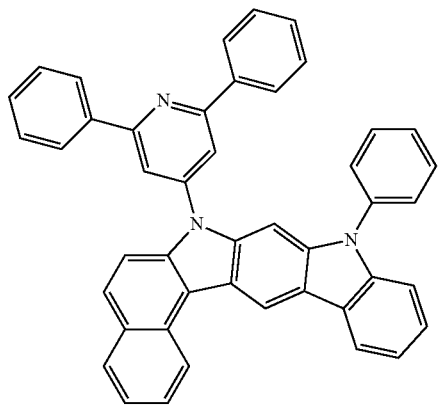

506

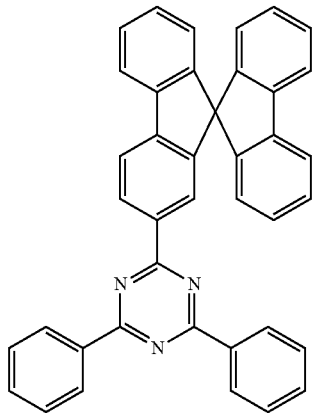

507

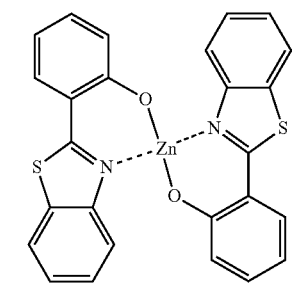

508

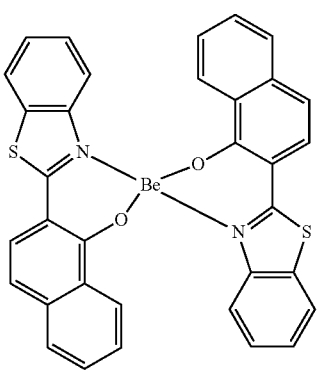

509

Also, the host may be an anthracene-based compound represented by Formula 400 below.

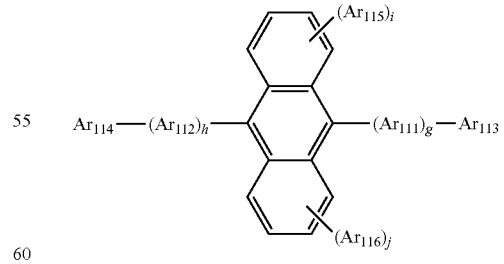

Formula 400

In Formula 400, $Ar_{111}$ and $Ar_{112}$ are each a independently substituted or unsubstituted $C_6$-$C_{60}$ arylene group. $Ar_{113}$ through $Ar_{116}$ are each independently a substituted or unsubstituted $C_1$-$C_{10}$ alkyl group or a substituted or unsubstituted $C_6$-$C_{60}$ aryl group. Also, g, h, i, and j may be each independently an integer of 0 to 4.

For example, in Formula 400, $Ar_{111}$ and $Ar_{112}$ may be each independently one of a phenylene group, a naphthylene group, a phenanthrenylene group, a pyrenylene group; or a phenylene group, a naphthylene group, a phenanthrenylene group, a fluorenyl group, or a pyrenylene group substituted with at least one of a phenyl group, a naphthyl group, or an anthryl group, but are not limited thereto.

In Formula 400, g, h, i, and j may be each independently 0, 1, or 2.

In Formula 400, $Ar_{113}$ through $Ar_{116}$ may be each independently one of a $C_1$-$C_{10}$ alkyl group that is substituted with at least one of a phenyl group, a naphthyl group, or an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group or a fluorenyl group substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, or a fluorenyl group; or

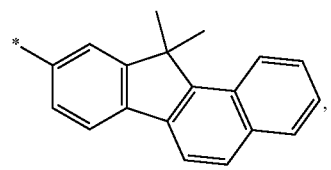 [SMILES: *c1ccc2c(c1)C(C)(C)c1c-2ccc2ccccc12]

but are not limited thereto.

For example, the anthracene-based compound of Formula 400 may be one of the following compounds, but is not limited thereto.

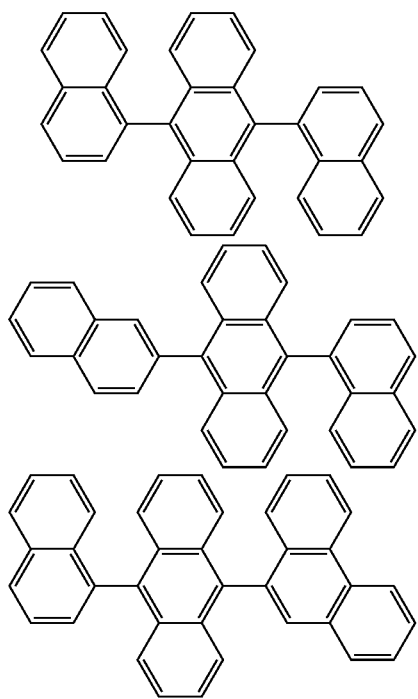

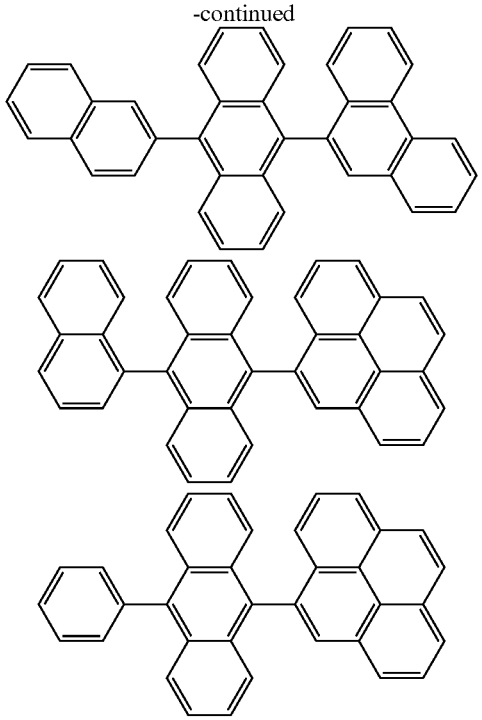

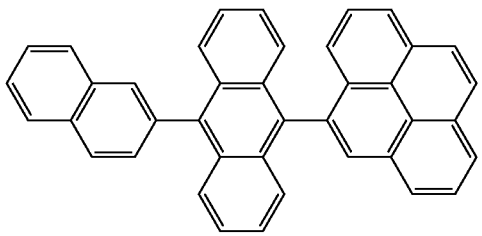

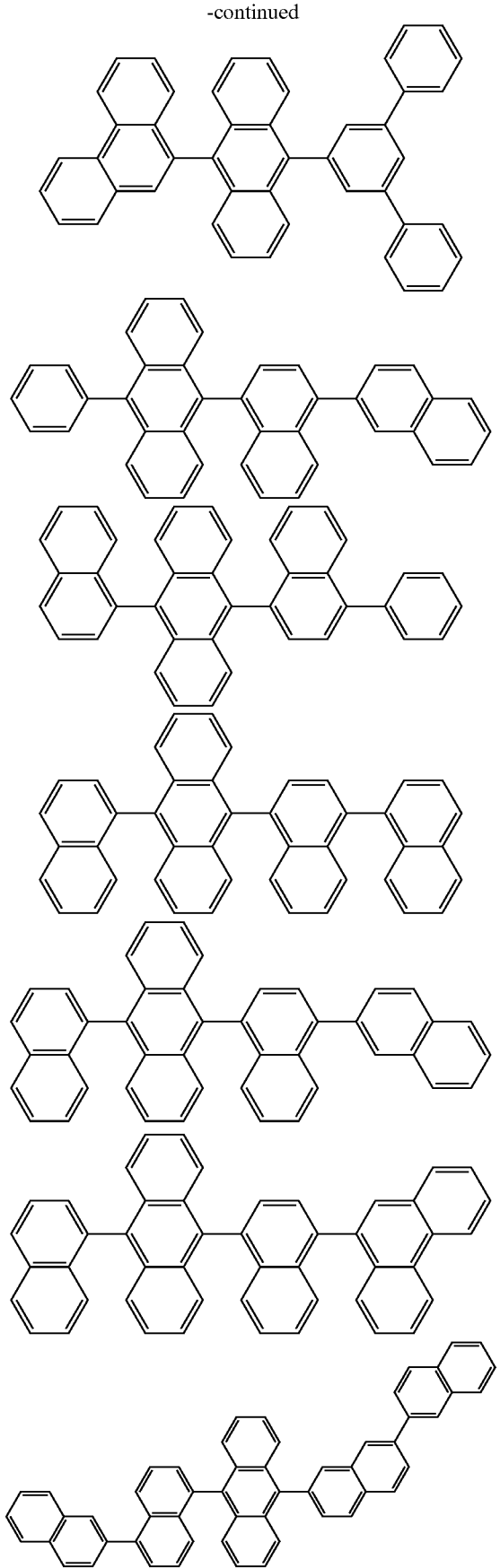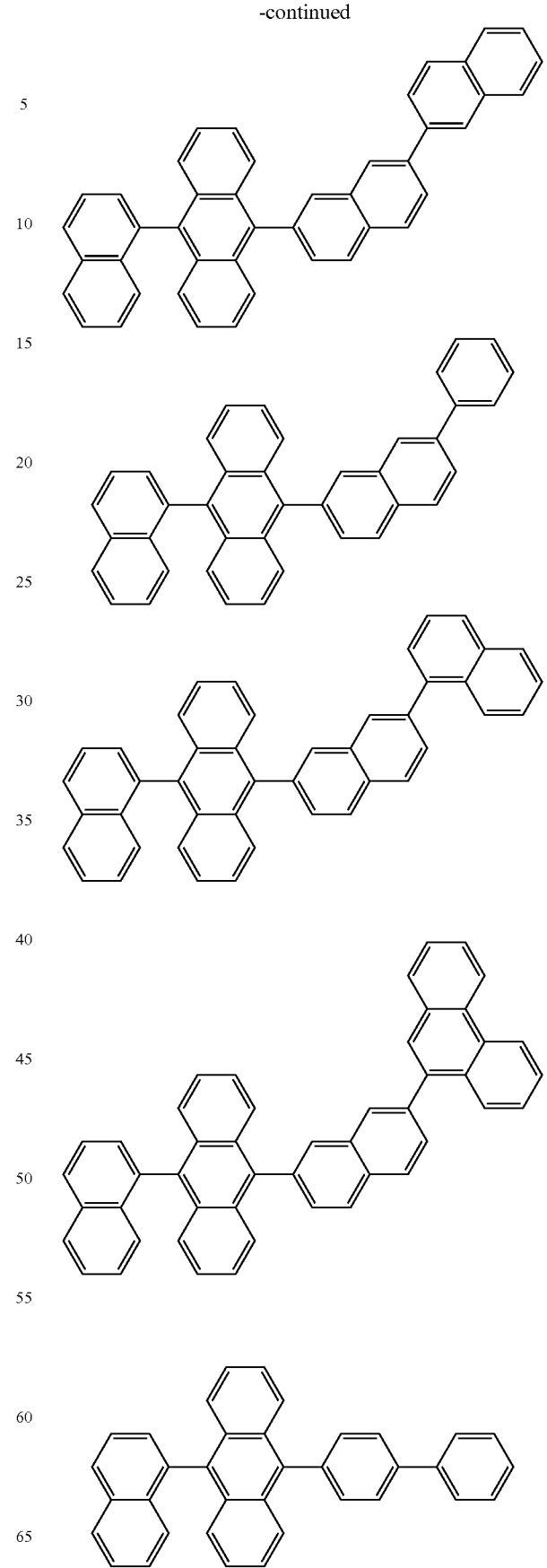

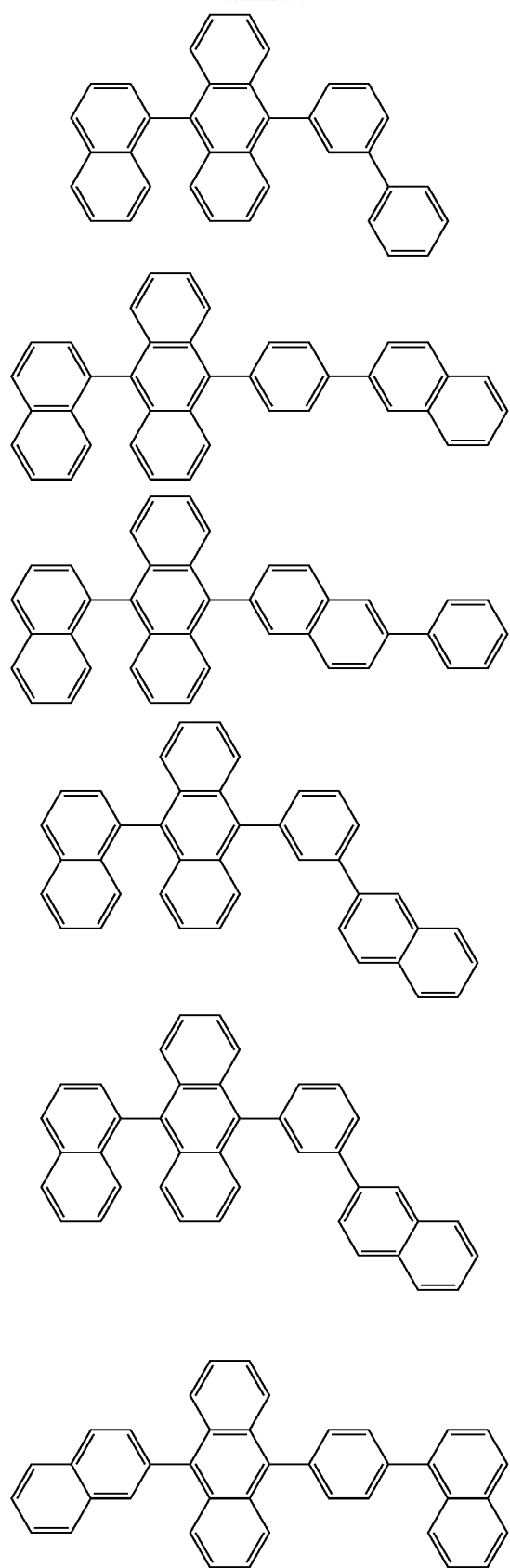
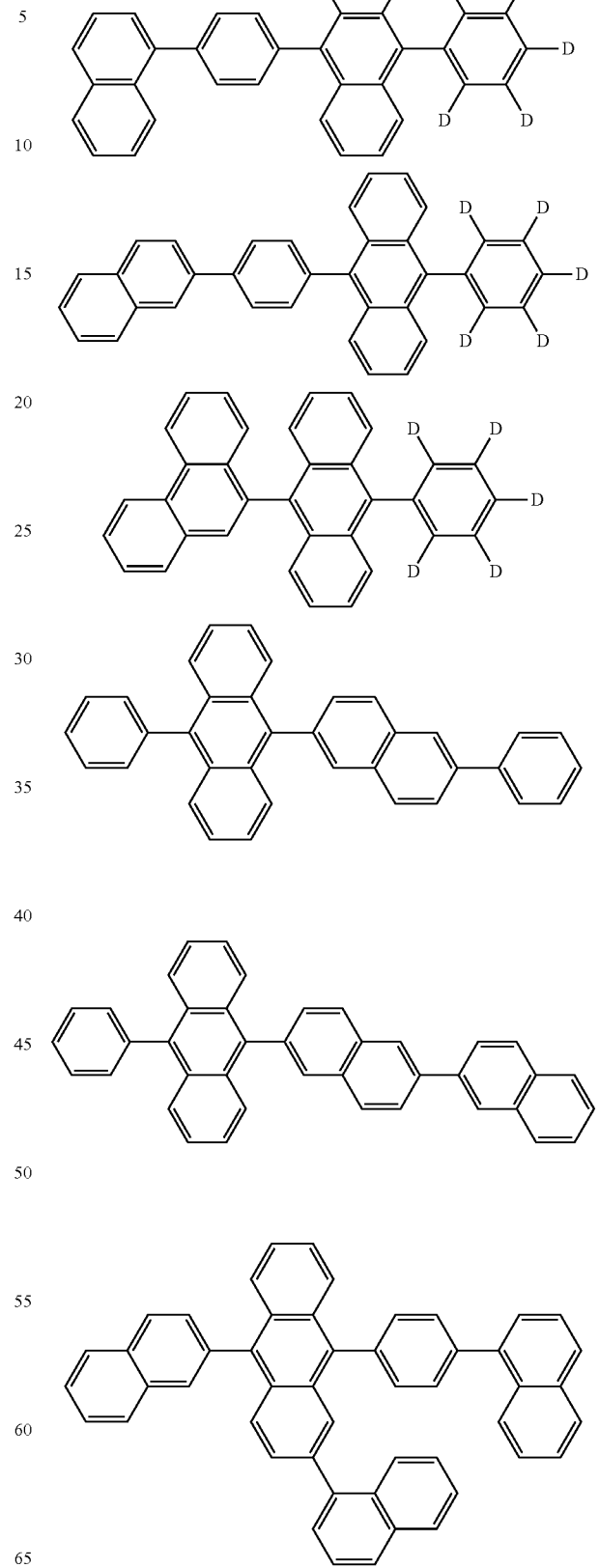

-continued

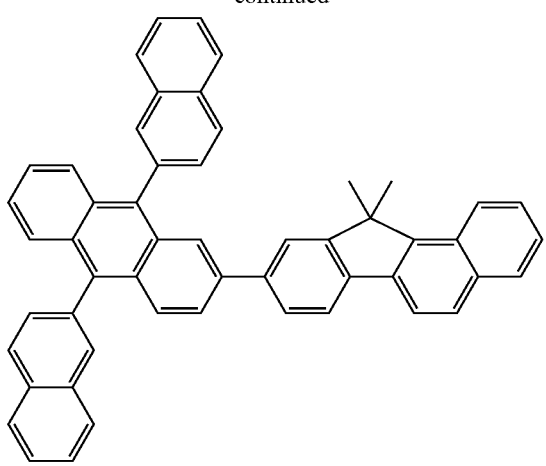

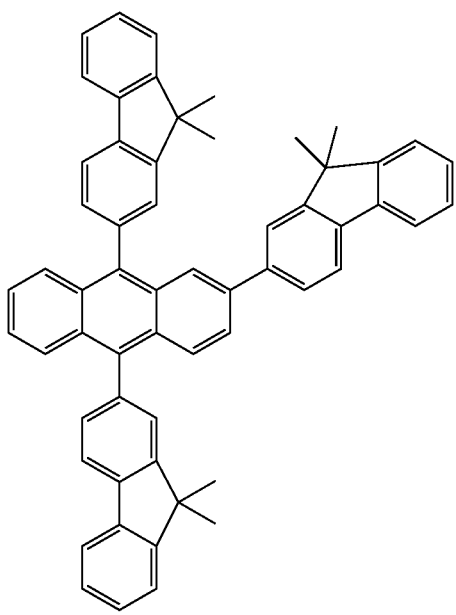

-continued

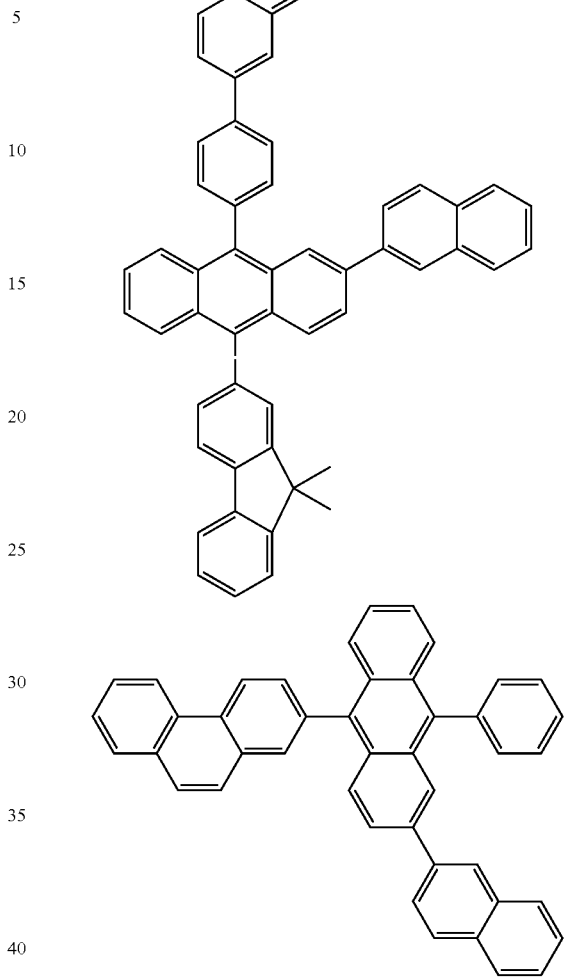

Also, the host may be an anthracene-based compound represented by Formula 401 below.

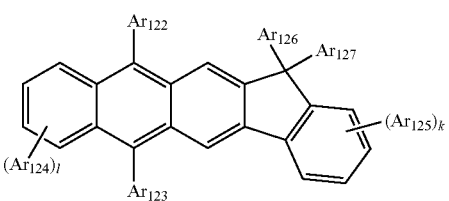

Formula 401

In Formula 401, $Ar_{122}$ through $Ar_{125}$ are the same as defined above in the description of $Ar_{113}$ of Formula 400.

In Formula 401, $Ar_{126}$ and $Ar_{127}$ may be each independently a $C_1$-$C_{10}$ alkyl group (for example, a methyl group, an ethyl group, or a propyl group).

In Formula 401, k and l may be each independently an integer of 0 to 4. For example, k and l may be each independently 0, 1, or 2.

For example, the anthracene-based compound of Formula 401 may be one of the following compounds, but is not limited thereto.

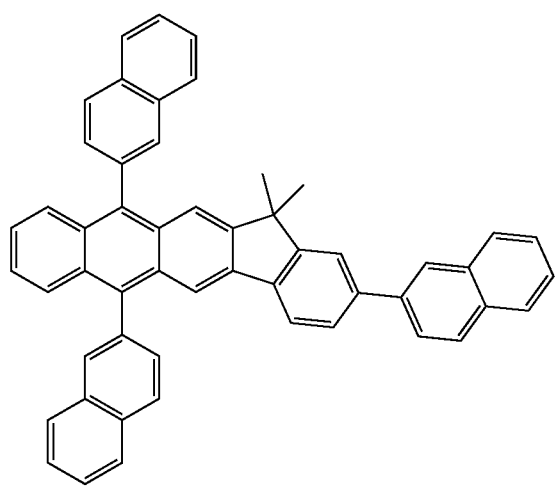
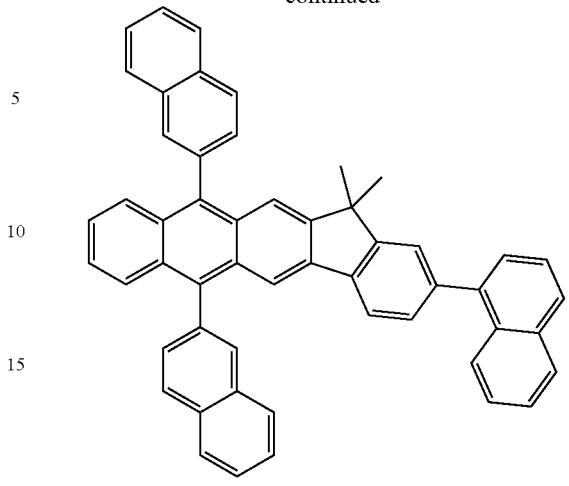
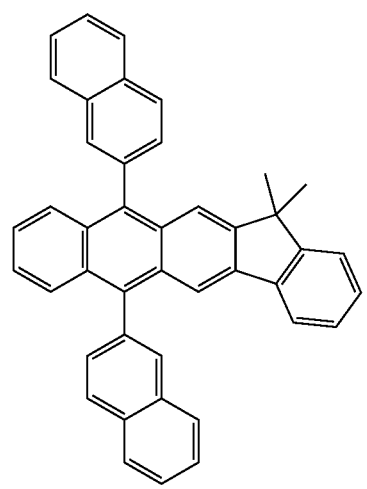
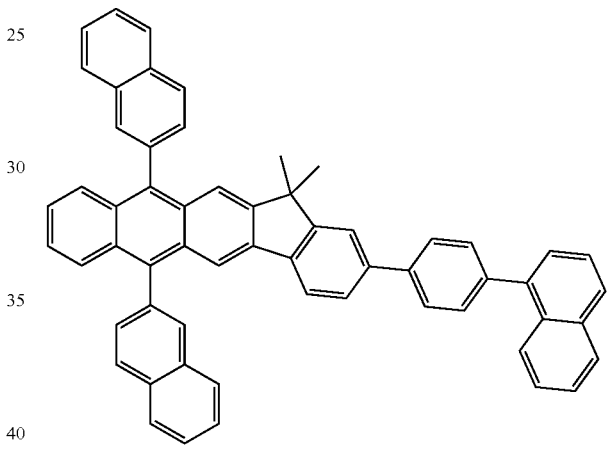
When the OLED is a full-color OLED, the EML may be patterned into a red EML, a green EML, and a blue EML.
At least one of the red EML, the green EML, or the blue EML may include one of the following dopants (ppy=phenylpyridine).
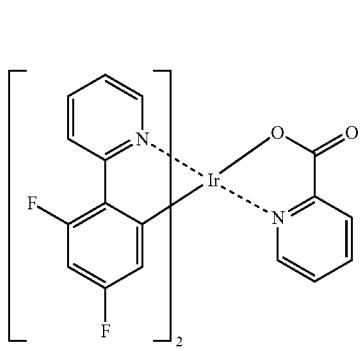
F2Irpic
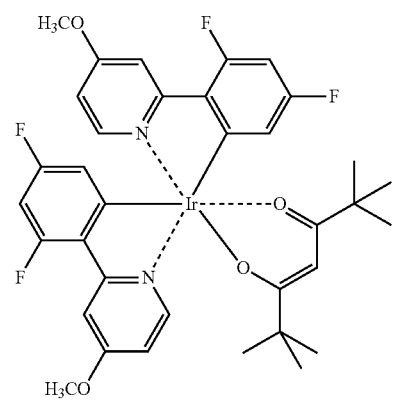
(F2ppy)2Ir(tmd)
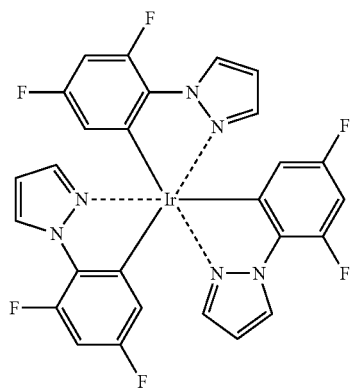
Ir(dfppz)$_3$

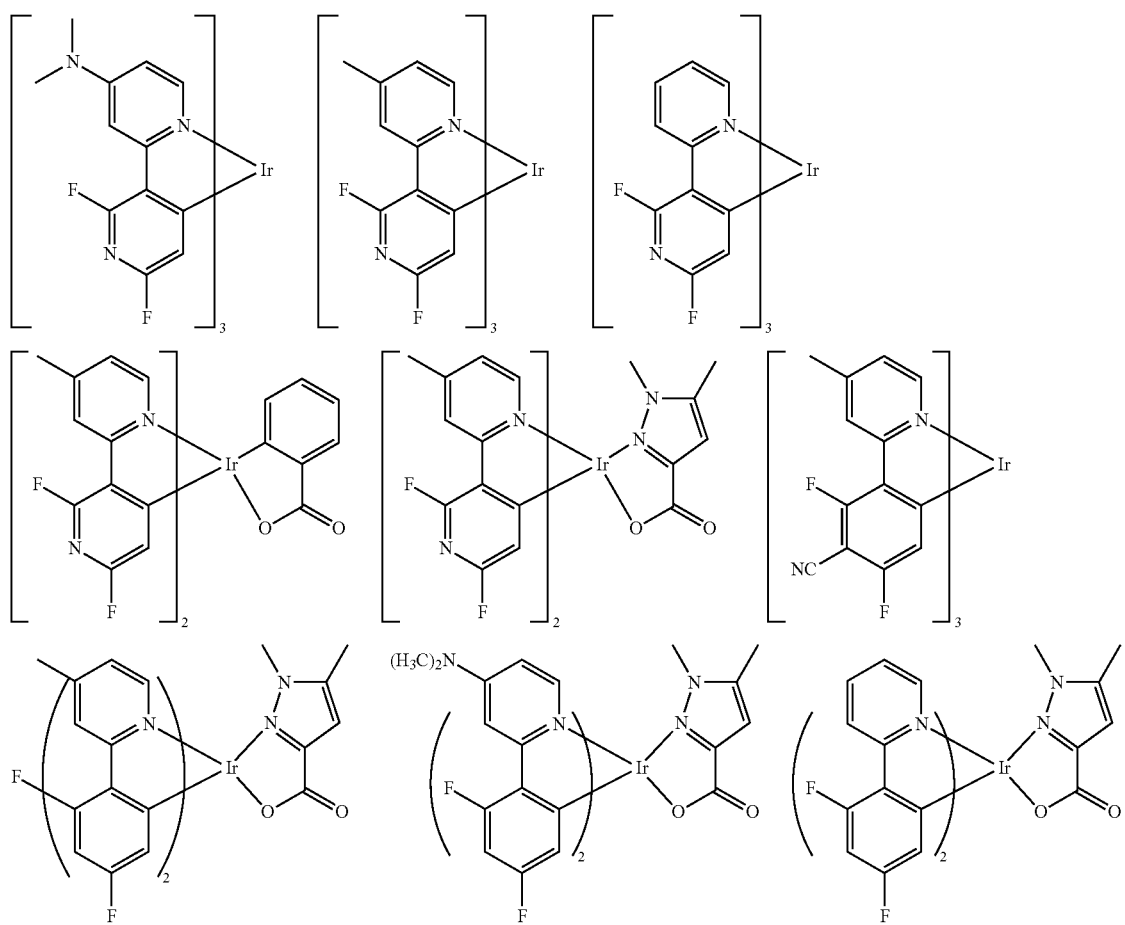
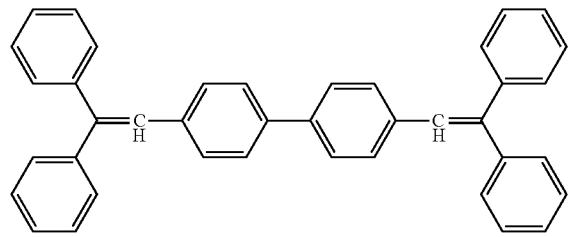
DPVBi
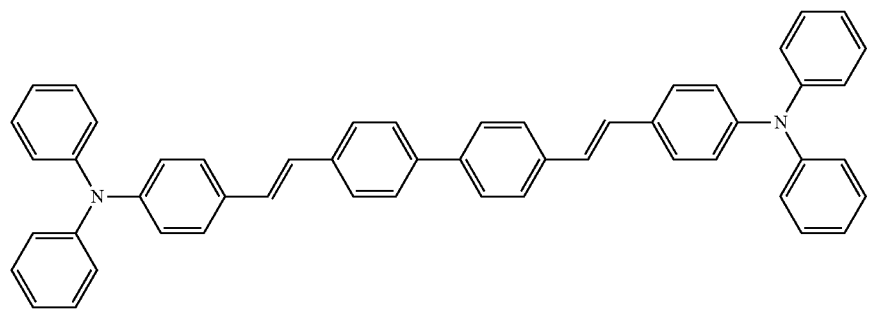
DPAVBi

Examples of a red dopant include, but are not limited to, the following compounds.
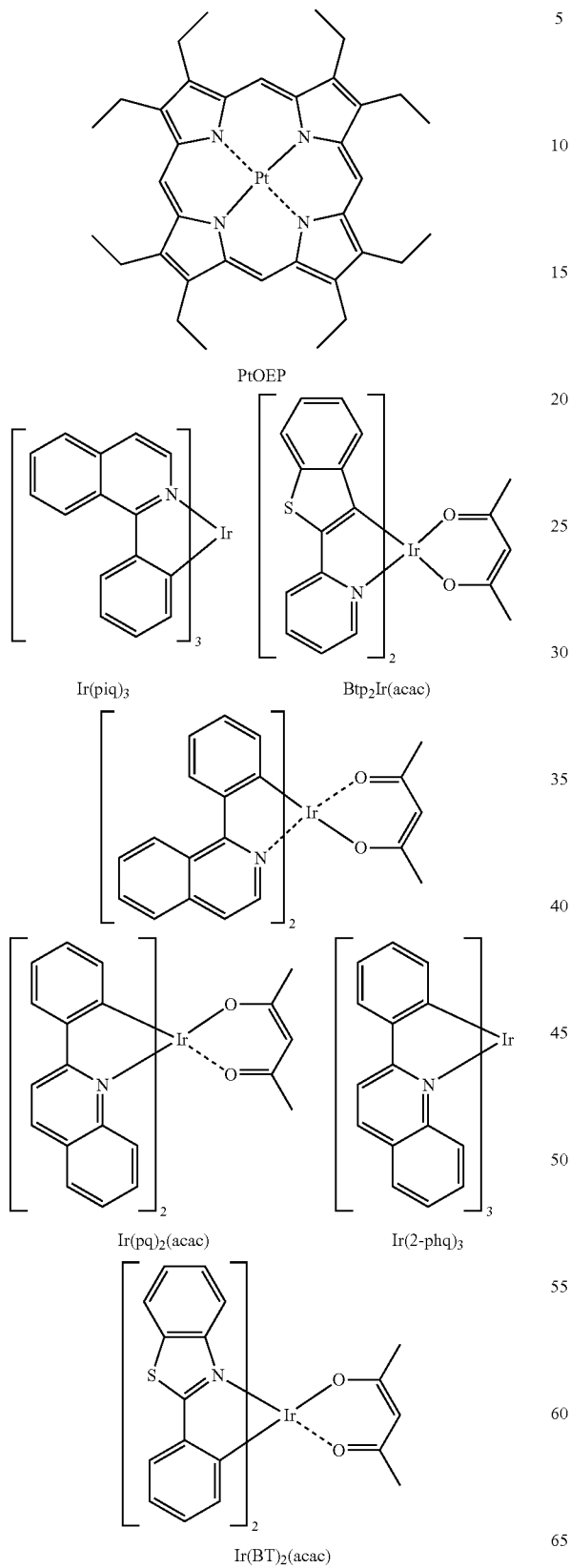
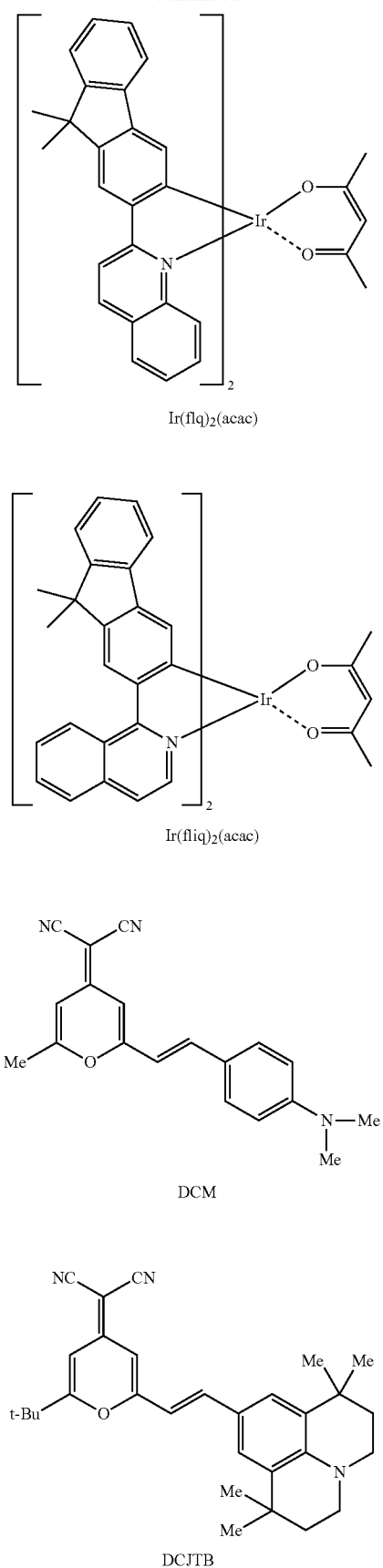

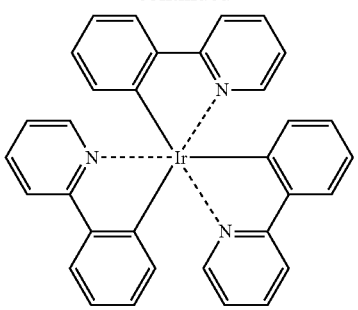
Ir(ppy)₃
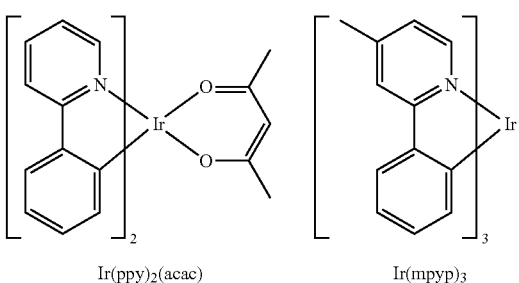
Ir(ppy)₂(acac)  Ir(mpyp)₃
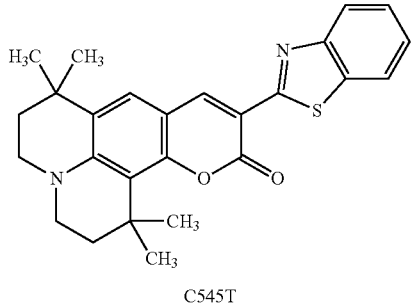
C545T
Examples of a green dopant include, but are not limited to, the following compounds.
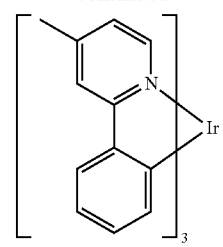
Ir(ppy)₃
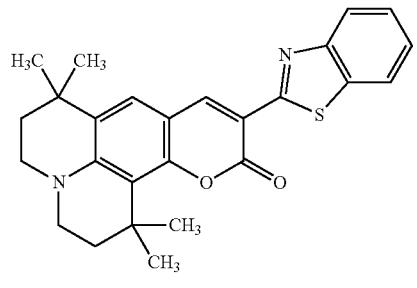
Ir(ppy)₂(acac)
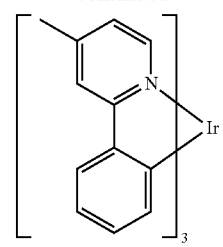
Ir(mpyp)₃
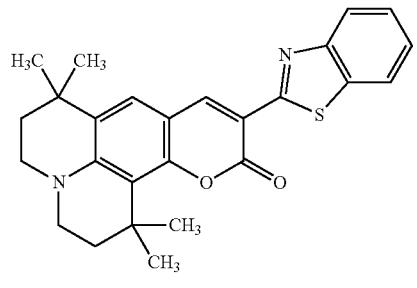
C545T
The dopant included in the EML may be a Pt-complex as described below, but is not limited thereto.
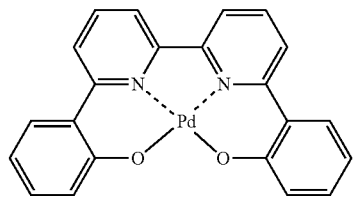
D1
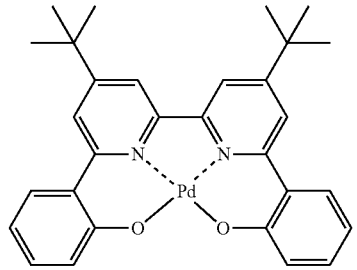
D2
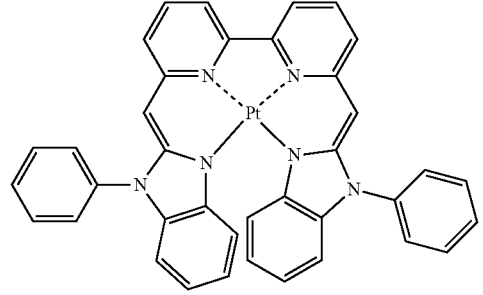
D3

-continued
D4
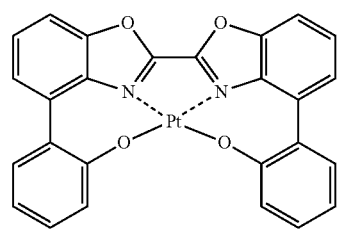
D5
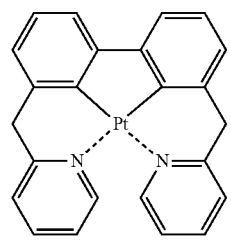
D6
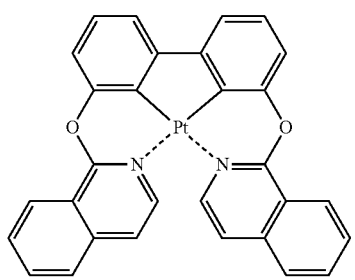
D7
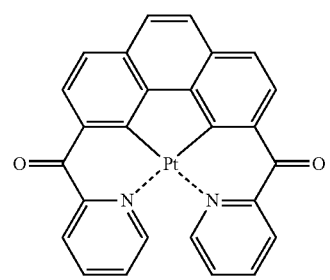
D8
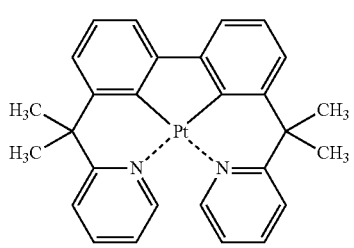
D9
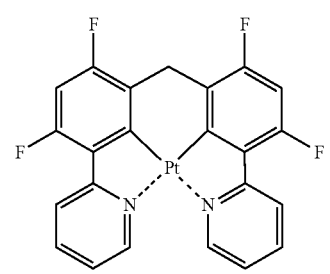
-continued
D10
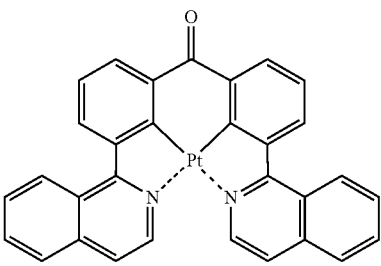
D11
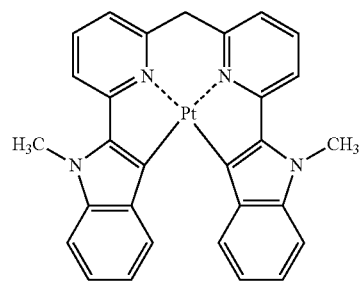
D12
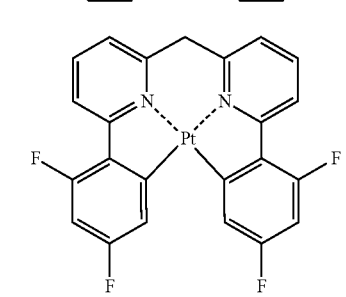
D13
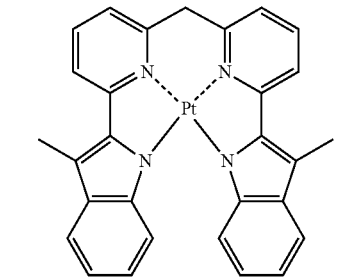
D14
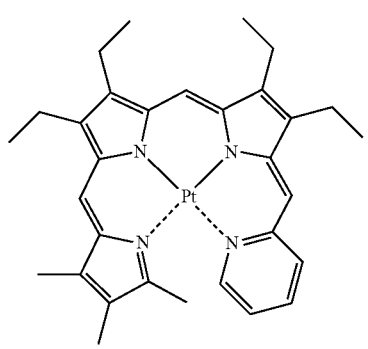

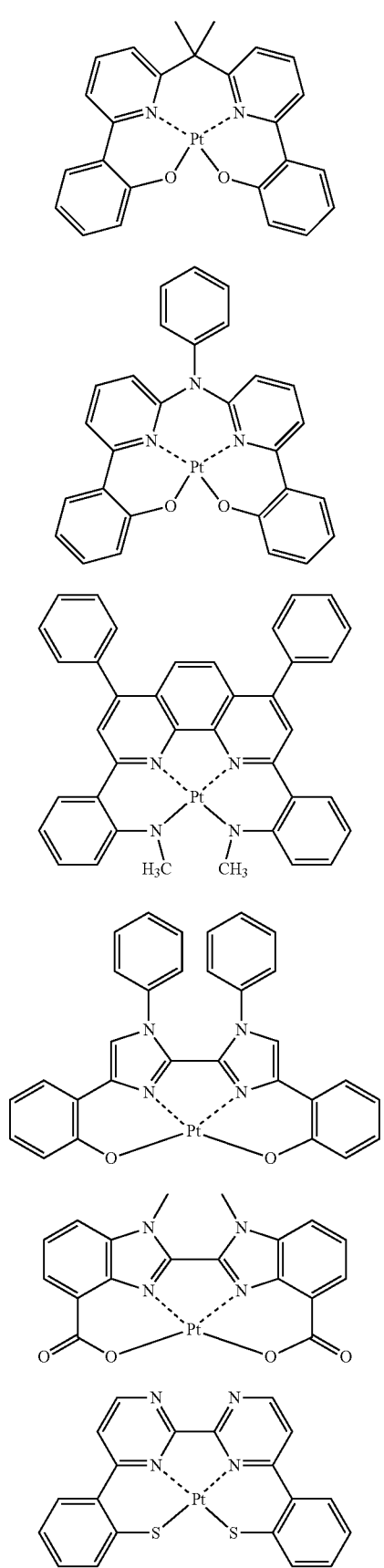

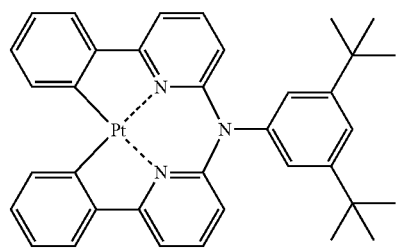
D26
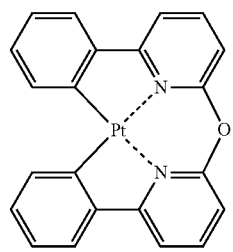
D27
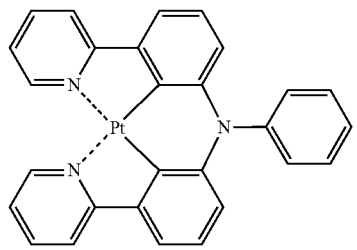
D28
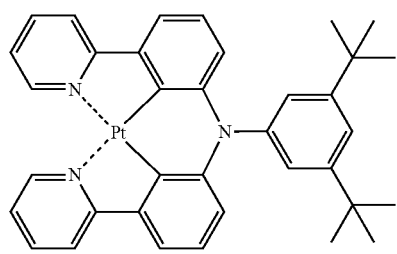
D29
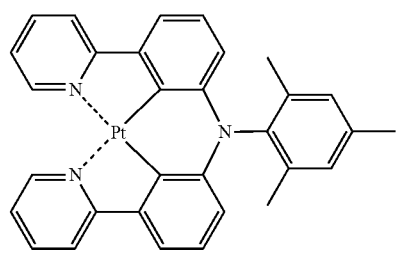
D30
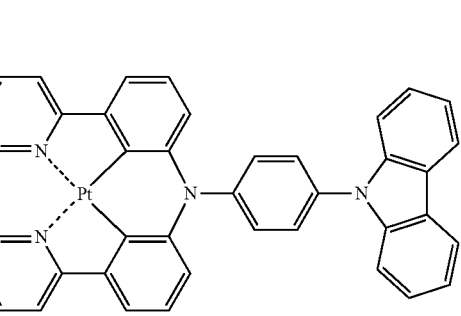
D31
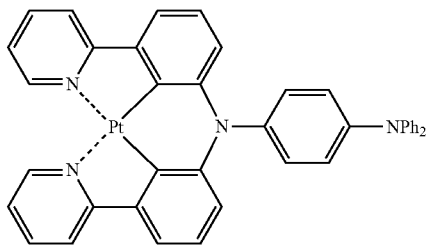
D32
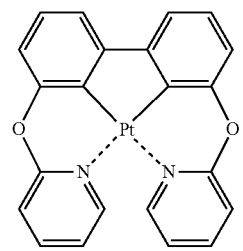
D33
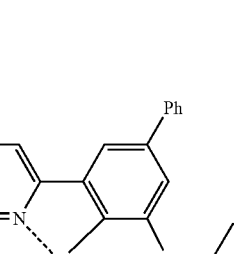
D34
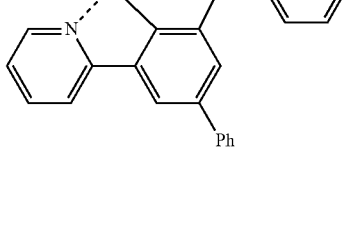
D34
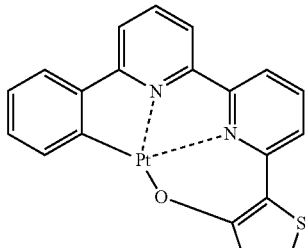
D35
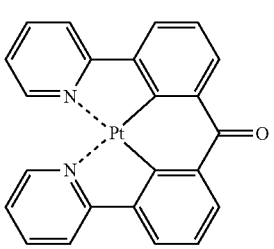
D36

-continued
D37 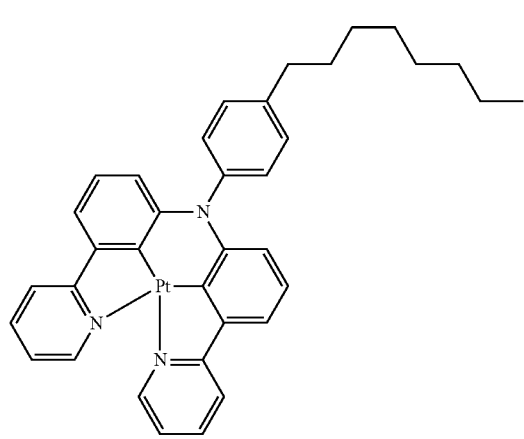
D38 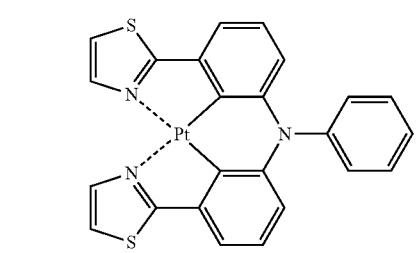
D39 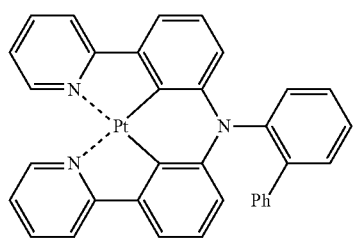
D40 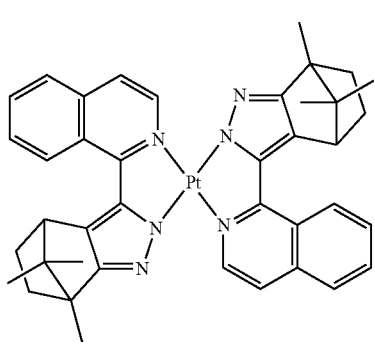
D41 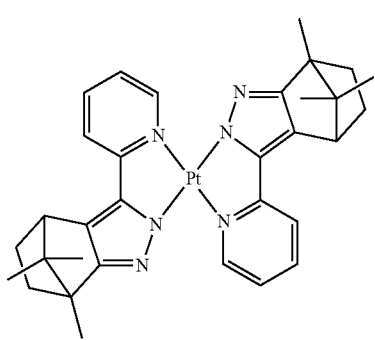
-continued
D42 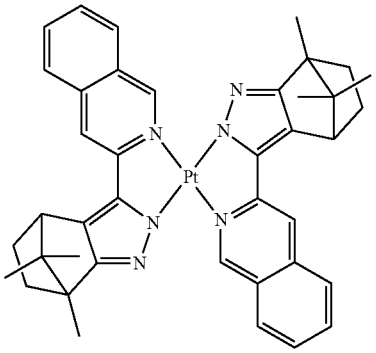
D43 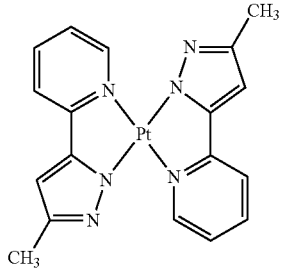
D44 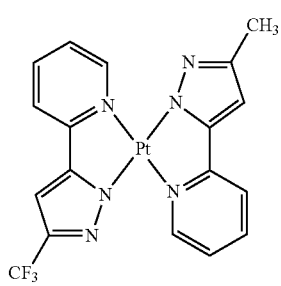
D45 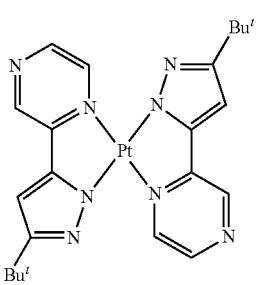
D46 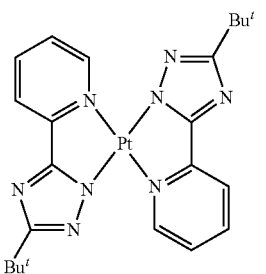

-continued

D47
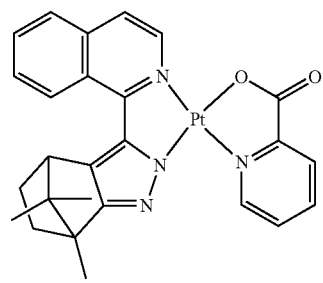

D48
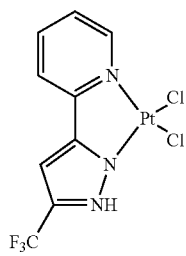

D49
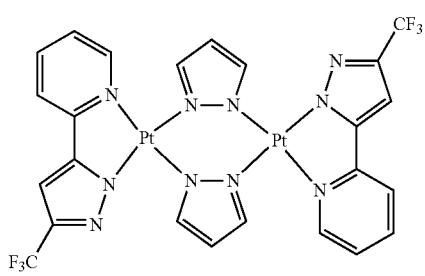

D50
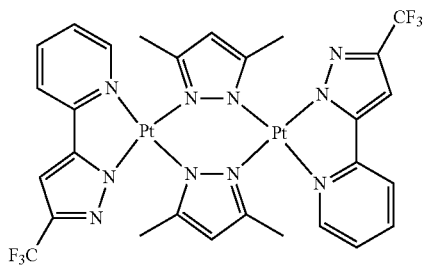

Also, the dopant included in the EML may be an Os-complex as described below, but is not limited thereto.

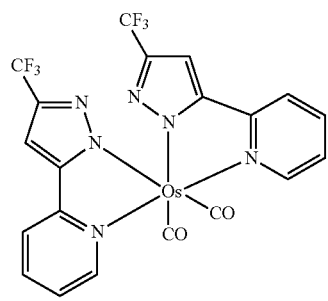

Os(fppz)$_2$(CO)$_2$

-continued

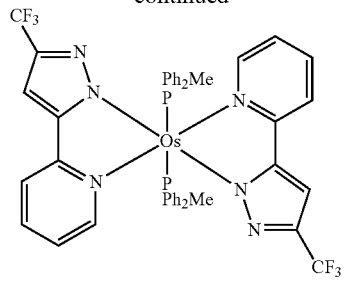

Os(fppz)$_2$(PPh$_2$Me)$_2$

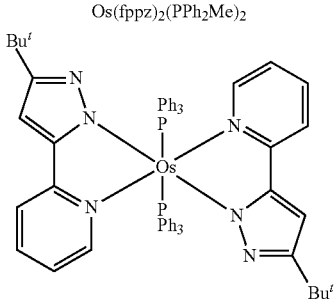

Os(bppz)$_2$(PPh$_3$)$_2$

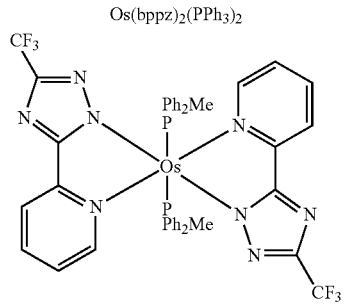

Os(fptz)$_2$(PPh$_2$Me)$_2$

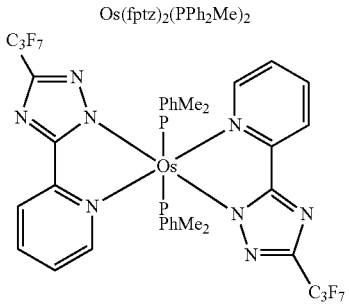

Os(hptz)$_2$(PPhMe$_2$)$_2$

When the EML includes a host and a dopant, the amount of the dopant may be generally about 0.01 to about 15 parts by weight based on 100 parts by weight of the host, but is not limited thereto.

The thickness of the EML may be about 100 Å to about 1,000 Å. In some embodiment, the thickness of the EML may be about 200 Å to about 600 Å. When the thickness of the EML is within these ranges, good luminescent properties may be obtained without a substantial increase in driving voltage.

Next, the ETL is formed on the EML by various methods, such as vacuum deposition, spin coating, or casting. When the ETL is formed by vacuum deposition or spin coating, the deposition or coating conditions may vary according to the compounds used. However, in general, the deposition and coating conditions may be similar or identical to the conditions for forming the HIL. The material for forming the ETL may be a known electron transporting material that stably transports electrons injected from a cathode. Examples of the electron transporting materials may include, but are not limited to, a quinoline derivative such as tris(8-quinolinolate)aluminum (Alq₃), TAZ, Balq, beryllium bis(benzoquinolin-10-olate) (Bebq₂), ADN, Compound 201 below, and Compound 202 below.

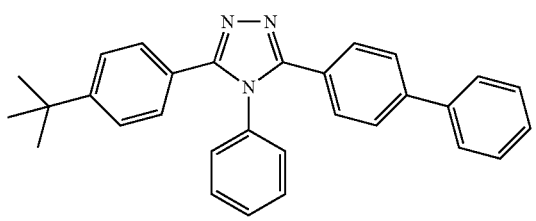

TAZ

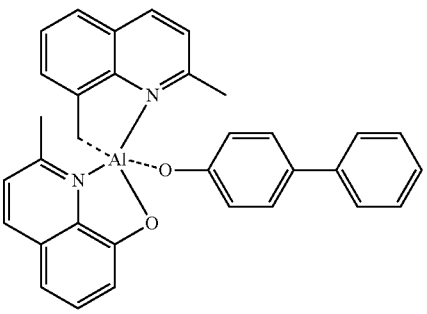

BAlq

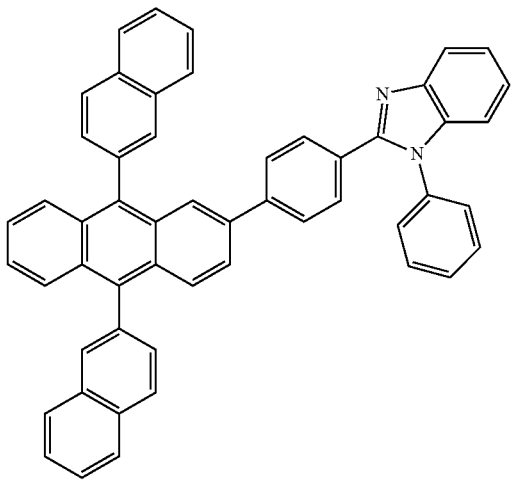

Compound 201

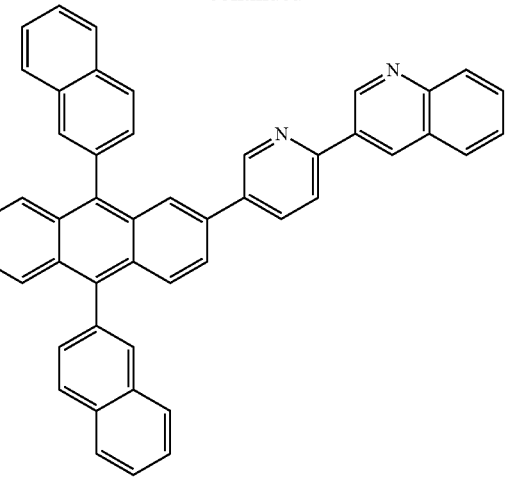

Compound 202

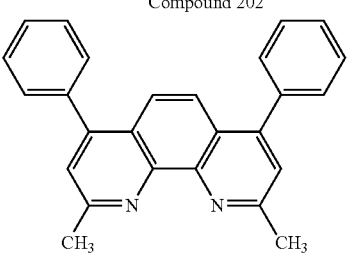

BCP

The thickness of the ETL may be about 100 Å to about 1,000 Å. In some embodiments, the thickness of the ETL may be about 150 Å to about 500 Å. When the thickness of the ETL is within these ranges, satisfactory electron transport properties may be obtained without a substantial increase in driving voltage.

The ETL may include a known electron transporting organic compound and a metal-containing material.

The metal-containing material may include a Li-complex. Examples of the Li-complex may include, but are not limited to, lithium quinolate (LiQ) and Compound 203 below.

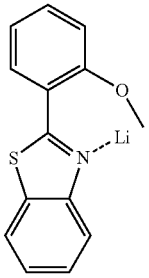

Compound 203

Also, the EIL, which facilitates electron injection from a cathode, may be formed on the ETL, and the material for forming the EIL is not particularly limited.

The material for forming the EIL may include a known material for forming an EIL, such as LiF, NaCl, CsF, Li₂O, or BaO. The deposition conditions of the EIL may vary according to the compound used. However, in general, the conditions may be similar or identical to the conditions for forming the HIL.

The thickness of the EIL may be about 1 Å to about 100 Å. In some embodiments, the thickness of the EIL may be about 3 Å to about 90 Å. When the thickness of the EIL is within these ranges, satisfactory electron injection properties may be obtained without a substantial increase in driving voltage.

The second electrode is formed on these organic layers. The second electrode may be a cathode, which is an electron injection electrode. Here, a metal for forming the second electrode may include a metal having a low work function, such as a metal, an alloy, an electrically conducting compound, or a mixture thereof. In particular, the second electrode may be formed as a thin film of lithium (Li), magnesium (Mg), aluminum (Al), aluminum-lithium (Al—Li), calcium (Ca), magnesium-indium (Mg—In), or magnesium-silver (Mg—Ag), thus being transparent. In order to obtain a top-emission type OLED, the second electrode may be formed as a transparent electrode using ITO or IZO.

The OLED has been described with reference to FIG. 1, but is not limited thereto.

In addition, when the EML includes a phosphorescent dopant, a HBL may be formed between the HTL and the EML or between the H-functional layer and the EML using various methods, such as vacuum deposition, spin coating, casting, or LB deposition in order to prevent triplet excitons or holes from diffusing into the ETL. When the HBL is formed by vacuum deposition or spin coating, the deposition or coating conditions may vary according to the compound used. However, in general, the deposition or coating conditions may be similar or identical to the conditions for forming the HIL. A material for forming the HBL may be a known hole blocking material, such as an oxadiazole derivative, a triazole derivative, or a phenanthroline derivative. For example, the material for forming the HBL may be BCP below.

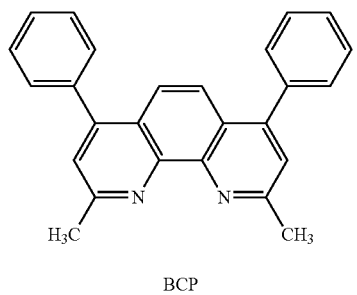 [SMILES: Cc1cc(-c2ccccc2)c2ccc3c(-c4ccccc4)cc(C)nc3c2n1 ; "BCP"]

BCP

The thickness of the HBL may be about 20 Å to about 1,000 Å, for example, about 30 Å to about 300 Å. When the thickness of the HBL is within these ranges, satisfactory hole blocking properties may be obtained without a substantial increase in driving voltage.

The OLED may be used in various types of flat panel display devices, for example, passive matrix OLEDs and active matrix OLEDs. In particular, in an active matrix OLED, a first electrode formed on the substrate side, which is a pixel electrode, may be electrically connected to a source electrode or a drain electrode of a thin film transistor. Also, the OLED may be used in a dual-screen flat panel display device.

The organic layer of the OLED may be formed using a compound of Formula 1 according to an embodiment of the present invention by deposition, or using a compound of Formula 1 according to an embodiment of the present invention prepared in a liquid state using a wet process.

OLEDs according to embodiments of the present invention will now be described with reference to the following Synthesis Examples and Examples. These Examples are presented for illustrative purposes only and are not intended to limit the scope of the invention.

EXAMPLES

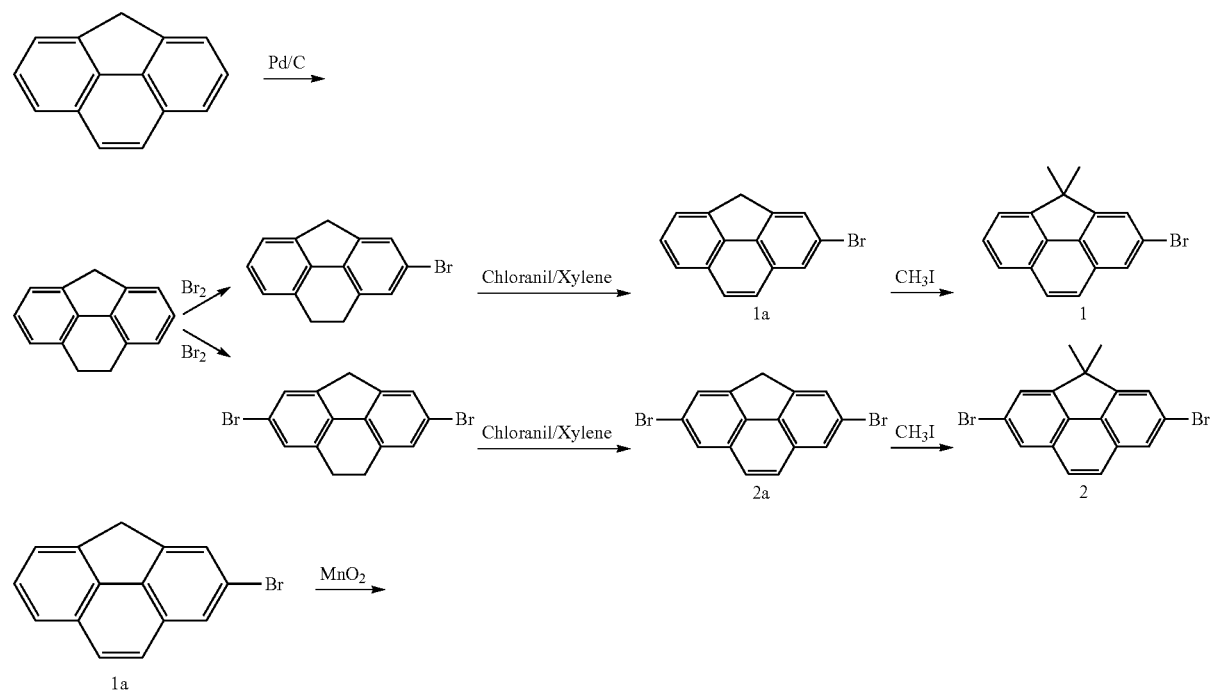

-continued

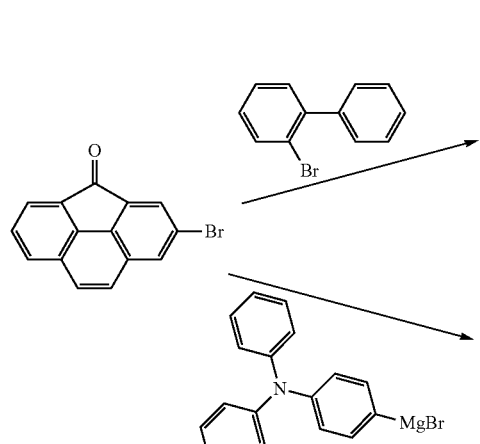
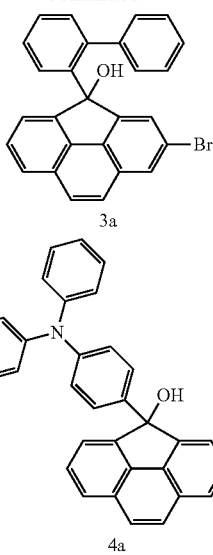
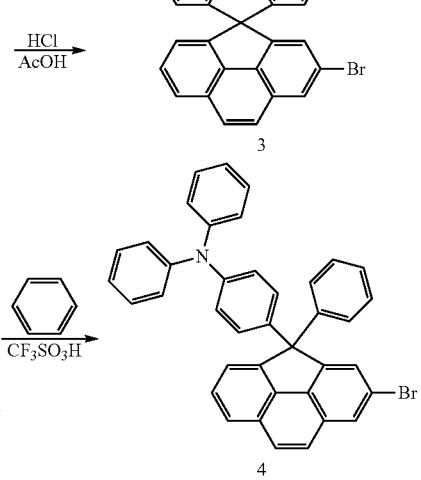

Synthesis Example

Intermediate 1

1) Synthesis of 8,9-dihydro-4H-cyclopenta[def]phenanthrene 10.0 g (52.6 mmol) of 4H-cyclopenta[def]phenanthrene and 8.40 g of 5% Pd/C were dissolved in 70 ml of EtOH in a Par reactor bottle, and the resultant solution was stirred at room temperature for 24 hours with hydrogen pressure being maintained at 40 psi. After the reaction was completed, the reaction solution was filtered and the solvent was evaporated therefrom to obtain 8.60 g of white target material (yield: 85.0%).

2) Synthesis of 2-bromo-8,9-dihydro-4H-cyclopenta[def]phenanthrene 8.5 g (44.2 mmol) of 8,9-dihydro-4H-cyclopenta[def] phenanthrene was dissolved in 80 ml of $CCl_4$, and 7.1 g (44.2 mmol) of $Br_2$ was then slowly added thereto at 0° C. The reaction solution was stirred at room temperature for 4 hours and a 10% $Na_2SO_3$ solution was added thereto to separate the organic layer. The obtained organic layer was dried with magnesium sulfate, the solvent was evaporated therefrom, and the resultant product was recrystallized with n-hexane. As a result, 9.6 g of the target material was obtained (yield: 80%).

3) Synthesis of Intermediate 1a 9.3 g (34.3 mmol) of 2-bromo-8,9-dihydro-4H-cyclopenta[def]phenanthrene and 8.8 g (36.0 mmol) of o-chloranil were dissolved in 70 ml of Xylene, and the mixture was stirred at 110° C. for 72 hours. Thereafter, the reaction solution was cooled to room temperature, and the solvent was evaporated therefrom to obtain a residue. The residue was purified with silicagel column chromatography to obtain 7.48 g of Intermediate 1a (yield: 81%). The obtained compound was confirmed by $^1$H NMR and mass spectrometry/fast atom bombardment (MS/FAB).

$C_{15}H_9Br$: calc. 267.99. found 267.97
$^1$H NMR ($CDCl_3$, 400 MHz) δ 7.98 (2H, s), 7.79 (2H, s), 7.73 (2H, s), 6.94 (dd, 1H), 4.28 (2H, s)

4) Synthesis of Intermediate 1

7.3 g (27.1 mmol) of Intermediate 1a, 73.2 g (216.8 mmol) of t-BuOK, and 60 ml of HMPA were dissolved in 60 ml of DMSO, and the resultant product was stirred at room temperature for 1 hour. Subsequently, 30.6 g (216.8 mmol) of $CH_3I$ was slowly added to the reaction solution at 0° C., the resultant was stirred for 30 hours, 40 ml of water was added thereto, and the resulting product was extracted three times with 70 ml of methylene chloride. The obtained organic layer was dried with magnesium sulfate, and the solvent was evaporated therefrom to obtain a residue. The residue was purified with silicagel column chromatography to obtain 6.3 g of Intermediate 1 (yield: 78%). The obtained compound was confirmed by $^1$H NMR and MS/FAB.

$C_{17}H_{13}Br$: calc. 296.02. found 296.05
$^1$H NMR ($CDCl_3$, 400 MHz) δ 7.98 (2H, s), 7.79 (2H, s), 7.73 (2H, s), 6.94 (dd, 1H), 1.93 (m, 6H)

Synthesis Example

Intermediate 2

1) Synthesis of 2,6-dibromo-8,9-dihydro-4H-cyclopenta[def]phenanthrene 8.9 g of a target material was obtained (yield: 57%) in the same manner as in 2) of the Synthesis of Intermediate 1, except that the amount of $Br_2$ used was 14.2 g (88.4 mmol).

2) Synthesis of Intermediate 2a 6.8 g of Intermediate 2a was obtained (yield: 80%) in the same manner as in 3) of the Synthesis of Intermediate 1, except that 2,6-dibromo-8,9-dihydro-4H-cyclopenta[def] phenanthrene was used instead of 2-bromo-8,9-dihydro-4H-cyclopenta[def]phenanthrene. The obtained compound was confirmed by $^1$H NMR and MS/FAB.

$C_{15}H_8Br_2$: calc. 345.90. found 345.92

$^1$H NMR (CDCl$_3$, 400 MHz) δ 7.98 (2H, s), 7.79 (2H, s), 7.73 (2H, s), 4.28 (2H, s)

3) Synthesis of Intermediate 2

5.8 g of Intermediate 2 was obtained (yield: 79%) in the same manner as in 4) of the Synthesis of Intermediate 1, except that Intermediate 2a was used instead of Intermediate 1a. The obtained compound was confirmed by $^1$H NMR and MS/FAB.

$C_{15}H_8Br_2$: calc. 345.90. found 345.92

$^1$H NMR (CDCl$_3$, 400 MHz) δ 7.98 (2H, s), 7.79 (2H, s), 7.73 (2H, s), 1.93 (s, 6H)

Synthesis Example

Intermediate 3

1) Synthesis of 2-bromo-cyclopenta[def]phenanthren-4-one 7.4 g (27.5 mmol) of Intermediate 1a and 310 g of MnO$_2$ were dissolved in 200 ml of benzene, and the resultant solution was then stirred at 80° C. for 20 hours. The obtained reaction solution was cooled down to room temperature and then filtered to remove MnO$_2$ therefrom, and the filtrate was washed with 50 ml of CHCl$_3$, 50 ml of THF and 50 ml of MeOH in that order. The resultant filtrate was evaporated to obtain a residue. The residue was recrystallized with acetone to obtain 3.74 g of the target material (yield: 48%).

2) Synthesis of Intermediate 3a 3.05 g (13.1 mmol) of 2-bromo biphenyl was dissolved in 50 ml of THF, and 15.4 ml (26.2 mmol) of t-BuLi (1.7M in Pentane) was then slowly added thereto at –78° C. The resultant solution was stirred for 1 hour at –78° C., 3.7 g (13.1 mmol) of 2-bromo-cyclopenta[def]phenanthrene-4-one was slowly added thereto for 30 minutes, and the resultant reaction solution was stirred at –78° C. for 30 minutes and then further stirred at room temperature for 3 hours. Then, 40 ml of water was added to the reaction solution and the resulting reaction solution was extracted three times with 50 ml of ethyl acetate. The obtained organic layer was dried with magnesium sulfate, and the solvent was evaporated therefrom to obtain a residue. The residue was purified with silicagel column chromatography to obtain 5.44 g of Intermediate 3a (yield: 95%).

3) Synthesis of Intermediate 3

5.4 g (12.3 mmol) of Intermediate 3a was dissolved in 50 ml of acetic acid, 3 ml of concentrated hydrochloric acid was then slowly added at 0° C., and the resultant solution was stirred for 2 hours. A white solid obtained during the reaction was filtered and washed with acetic acid and ethanol to obtain 4.70 g of Intermediate 3 (yield: 90%). The obtained compound was confirmed by $^1$H NMR and MS/FAB.

$C_{27}H_{15}Br$: calc. 418.04. found 418.05

$^1$H NMR (CDCl$_3$, 400 MHz) δ 7.22-7.26 (m, 8H), 7.70 (s, 2H), 7.80 (s, 2H), 8.00 (s, 2H)

Synthesis Example

Intermediate 4

Synthesis of Intermediate 4a 3.7 g (13.1 mmol) of 2-bromo-cyclopenta[def]phenanthrene-4-one was dissolved in 50 ml of ether and 20 ml of THF, 4.55 g (13.1 mmol) of (4-(diphenylamino)-phenyl)-magnesium bromide was then slowly added thereto, and the resultant solution was stirred at 80° C. for 3 hours. The reaction solution was cooled down to room temperature, 30 ml of water was added thereto, the pH of the reaction solution was adjusted to 3 to 4 using a 1N HCl solution, and the resultant reaction solution was extracted three times with 50 ml of ethyl acetate. The obtained organic layer was dried with magnesium sulfate, and the solvent was evaporated therefrom to obtain a residue. The residue was purified with silicagel column chromatography to obtain 4.98 g of Intermediate 4a (yield: 72%).

Synthesis of Intermediate 4

4.98 g (9.43 mmol) of Intermediate 4a was dissolved in 50 ml of benzene, 2.52 mL (28.3 mmol) of trifluoromethane sulfonic acid was then slowly added thereto, and the resultant solution was stirred at 80° C. for 2 hours. Then, the reaction solution was cooled down to room temperature, 40 ml of water was added to the reaction solution, and the resulting reaction solution was extracted three times with 50 ml of ethyl acetate. The obtained organic layer was dried with magnesium sulfate, and the solvent was evaporated therefrom to obtain a residue. The residue was recrystallized with ethyl acetate-hexane to obtain 3.9 g of Intermediate 4 (yield: 70%). The obtained compound was confirmed by $^1$H NMR and MS/FAB.

$C_{39}H_{26}BrN$: calc. 587.12. found 587.12

$^1$H NMR (CDCl$_3$, 400 MHz) δ 7.97 (s, 1H), 7.84 (d, 1H), 7.79-7.78 (m, 2H), 7.63 (d, 1H), 7.51 (d, 1H), 7.41-7.35 (m, 2H), 7.28-7.18 (m, 7H), 7.02-6.98 (m, 2H), 6.88-6.85 (m, 2H), 6.66-6.61 (m, 3H), 6.51-6.48 (m, 4H)

Synthesis Examples

1) Synthesis of Compound 1

4.5 g (15.1 mmol) of Intermediate 1, 6.40 g (16.6 mmol) of bis-biphenyl-4-yl-amine, 0.28 g (0.3 mmol) of Pd$_2$(dba)$_3$, 0.06 g (0.3 mmol) of P(tBu)$_3$, and 2.18 g (22.7 mmol) of NaOtBu were dissolved in 70 ml of toluene, and the resultant solution was then stirred at 80° C. for 4 hours. Then, the reaction solution was cooled down to room temperature, 40 ml of water was added to the reaction solution, and the resulting reaction solution was extracted three times with 50 ml of ethyl acetate. The obtained organic layer was dried with magnesium sulfate, and the solvent was evaporated therefrom to obtain a residue. The residue was purified with silicagel column chromatography to obtain 6.10 g of Compound 1 (yield: 75%). The obtained compound was confirmed by $^1$H NMR and MS/FAB.

$C_{41}H_{31}N$: calc. 537.25. found 537.23

$^1$H NMR (CDCl$_3$, 400 MHz) δ 7.93 (d, 1H), 7.86 (d, 1H), 7.84-7.81 (m, 5H), 7.73-7.64 (m, 9H), 7.62-7.58 (m, 2H), 7.51 (t, 1H), 7.53 (d, 1H), 6.92 (d, 1H), 6.73-6.70 (m, 4H), 1.92 (s, 6H)

2) Synthesis of Compound 4

5.45 g of Compound 4 was obtained (yield: 72%) in the same manner as in the Synthesis of Compound 1, except that (9,9-dimethyl-9H-fluorene-2-yl)-phenyl-amine was used instead of bis-biphenyl-4-yl-amine. The obtained compound was confirmed by $^1$H NMR and MS/FAB.

$C_{38}H_{31}N$: calc. 501.25. found 501.25

$^1$H NMR (CDCl$_3$, 400 MHz) δ 7.97 (d, 1H), 7.92 (d, 1H), 7.86 (d, 1H), 7.84-7.80 (m, 2H), 7.67 (d, 1H), 7.56-7.49 (m, 2H), 7.43 (d, 1H), 7.34-7.26 (m, 4H), 6.95-6.84 (m, 3H), 6.68 (d, 1H), 6.53-6.50 (m, 2H), 1.93 (s, 6H), 1.63 (s, 6H)

3) Synthesis of Compound 6

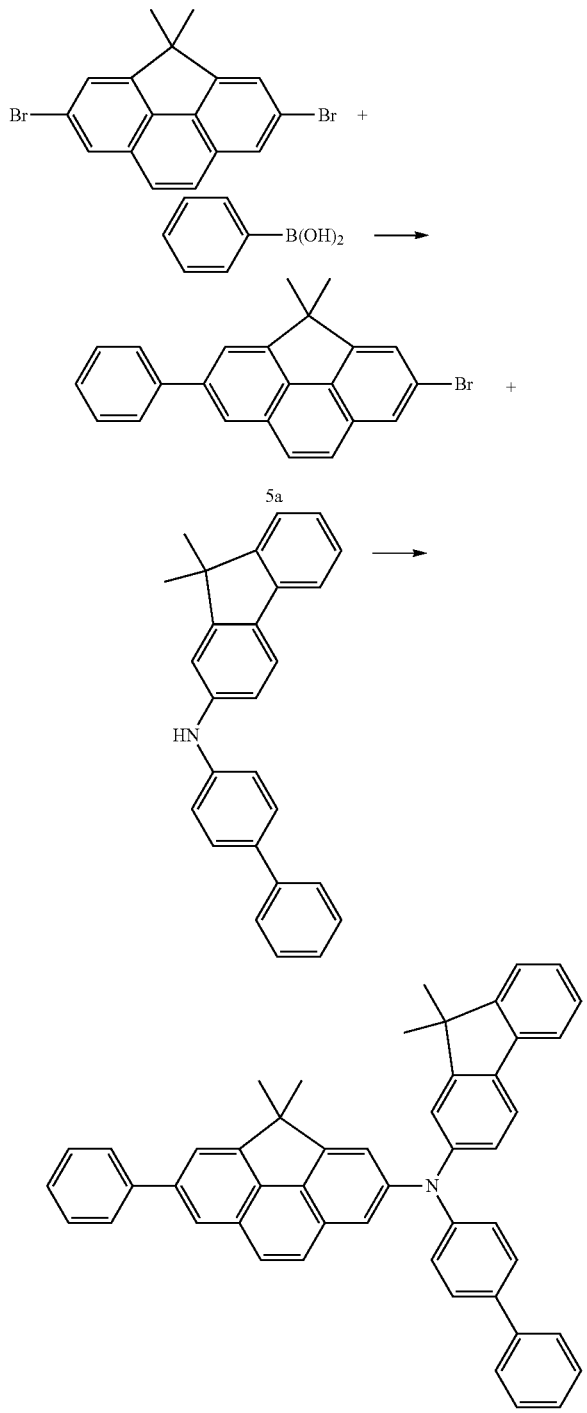

5.5 g (14.6 mmol) of Intermediate 2, 1.78 g (14.6 mmol) of phenylboronic acid, 0.84 g (0.73 mmol) of Pd(PPh$_3$)$_4$, and 6.05 g (43.8 mmol) of K$_2$CO$_3$ were dissolved in 60 ml of THF and 40 ml of H$_2$O, and the resultant solution was then stirred at 80° C. for 24 hours. Then, the reaction solution was cooled down to room temperature, 40 ml of water was added to the reaction solution, and the resulting reaction solution was extracted three times with 50 ml of ethyl acetate. The obtained organic layer was dried with magnesium sulfate, and the solvent was evaporated therefrom to obtain a residue. The residue was purified with silicagel column chromatography to obtain 3.92 g of Intermediate 5a (yield: 72%). 3.9 g (10.4 mmol) of Intermediate 5a, 3.78 g (10.4 mmol) of biphenyl-4-yl-(9,9-dimethyl-9H-fluorene-2-yl)-amine, 0.19 g (0.21 mmol) of Pd$_2$(dba)$_3$, 0.04 g (0.21 mmol) of P(tBu)$_3$, and 1.50 g (15.6 mmol) of NaOtBu were dissolved in 60 ml of toluene, and the resultant solution was then stirred at 80° C. for 3 hours. Then, the reaction solution was cooled down to room temperature, 30 ml of water was added to the reaction solution, and the resulting reaction solution was extracted three times with 50 ml of ethyl acetate. The obtained organic layer was dried with magnesium sulfate, and the solvent was evaporated therefrom to obtain a residue. The residue was purified with silicagel column chromatography to obtain 5.24 g of Compound 6 (yield: 77%). The obtained compound was confirmed by $^1$H NMR and MS/FAB.

C$_{50}$H$_{39}$N: calc. 653.31. found 653.32
$^1$H NMR (CDCl$_3$, 400 MHz) δ 8.19 (d, 1H), 7.97 (d, 1H), 7.90-7.88 (m, 2H), 7.85-7.79 (m, 3H), 7.73-7.58 (m, 10H), 7.55-7.51 (m, 2H), 7.47 (d, 1H), 7.34-7.30 (m, 2H), 6.94-6.90 (m, 2H), 6.68-6.65 (m, 3H), 1.93 (s, 6H), 1.65 (s, 6H)

4) Synthesis of Compound 7

6.54 g of Compound 7 was obtained (yield: 69%) in the same manner as in the Synthesis of Compound 1, except that (9,9-dimethyl-9H-fluorene-2-yl)-(4-naphthalene-1-yl-phenyl)-amine was used instead of bis-biphenyl-4-yl-amine. The obtained compound was confirmed by $^1$H NMR and MS/FAB.

C$_{48}$H$_{37}$N: calc. 627.29. found 627.30
$^1$H NMR (CDCl$_3$, 400 MHz) δ 8.03-8.00 (m, 2H), 7.97 (d, 1H), 7.91 (d, 1H), 7.86 (d, 1H), 7.84-7.79 (m, 3H), 7.72-7.63 (m, 5H), 7.57-7.49 (m, 2H), 7.45-7.41 (m, 2H), 7.35-7.32 (m, 2H), 7.17 (t, 1H), 6.97 (d, 1H), 6.93 (d, 1H), 6.70 (d, 1H), 6.56 (m, 2H), 1.92 (s, 6H), 1.63 (s, 6H)

5) Synthesis of Compound 8

6.72 g of Compound 8 was obtained (yield: 77%) in the same manner as in the Synthesis of Compound 1, except that biphenyl-3-yl-(9,9-dimethyl-9H-fluorene-2-yl)-amine was used instead of bis-biphenyl-4-yl-amine. The obtained compound was confirmed by $^1$H NMR and MS/FAB.

C$_{44}$H$_{35}$N: calc. 577.28. found 577.25
$^1$H NMR (CDCl$_3$, 400 MHz) δ 7.98 (d, 1H), 7.93 (d, 1H), 7.87 (d, 1H), 7.84-7.77 (m, 4H), 7.68 (d, 1H), 7.66-7.59 (m, 3H), 7.55-7.49 (m, 2H), 7.46-7.42 (m, 2H), 7.34-7.28 (m, 3H), 7.14 (t, 1H), 6.97 (d, 1H), 6.91 (d, 1H), 6.83 (d, 1H), 6.47 (d, 1H), 1.92 (s, 6H), 1.64 (s, 6H)

6) Synthesis of Compound 9

6.33 g of Compound 9 was obtained (yield: 67%) in the same manner as in the Synthesis of Compound 1, except that (9,9-diphenyl-9H-fluorene-2-yl)-phenyl-amine was used instead of bis-biphenyl-4-yl-amine. The obtained compound was confirmed by $^1$H NMR and MS/FAB.

$C_{48}H_{35}N$: calc. 628.80. found 628.81

$^1$H NMR (CDCl$_3$, 400 MHz) δ 8.07 (d, 1H), 7.93 (d, 1H), 7.87 (d, 1H), 7.83 (d, 1H), 7.67-7.62 (m, 2H), 7.53 (d, 2H), 7.48 (d, 1H), 7.40-7.27 (m, 13H), 7.00 (d, 1H), 6.93 (d, 1H), 6.85 (t, 1H), 6.78 (d, 1H), 6.74 (d, 1H), 6.48-6.45 (m, 2H), 1.93 (s, 6H)

7) Synthesis of Compound 10

6.50 g of Compound 10 was obtained (yield: 69%) in the same manner as in the Synthesis of Compound 1, except that (9,9-spiro-fluorene-2-yl)-phenyl-amine was used instead of bis-biphenyl-4-yl-amine. The obtained compound was confirmed by $^1$H NMR and MS/FAB.

$C_{48}H_{33}N$: calc. 623.78. found 623.80

$^1$H NMR (CDCl$_3$, 400 MHz) δ 8.05 (d, 1H), 7.99 (d, 2H), 7.83 (d, 1H), 7.79 (d, 1H), 7.73 (d, 2H), 7.67-7.61 (m, 4H), 7.53-7.51 (m, 1H), 7.43 (d, 1H), 7.41-7.35 (m, 4H), 7.31-7.26 (m, 2H), 7.01-6.93 (m, 6H), 6.85 (t, 1H), 6.52-6.49 (m, 2H), 1.93 (s, 6H)

8) Synthesis of Compound 16

7.51 g of Compound 16 was obtained (yield: 72%) in the same manner as in the Synthesis of Compound 1, except that Intermediate 3 was used instead of Intermediate 1, and (4-fluo-phenyl)-(9-phenyl-9H-carbazole-3-yl)-amine was used instead of bis-biphenyl-4-yl-amine. The obtained compound was confirmed by $^1$H NMR and MS/FAB.

$C_{51}H_{31}FN_2$: calc. 690.25. found 690.23

$^1$H NMR (CDCl$_3$, 400 MHz) δ 8.21 (d, 1H), 8.07 (d, 2H), 7.93 (d, 1H), 7.85 (d, 1H), 7.81 (d, 1H), 7.74-7.69 (m, 5H), 7.66-7.55 (m, 4H), 7.52-7.47 (m, 6H), 7.25-7.19 (m, 2H), 7.11 (d, 1H), 6.91 (d, 2H), 6.85-6.80 (m, 4H), 6.53 (t, 1H)

9) Synthesis of Compound 17

7.05 g of Compound 17 was obtained (yield: 69%) in the same manner as in the Synthesis of Compound 1, except that biphenyl-4-yl-(9-naphthalene-1-yl-9H-carbazole-3-yl)-amine was used instead of bis-biphenyl-4-yl-amine. The obtained compound was confirmed by $^1$H NMR and MS/FAB.

$C_{51}H_{36}N_2$: calc. 676.29. found 676.30

$^1$H NMR (CDCl$_3$, 400 MHz) δ 8.23 (d, 1H), 8.06 (d, 1H), 7.91 (d, 1H), 7.84 (d, 1H), 7.78 (d, 1H), 7.72-7.65 (m, 5H), 7.61 (d, 1H), 7.55-7.47 (m, 7H), 7.43-7.25 (m, 7H), 7.16 (d, 1H), 7.05 (d, 1H), 6.98 (d, 1H), 6.81-6.77 (m, 2H), 1.92 (s, 6H)

10) Synthesis of Compound 18

6.82 g of Compound 18 was obtained (yield: 63%) in the same manner as in the synthesis of Compound 1, except that (9,9-dimethyl-9H-fluorene-2-yl)-(7-phenyl-7H-benzo[c]carbazole-10-yl)-amine was used instead of bis-biphenyl-4-yl-amine. The obtained compound was confirmed by $^1$H NMR and MS/FAB.

$C_{54}H_{40}N_2$: calc. 716.32. found 716.33

$^1$H NMR (CDCl$_3$, 400 MHz) δ 8.28 (d, 1H), 8.15 (d, 1H), 8.07 (d, 1H), 7.91 (d, 1H), 7.85 (d, 1H), 7.80-7.76 (m, 3H), 7.71-7.65 (m, 4H), 7.61-7.56 (m, 5H), 7.49-7.38 (m, 4H), 7.33 (d, 1H), 7.25-7.21 (m, 2H), 7.05-7.00 (m, 2H), 6.94 (d, 1H), 6.86 (d, 1H), 1.93 (s, 6H), 1.63 (s, 6H)

11) Synthesis of Compound 21

4.71 g of Compound 21 was obtained (yield: 70%) in the same manner as in the Synthesis of Compound 1, except that Intermediate 4 was used instead of Intermediate 1, and naphthalene-1-yl-phenyl-amine was used instead of bis-biphenyl-4-yl-amine. The obtained compound was confirmed by $^1$H NMR and MS/FAB.

$C_{55}H_{38}N_2$: calc. 726.30. found 726.31

$^1$H NMR (CDCl$_3$, 400 MHz) δ 8.11 (d, 1H), 7.92 (d, 1H), 7.80 (d, 1H), 7.72-7.65 (m, 4H), 7.61 (d, 1H), 7.57 (t, 1H), 7.52-7.46 (m, 4H), 7.42-7.31 (m, 8H), 7.16 (d, 1H), 7.02 (d, 1H), 6.98-6.92 (m, 4H), 6.84-6.81 (m, 2H), 6.68-6.63 (m, 3H), 6.57-6.52 (m, 4H), 6.48-6.45 (m, 2H)

12) Synthesis of Compound 22

4.83 g of Compound 22 was obtained (yield: 68%) in the same manner as in the Synthesis of Compound 21, except that (4-(9H-carbazole-9-yl)-phenyl)-magnesium bromide was used instead of (4-(diphenylamino)-phenyl)-magnesium bromide, and biphenyl-4-yl-p-tolyl-amine was used instead of bis-biphenyl-4-yl-amine. The obtained compound was confirmed by $^1$H NMR and MS/FAB.

$C_{58}H_{40}N_2$: calc. 764.32. found 764.33

$^1$H NMR (CDCl$_3$, 400 MHz) δ 8.11 (d, 2H), 7.91 (d, 1H), 7.84-7.82 (m, 2H), 7.78 (d, 1H), 7.73-7.65 (m, 5H), 7.62-7.45 (m, 7H), 7.41-7.38 (m, 3H), 7.35-7.28 (m, 4H), 7.20-7.18 (m, 2H), 7.04 (d, 1H), 6.83-6.79 (m, 4H), 6.67-6.64 (m, 2H), 6.61-6.57 (m, 3H), 2.30 (s, 3H)

13) Synthesis of Compound 24

4.65 g of Compound 24 was obtained (yield: 76%) in the same manner as in the Synthesis of Compound 21, except that (4-(9-naphthalene-1-yl-10-phenyl-anthracene))-magnesium bromide was used instead of (4-(diphenylamino)-phenyl)-magnesium bromide, and diphenyl-amine was used instead of bis-biphenyl-4-yl-amine. The obtained compound was confirmed by $^1$H NMR and MS/FAB.

$C_{63}H_{41}N$: calc. 811.32. found 811.34

$^1$H NMR (CDCl$_3$, 400 MHz) δ 7.95-7.91 (m, 3H), 7.82-7.75 (m, 5H), 7.64-7.60 (m, 2H), 7.57-7.54 (m, 2H), 7.47-7.38 (m, 5H), 7.32-7.27 (m, 3H), 7.21-7.13 (m, 8H), 7.08 (t, 1H), 6.97 (d, 1H), 6.86 (t, 2H), 6.79-6.75 (m, 2H), 6.66-6.63 (m, 2H), 6.58 (t, 1H), 6.53-6.50 (m, 4H)

14) Synthesis of Compound 25

5.19 g of Compound 25 was obtained (yield: 72%) in the same manner as in the Synthesis of Compound 21, except that (9,9-dimethyl-9H-fluorene-2-yl)-magnesium bromide was used instead of (4-(diphenylamino)-phenyl)-magnesium bromide, and bis-biphenyl-3-yl-amine was used instead of bis-biphenyl-4-yl-amine. The obtained compound was confirmed by $^1$H NMR and MS/FAB.

$C_{60}H_{43}N$: calc. 777.34. found 777.34

$^1$H NMR (CDCl$_3$, 400 MHz) δ 8.02 (d, 1H), 7.89 (d, 1H), 7.82-7.77 (m, 4H), 7.69-7.59 (m, 11H), 7.55-7.51 (m, 2H), 7.46-7.43 (m, 3H), 7.36-7.27 (m, 8H), 7.12 (t, 2H), 6.87 (d, 1H), 6.65 (t, 1H), 6.53-6.50 (m, 2H), 6.35 (d, 1H), 1.52 (s, 6H)

15) Synthesis of Compound 26

5.24 g of Compound 26 was obtained (yield: 70%) in the same manner as in the Synthesis of Compound 21, except that (3-dibenzothienyl)-magnesium bromide was used instead of (4-(diphenylamino)-phenyl)-magnesium bromide, and biphenyl-3-yl-(9,9-dimethyl-9H-fluorene-2-yl)-amine was used instead of bis-biphenyl-4-yl-amine. The obtained compound was confirmed by $^1$H NMR and MS/FAB.

$C_{60}H_{41}NS$: calc. 807.30. found 807.31

¹H NMR (CDCl₃, 400 MHz) δ 8.23 (d, 2H), 7.98 (d, 1H), 7.95-7.90 (m, 2H), 7.85-7.78 (m, 3H), 7.76 (d, 1H), 7.71-7.56 (m, 8H), 7.49-7.46 (m, 1H), 7.42-7.29 (m, 1H), 7.22 (d, 1H), 7.18 (t, 1H), 6.99 (d, 1H), 6.86 (d, 1H), 6.64 (t, 1H), 6.47 (d, 1H), 1.62 (s, 6H)

16) Synthesis of Compound 28

7.07 g of Compound 28 was obtained (yield: 63%) in the same manner as in the Synthesis of Compound 1, except that (9,9-diphenyl-9H-fluorene-2-yl)-[4-(9-phenyl-9H-carbazole-3-yl)-phenyl]-amine was used instead of bis-biphenyl-4-yl-amine. The obtained compound was confirmed by ¹H NMR and MS/FAB.

$C_{56}H_{42}N_2$: calc. 742.33. found 742.35
¹H NMR (CDCl₃, 400 MHz) δ 8.23 (d, 1H), 8.16-8.14 (m, 1H), 7.87-7.80 (m, 3H), 7.76-7.67 (m, 6H), 7.62-7.57 (m, 5H), 7.51-7.39 (m, 5H), 7.36-7.30 (d, 2H), 7.23-7.19 (m, 2H), 6.98-6.93 (m, 2H), 6.79-6.75 (m, 3H), 1.94 (s, 6H), 1.63 (s, 6H)

17) Synthesis of Compound 29

6.25 g of Compound 29 was obtained (yield: 67%) in the same manner as in the Synthesis of Compound 1, except that bis-(9,9-diphenyl-9H-fluorene-2-yl)-amine was used instead of bis-biphenyl-4-yl-amine. The obtained compound was confirmed by ¹H NMR and MS/FAB.

$C_{47}H_{39}N$: calc. 617.31. found 617.30
¹H NMR (CDCl₃, 400 MHz) δ 7.96 (d, 2H), 7.92 (d, 1H), 7.85 (d, 1H), 7.82 (s, 3H), 7.72 (d, 1H), 7.67-7.60 (m, 3H), 7.52 (d, 1H), 7.37-7.31 (m, 4H), 7.00 (d, 1H), 6.91 (d, 2H), 6.70 (d, 2H), 1.92 (s, 6H), 1.63 (s, 12H)

18) Synthesis of Compound 34

6.10 g of Compound 34 was obtained (yield: 63%) in the same manner as in the Synthesis of Compound 1, except that dibenzofuran-2-yl-(9-phenyl-9H-carbazole-3-yl)-amine was used instead of bis-biphenyl-4-yl-amine. The obtained compound was confirmed by ¹H NMR and MS/FAB.

$C_{47}H_{32}N_2O$: calc. 640.25. found 640.23
¹H NMR (CDCl₃, 400 MHz) δ 8.22 (d, 1H), 7.92 (d, 1H), 7.85-7.82 (m, 2H), 7.75-7.72 (m, 2H), 7.68 (d, 1H), 7.66 (d, 1H), 7.63 (d, 1H), 7.57-7.49 (m, 6H), 7.46-7.37 (m, 3H), 7.35-7.25 (m, 5H), 7.07-7.03 (m, 2H), 6.97 (d, 1H), 1.93 (s, 6H)

19) Synthesis of Compound 35

7.22 g of Compound 35 was obtained (yield: 68%) in the same manner as in the Synthesis of Compound 1, except that (4-carbazole-9yl-phenyl)-[1,1';3',1"]terphenyl-5'-yl-amine was used instead of bis-biphenyl-4-yl-amine. The obtained compound was confirmed by ¹H NMR and MS/FAB.

$C_{53}H_{38}N_2$: calc. 702.30. found 702.31
¹H NMR (CDCl₃, 400 MHz) δ 8.11 (d, 2H), 7.94 (d, 1H), 7.88-7.79 (m, 6H), 7.73-7.69 (m, 2H), 7.65-7.56 (m, 5H), 7.48-7.40 (m, 8H), 7.37 (d, 1H), 7.28-7.23 (m, 2H), 7.03 (d, 2H), 6.99 (d, 1H), 6.89-6.85 (m, 2H), 1.92 (s, 6H)

20) Synthesis of Compound 36

7.13 g of Compound 36 was obtained (yield: 66%) in the same manner as in the Synthesis of Compound 1, except that bis-(4-carbazole-9-yl-phenyl)-amine was used instead of bis-biphenyl-4-yl-amine. The obtained compound was confirmed by ¹H NMR and MS/FAB.

$C_{53}H_{37}N_3$: calc. 715.30. found 715.32
¹H NMR (CDCl₃, 400 MHz) δ 8.11 (d, 4H), 7.93 (d, 1H), 7.87 (d, 1H), 7.83 (d, 1H), 7.70 (d, 1H), 7.59-7.49 (m, 13H), 7.43 (d, 1H), 7.37-7.33 (m, 4H), 6.95-6.92 (m, 5H), 1.94 (s, 6H)

21) Synthesis of Compound 37

5.31 g of Compound 37 was obtained (yield: 61%) in the same manner as in the Synthesis of Compound 1, except that 3-(4-pyrido[3,2-b]indole-5-yl-phenylamino)-benzonitrile was used instead of bis-biphenyl-4-yl-amine. The obtained compound was confirmed by ¹H NMR and MS/FAB.

$C_{41}H_{28}N_{14}$: calc. 576.23. found 576.23
¹H NMR (CDCl₃, 400 MHz) δ 8.71 (d, 1H), 8.31 (d, 1H), 7.92 (d, 1H), 7.85-7.81 (m, 2H), 7.79-7.73 (m, 2H), 7.58-7.51 (m, 3H), 7.47-7.36 (m, 8H), 7.01-6.93 (m, 3H), 6.63 (d, 1H), 1.92 (s, 6H)

22) Synthesis of Compound 41

7.07 g of Compound 41 was obtained (yield: 65%) in the same manner as in the Synthesis of Compound 1, except that N,N-di-[4-(N,N-diphenylamino)-phenyl]amine was used instead of bis-biphenyl-4-yl-amine. The obtained compound was confirmed by ¹H NMR and MS/FAB.

$C_{53}H_{41}N_3$: calc. 719.33. found 719.34
¹H NMR (CDCl₃, 400 MHz) δ 7.92 (d, 1H), 7.86 (d, 1H), 7.81 (d, 1H), 7.68 (d, 1H), 7.53 (t, 1H), 7.43 (d, 1H), 7.28-7.23 (m, 8H), 7.02 (d, 1H), 6.96-6.87 (m, 12H), 6.58-6.55 (m, 8H), 1.95 (s, 6H)

23) Synthesis of Compound 42

8.30 g of Compound 42 was obtained (yield: 62%) in the same manner as in the Synthesis of Compound 1, except that N,N-di-[4-(N,N-diphenylamino)-biphenyl]amine was used instead of bis-biphenyl-4-yl-amine. The obtained compound was confirmed by ¹H NMR and MS/FAB.

$C_{65}H_{49}N_3$: calc. 871.39. found 871.40
¹H NMR (CDCl₃, 400 MHz) δ 7.94 (d, 1H), 7.86 (d, 1H), 7.83 (d, 1H), 7.70-7.62 (m, 9H), 7.54 (t, 1H), 7.48 (d, 1H), 7.35-7.30 (m, 8H), 7.17-7.13 (m, 4H), 7.02 (d, 1H), 6.96-6.91 (m, 4H), 6.83-6.79 (m, 4H), 6.56-6.52 (m, 8H), 1.92 (s, 6H)

24) Synthesis of Compound 43

6.81 g of Compound 43 was obtained (yield: 62%) in the same manner as in the Synthesis of Compound 1, except that N4'-[1,1'-biphenyl]-4-yl-N4,N4-diphenyl-[1,1'-biphenyl]-4,4'-diamine was used instead of bis-biphenyl-4-yl-amine. The obtained compound was confirmed by ¹H NMR and MS/FAB.

$C_{53}H_{40}N_2$: calc. 704.32. found 704.33
¹H NMR (CDCl₃, 400 MHz) δ 7.93 (d, 1H), 7.87 (d, 1H), 7.86-7.82 (m, 3H), 7.75-7.71 (m, 2H), 7.70-7.60 (m, 8H), 7.55 (t, 1H), 7.48 (d, 1H), 7.37-7.32 (m, 4H), 7.06-7.02 (m, 2H), 6.93 (d, 1H), 6.89-6.85 (m, 2H), 6.81-6.73 (m, 4H), 6.62-6.58 (m, 4H), 1.95 (s, 6H)

25) Synthesis of Compound 45

7.37 g of Compound 45 was obtained (yield: 67%) in the same manner as in the Synthesis of Compound 1, except that N4,N4'-di-1-naphthalenyl-N4-phenyl]-[1,1'-biphenyl]-4,4'-diamine was used instead of bis-biphenyl-4-yl-amine. The obtained compound was confirmed by ¹H NMR and MS/FAB.

$C_{55}H_{40}N_2$: calc. 728.32. found 728.32

$^1$H NMR (CDCl$_3$, 400 MHz) δ 8.16 (d, 1H), 8.11 (d, 1H), 7.87 (d, 2H), 7.75 (d, 1H), 7.68 (d, 1H), 7.63 (d, 1H), 7.52-7.41 (m, 11H), 7.35-7.25 (m, 4H), 7.12-7.07 (m, 2H), 6.97-6.93 (m, 2H), 6.88-6.83 (m, 3H), 6.79-6.75 (t, 1H), 6.66-6.63 (m, 2H), 6.59-6.56 (m, 2H), 1.93 (s, 6H)

26) Synthesis of Compound 47

6.63 g of Compound 47 was obtained (yield: 70%) in the same manner as in the Synthesis of Compound 1, except that 4'-(9H-carbazole-9-yl)-N-phenyl-[1,1'-biphenyl]-4-amine was used instead of bis-biphenyl-4-yl-amine. The obtained compound was confirmed by $^1$H NMR and MS/FAB.

C$_{47}$H$_{34}$N$_2$: calc. 626.27. found 626.28
$^1$H NMR (CDCl$_3$, 400 MHz) δ 8.12 (d, 2H), 7.94 (d, 1H), 7.87 (d, 1H), 7.83 (d, 1H), 7.79-7.75 (m, 2H), 7.71-7.65 (m, 5H), 7.61-7.56 (m, 8H), 7.48-7.43 (m, 2H), 7.15-7.10 (m, 2H), 7.04-7.01 (m, 2H), 6.83-6.79 (m, 2H), 1.93 (s, 6H)

27) Synthesis of Compound 48

7.48 g of Compound 48 was obtained (yield: 69%) in the same manner as in the Synthesis of Compound 1, except that N,N,N',N'-tetraphenyl-9H-carbazole-3,6-diamine was used instead of bis-biphenyl-4-yl-amine.

The obtained compound was confirmed by $^1$H NMR and MS/FAB. C$_{53}$H$_{39}$N$_3$: calc. 717.31. found 717.32
$^1$H NMR (CDCl$_3$, 400 MHz) δ 8.17 (d, 1H), 7.95 (d, 1H), 7.88 (d, 1H), 7.79 (d, 1H), 7.68 (d, 2H), 7.56-7.52 (m, 3H), 7.41 (d, 1H), 7.25-7.19 (m, 9H), 6.88-6.82 (m, 6H), 6.63-6.60 (m, 8H), 1.95 (s, 6H)

28) Synthesis of Compound 49

5.40 g of Compound 49 was obtained (yield: 60%) in the same manner as in the Synthesis of Compound 6, except that B-(4,6-diphenyl-1,3,5-triazine-2-yl)-boronic acid was used instead of phenylboronic acid, and diphenyl-amine was used instead of biphenyl-4-yl-(9,9-dimethyl-9H-fluorene-2-yl)-amine. The obtained compound was confirmed by $^1$H NMR and MS/FAB.

C$_{44}$H$_{32}$N$_4$: calc. 616.26. found 616.27
$^1$H NMR (CDCl$_3$, 400 MHz) δ 9.22 (s, 1H), 8.80-8.77 (m, 5H), 7.83 (d, 1H), 7.65 (t, 4H), 7.56-7.52 (m, 4H), 7.29-7.25 (m, 4H), 7.01-6.95 (m, 3H), 6.62-6.58 (m, 4H), 1.94 (s, 6H)

29) Synthesis of Compound 50

4.72 g of Compound 50 was obtained (yield: 63%) in the same manner as in the Synthesis of Compound 6, except that 3-pyridylboronic acid was used instead of phenylboronic acid, and naphthalene-1-yl-phenyl-amine was used instead of biphenyl-4-yl-(9,9-dimethyl-9H-fluorene-2-yl)-amine. The obtained compound was confirmed by $^1$H NMR and MS/FAB.

C$_{38}$H$_{28}$N$_2$: calc. 512.23. found 512.25
$^1$H NMR (CDCl$_3$, 400 MHz) δ 9.03 (d, 1H), 8.69-8.67 (m, 1H), 8.11 (d, 1H), 8.06 (d, 2H), 7.86 (d, 1H), 7.50-7.39 (m, 6H), 7.37-7.34 (m, 3H), 7.15-7.11 (m, 2H), 6.91 (d, 1H), 6.89-6.86 (m, 2H), 6.53-6.50 (m, 2H), 1.93 (s, 6H)

Example 1

To prepare an anode, a 15 Ω/cm$^2$ (1200 Å) Corning ITO glass substrate was cut to a size of 50 mm×50 mm×0.7 mm, washed with ultrasonic waves in isopropyl alcohol and pure water for 5 minutes each, and then cleaned with UV and ozone for 30 minutes. The ITO glass substrate was mounted on a vacuum depositor.

2-TNATA was vacuum deposited on the ITO glass substrate to form a HIL having a thickness of 600 Å, and Compound 6 was vacuum deposited on the HIL to form a HTL having a thickness of 300 Å.

Next, 9,10-di-naphthalene-2-yl-anthracene (DNA) as a blue fluorescent host and 4,4'-bis[2-(4-(N,N-diphenylamino)phenyl)vinyl)biphenyl (DPAVBi) as a blue fluorescent dopant were co-deposited on the HTL at a weight ratio of 98:2 to form an EML having a thickness of 300 Å.

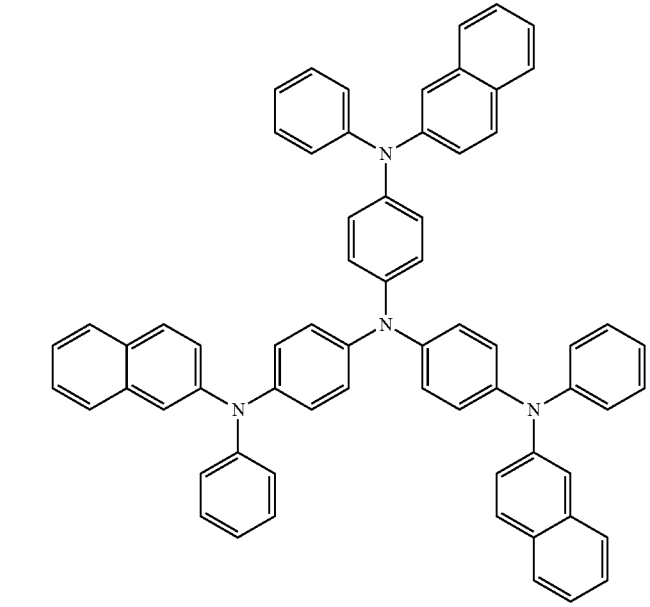

2-TNATA

-continued

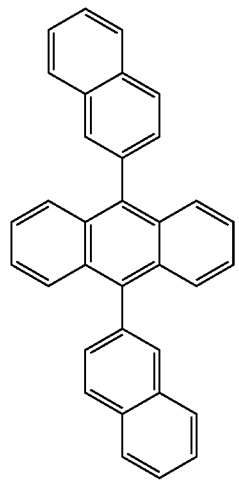

DNA

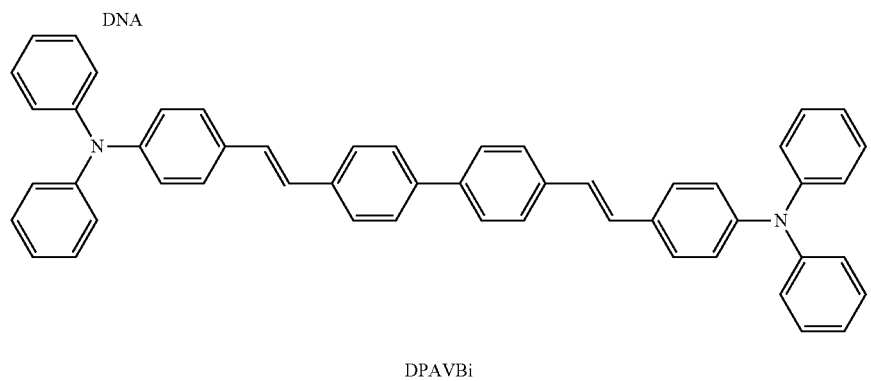

DPAVBi

Subsequently, Alq$_3$ was deposited on the EML to form an ETL having a thickness of 300 Å, LiF was deposited on the ETL to form an EIL having a thickness of 10 Å, and Al was deposited on the EIL to form a LiF/Al electrode (cathode) having a thickness of 3,000 Å, thereby completing the manufacture of an OLED.

The OLED had a driving voltage of 5.63 V at a current density of 50 mA/cm$^2$, a brightness of 2760 cd/m$^2$, a luminous efficiency of 5.52 cd/A, and a half-lifetime (hr @100 mA/cm$^2$) of 324 hours.

Example 2

An OLED was manufactured in the same manner as in Example 1, except that Compound 17 was used instead of Compound 6.

The OLED had a driving voltage of 5.67 V at a current density of 50 mA/cm$^2$, a brightness of 2745 cd/m$^2$, a luminous efficiency of 5.49 cd/A, and a half-lifetime (hr @100 mA/cm$^2$) of 293 hours.

Example 3

An OLED was manufactured in the same manner as in Example 1, except that Compound 21 was used instead of Compound 6.

The OLED had a driving voltage of 5.79 V at a current density of 50 mA/cm$^2$, a brightness of 2770 cd/cm$^2$, a luminous efficiency of 5.54 cd/A, and a half-lifetime (hr @100 mA/cm$^2$) of 307 hours.

Example 4

An OLED was manufactured in the same manner as in Example 1, except that Compound 26 was used instead of Compound 6.

The OLED had a driving voltage of 5.58 V at a current density of 50 mA/cm$^2$, a brightness of 2560 cd/cm$^2$, a luminous efficiency of 5.12 cd/A, and a half-lifetime (hr @100 mA/cm$^2$) of 297 hours.

Example 5

An OLED was manufactured in the same manner as in Example 1, except that Compound 35 was used instead of Compound 6.

The OLED had a driving voltage of 5.82 V at a current density of 50 mA/cm$^2$, a brightness of 2780 cd/cm$^2$, a luminous efficiency of 5.56 cd/A, and a half-lifetime (hr @100 mA/cm$^2$) of 317 hours.

Example 6

An OLED was manufactured in the same manner as in Example 1, except that Compound 41 was used instead of Compound 6.

The OLED had a driving voltage of 5.56 V at a current density of 50 mA/cm$^2$, a brightness of 2805 cd/cm$^2$, a luminous efficiency of 5.61 cd/A, and a half-lifetime (hr @100 mA/cm$^2$) of 268 hours.

Example 7

An OLED was manufactured in the same manner as in Example 1, except that Compound 45 was used instead of Compound 6.

The OLED had a driving voltage of 5.43 V at a current density of 50 mA/cm², a brightness of 2835 cd/cm², a luminous efficiency of 5.67 cd/A, and a half-lifetime (hr @100 mA/cm²) of 356 hours.

Example 8

An OLED was manufactured in the same manner as in Example 1, except that Compound 48 was used instead of Compound 6.

The OLED had a driving voltage of 5.62 V at a current density of 50 mA/cm², a brightness of 2670 cd/cm², a luminous efficiency of 5.34 cd/A, and a half-lifetime (hr @100 mA/cm²) of 322 hours.

Example 9

An OLED was manufactured in the same manner as in Example 1, except that Compound 49 was used instead of Compound 6.

The OLED had a driving voltage of 5.37 V at a current density of 50 mA/cm², a brightness of 2575 cd/cm², a luminous efficiency of 5.15 cd/A, and a half-lifetime (hr @100 mA/cm²) of 215 hours.

Comparative Example 1

An OLED was manufactured in the same manner as in Example 1, except that 4,4'-bis[N-(1-naphthyl)-N-phenylamino]biphenyl (NPB) was used instead of Compound 6.

The OLED had a driving voltage of 7.35 V at a current density of 50 mA/cm², a brightness of 2065 cd/cm², a luminous efficiency of 4.13 cd/A, and a half-lifetime (hr @100 mA/cm²) of 145 hours.

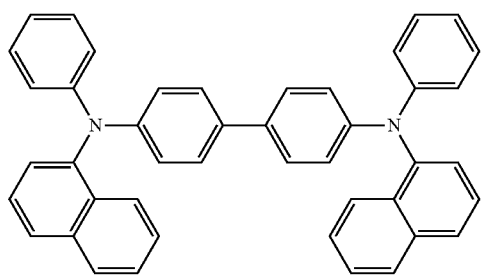

NPB

Comparative Example 2

An OLED was manufactured in the same manner as in Example 1, except that Compound 52 (below) was used instead of Compound 6 in the formation of the HTL.

The OLED had a driving voltage of 6.87 V at a current density of 50 mA/cm², a brightness of 2,340 cd/cm², a luminous efficiency of 4.68 cd/A, and a half-lifetime (hr @100 mA/cm²) of 220 hours.

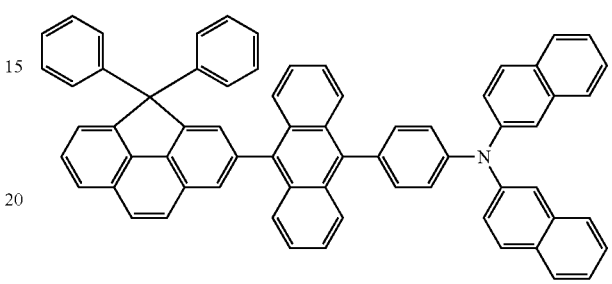

52

Comparative Example 3

An OLED was manufactured in the same manner as in Example 1, except that Compound 53 (below) was used instead of Compound 6 in the formation of the HTL.

The OLED had a driving voltage of 7.12 V at a current density of 50 mA/cm², a brightness of 2,105 cd/cm², a luminous efficiency of 4.21 cd/A, and a half-lifetime (hr @100 mA/cm²) of 132 hours.

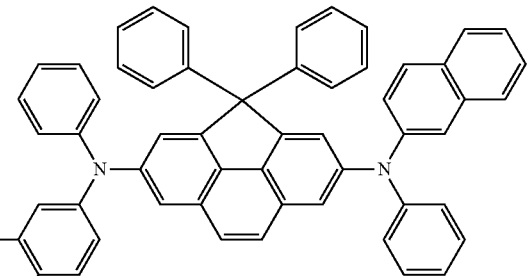

53

The characteristics and lifetimes of the OLEDs of Examples 1 to 9 and Comparative Examples 1 to 3 are shown in Table 1 below.

TABLE 1

| | Hole transporting material | Driving voltage (V) | Current density (mA/cm²) | brightness (cd/m²) | efficiency (cd/A) | Emission color | Half-lifetime (hr @ 100 mA/cm²) |
|---|---|---|---|---|---|---|---|
| Example 1 | Compound 6  | 5.63 | 50 | 2,760 | 5.52 | blue | 324 hr |
| Example 2 | Compound 17 | 5.67 | 50 | 2,745 | 5.49 | blue | 293 hr |
| Example 3 | Compound 21 | 5.79 | 50 | 2,770 | 5.54 | blue | 307 hr |
| Example 4 | Compound 26 | 5.58 | 50 | 2,560 | 5.12 | blue | 297 hr |
| Example 5 | Compound 35 | 5.82 | 50 | 2,780 | 5.56 | blue | 317 hr |
| Example 6 | Compound 41 | 5.56 | 50 | 2,805 | 5.61 | blue | 268 hr |
| Example 7 | Compound 45 | 5.43 | 50 | 2,835 | 5.67 | blue | 356 hr |
| Example 8 | Compound 48 | 5.62 | 50 | 2,670 | 5.34 | blue | 322 hr |

TABLE 1-continued

|  | Hole transporting material | Driving voltage (V) | Current density (mA/cm$^2$) | brightness (cd/m$^2$) | efficiency (cd/A) | Emission color | Half-lifetime (hr @ 100 mA/cm$^2$) |
|---|---|---|---|---|---|---|---|
| Example 9 | Compound 49 | 5.37 | 50 | 2,575 | 5.15 | blue | 215 hr |
| Comp. Example 1 | NPB | 7.35 | 50 | 2,065 | 4.13 | blue | 145 hr |
| Comp. Example 2 | Compound 52 | 6.87 | 50 | 2,340 | 4.68 | blue | 220 hr |
| Comp. Example 3 | Compound 53 | 7.12 | 50 | 2,105 | 4.21 | blue | 132 hr |

From the results shown in Table 1, it was confirmed that when the compound of Formula 1 was used as a hole transporting material, the OLED including the compound of Formula 1 exhibited good current-voltage-luminance (I-V-L) characteristics, i.e., a significantly improved driving voltage and high efficiency, and in particular, exhibited a significantly improved lifetime, as compared to the OLED including NPB.

As described above, according to the one or more embodiments of the present invention, novel compounds represented by Formula 1 have good luminous properties and charge transporting abilities, and thus, may be suitable for use as hole injection materials or hole transporting materials in fluorescent and phosphorescent devices of all colors, such as red, green, blue, white, and the like. Thus, OLEDs including the compounds of Formula 1 may have high efficiency, low voltage, high brightness, and long lifetimes.

While the present invention has been illustrated and described with reference to certain exemplary embodiments, it will be understood by those of ordinary skill in the art that various changes may be made to the described embodiments without departing from the spirit and scope of the present invention as defined by the following claims.

What is claimed is:

1. A compound for an organic light-emitting diode represented by Formula 1:

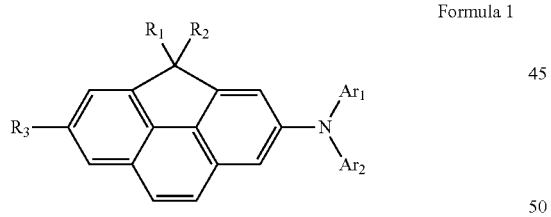

Formula 1 wherein the compound is asymmetric and:
$R_1$ and $R_2$ are each independently a halogen, a cyano group, a substituted or unsubstituted $C_1$-$C_{60}$ alkyl group, a substituted or unsubstituted $C_6$-$C_{60}$ aryl group, a substituted or unsubstituted $C_3$-$C_{60}$ heteroaryl group, or a substituted or unsubstituted $C_6$-$C_{60}$ condensed polycyclic group, or $R_1$ and $R_2$ optionally combine to form a ring;
$R_3$ is:
hydrogen,
deuterium,
a halogen,
a cyano group,
an unsubstituted $C_6$-$C_{60}$ aryl group,
a substituted or unsubstituted $C_3$-$C_{60}$ heteroaryl group selected from the group consisting of pyrazolyl groups, imidazolyl groups, oxazolyl groups, thiazolyl groups, triazolyl groups, tetrazolyl groups, oxadiazolyl groups, pyridinyl groups, pyridazinyl groups, pyrimidinyl groups, triazinyl groups, indolyl groups, quinolinyl groups, isoquinolinyl groups, and dibenzothiophene groups,
a substituted or unsubstituted $C_6$-$C_{60}$ condensed polycyclic group, or
a $C_6$-$C_{60}$ aryl group substituted with a substituent selected from the group consisting of deuterium, a halogen atom, a hydroxyl group, a nitro group, a cyano group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, and a $C_4$-$C_{16}$ heteroaryl group;
$Ar_1$ and $Ar_2$ are each independently a moiety represented by any one of Formulae 4a through 4g:

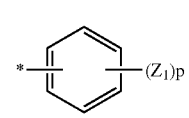

4a

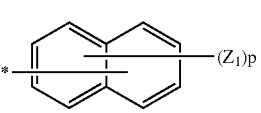

4b

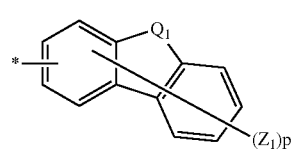

4c

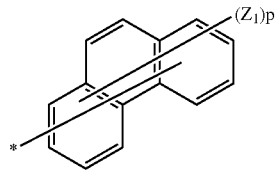

4d

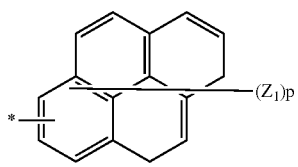

4e

-continued

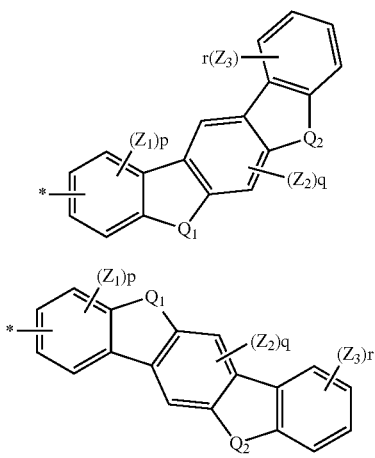

4f

4g wherein:
Q₁ and Q₂ are each independently a linking group represented by —C(R₃₀)(R₃₁)—, —N(R₃₂)—, —S—, or —O—;
$Z_1, Z_2, Z_3, R_{30}, R_{31}$ and $R_{32}$ are each independently a hydrogen atom, deuterium, a substituted or unsubstituted $C_1$-$C_{20}$ alkyl group, an unsubstituted $C_6$-$C_{20}$ aryl group, a substituted or unsubstituted $C_6$-$C_{20}$ condensed polycyclic group, a halogen, a cyano group, a nitro group, a hydroxyl group, or a carboxyl group;
p is an integer of 1 to 9;
q is 1 or 2;
r is an integer of 1 to 4; and
* denotes a binding site.

2. The compound of claim 1, wherein $R_1$ and $R_2$ are each independently a halogen, a cyano group, a substituted or unsubstituted $C_1$-$C_{30}$ alkyl group, a substituted or unsubstituted $C_6$-$C_{30}$ aryl group, a substituted or unsubstituted $C_3$-$C_{30}$ heteroaryl group, or a substituted or unsubstituted $C_6$-$C_{30}$ condensed polycyclic group;
$R_3$ is:
 hydrogen,
 deuterium,
 a halogen,
 a cyano group,
 an unsubstituted $C_6$-$C_{30}$ aryl group,
 a substituted or unsubstituted $C_3$-$C_{30}$ heteroaryl group selected from the group consisting of pyrazolyl groups, imidazolyl groups, oxazolyl groups, thiazolyl groups, triazolyl groups, tetrazolyl groups, oxadiazolyl groups, pyridinyl groups, pyridazinyl groups, pyrimidinyl groups, triazinyl groups, indolyl groups, quinolinyl groups, isoquinolinyl groups, and dibenzothiophene groups,
 a substituted or unsubstituted $C_6$-$C_{30}$ condensed polycyclic group, or
 a $C_6$-$C_{60}$ aryl group substituted with a substituent selected from the group consisting of deuterium, a halogen atom, a hydroxyl group, a nitro group, a cyano group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, and a $C_4$-$C_{16}$ heteroaryl group.

3. The compound of claim 1, wherein $R_1$ and $R_2$ are each independently hydrogen, deuterium, a halogen, a cyano group, a substituted or unsubstituted $C_1$-$C_{20}$ alkyl group, or a moiety represented by any one of Formulae 2a through 2c:

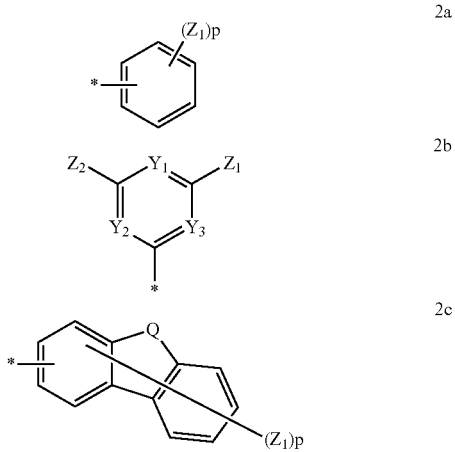

wherein:
$Y_1, Y_2$, and $Y_3$ are each independently a linking group represented by —N═, —N(R₂₀)—, or —C(R₂₁)═;
Q is a linking group represented by —C(R₃₀)(R₃₁)—, —N(R₃₂)—, —S—, or —O—;
$Z_1, Z_2, R_{20}, R_{21}, R_{30}, R_{31}$, and $R_{32}$ are each independently a hydrogen atom, deuterium, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, an amino group substituted with a $C_6$-$C_{20}$ aryl group or a $C_3$-$C_{20}$ heteroaryl group, a halogen group, a cyano group, a nitro group, a hydroxyl group, or a carboxyl group;
p is an integer of 1 to 7; and
* denotes a binding site.

4. The compound of claim 1, wherein $R_3$ is hydrogen, deuterium, a halogen, or a moiety represented by at least one of Formulae 3a through 3c:

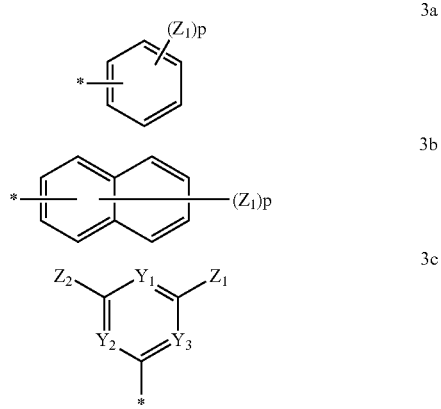

wherein:
$Y_2$, and $Y_3$ are each independently a linking group represented by —N═, —N(R₂₀)—, or —C(R₂₁)═;
$Z_1, Z_2, R_{20}$, and $R_{21}$ are each independently a hydrogen atom, deuterium, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, a halogen, a cyano group, a nitro group, a hydroxyl group, or a carboxyl group;

p is an integer of 1 to 7; and

* denotes a binding site.

5. The compound of claim 1, wherein $R_1$ and $R_2$ combine to form a ring.

6. A compound for an organic light-emitting diode, wherein the compound is selected from Compounds 1 through 40 and 48 through 50:

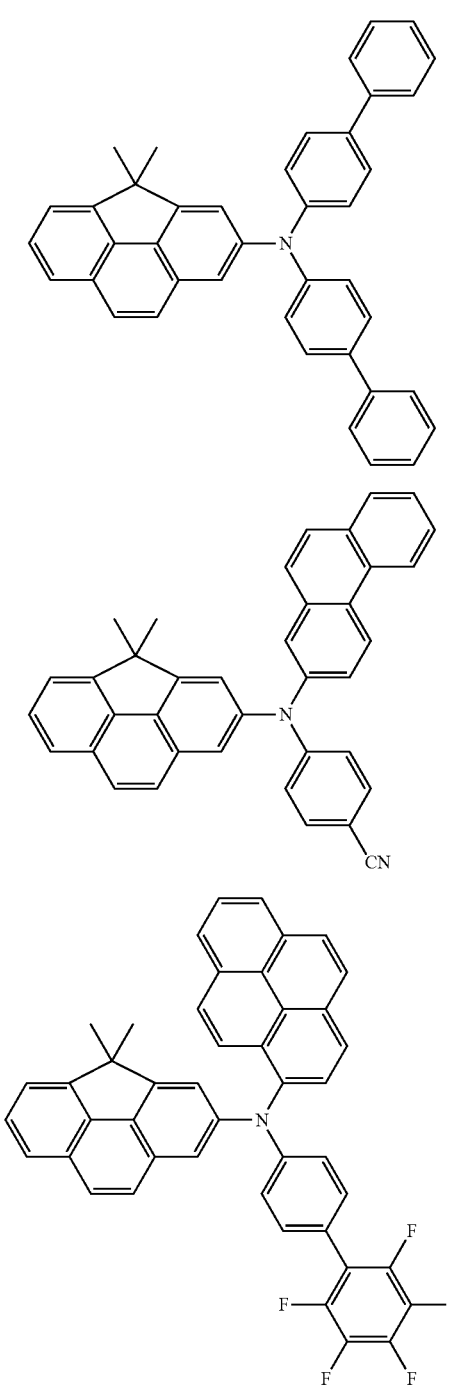

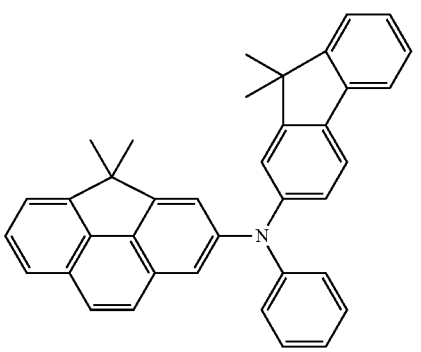

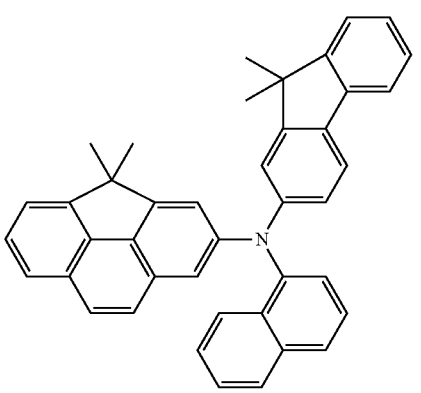

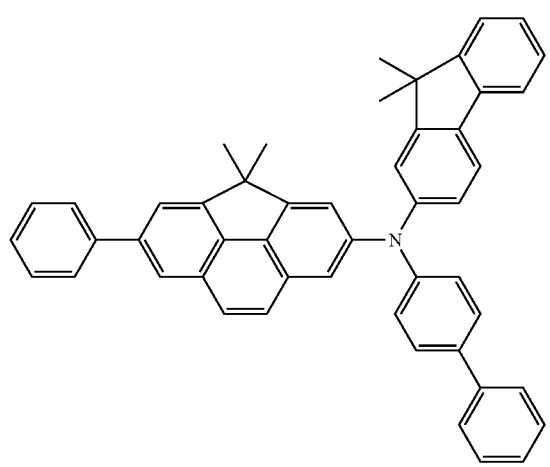

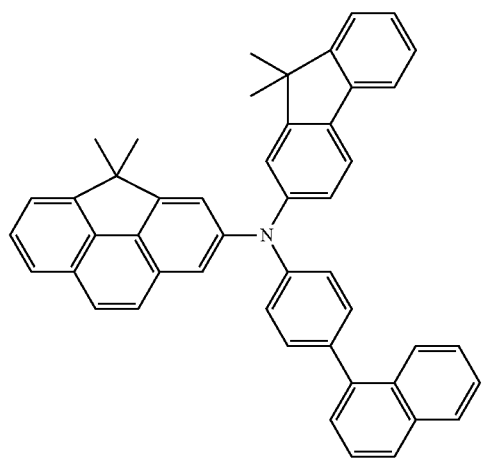
7
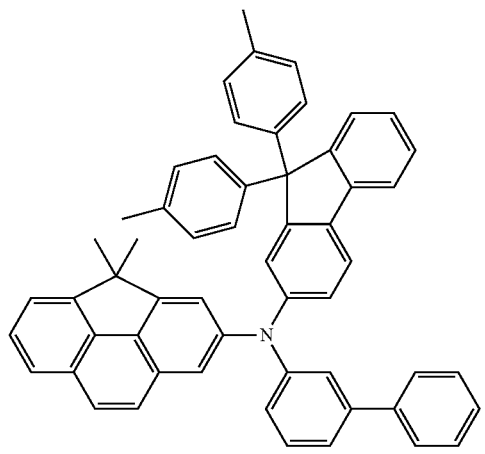
11
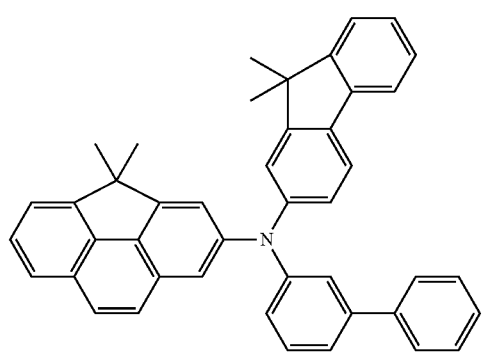
8
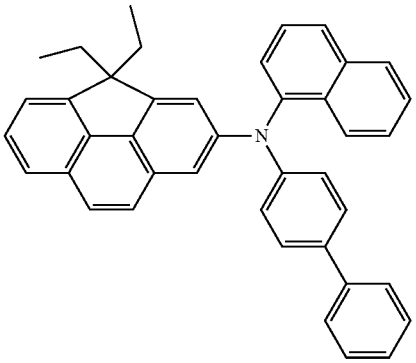
12
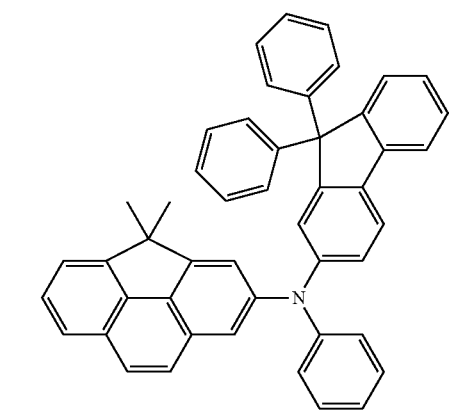
9
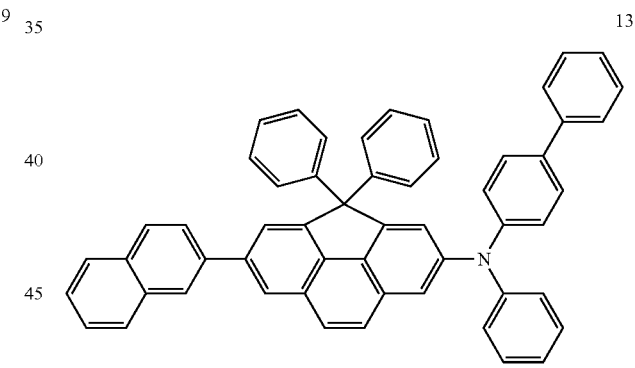
13
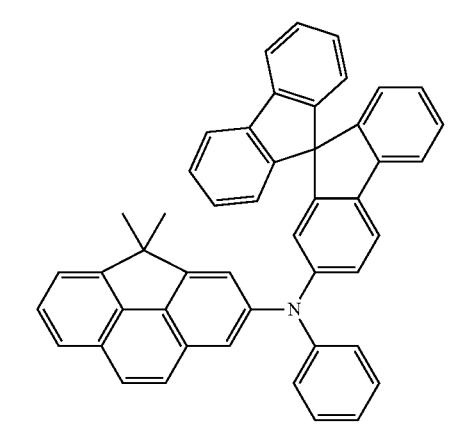
10
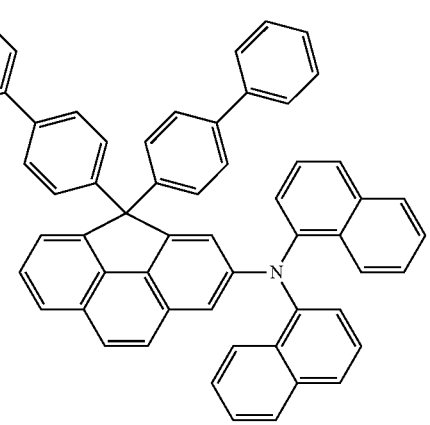
14

15
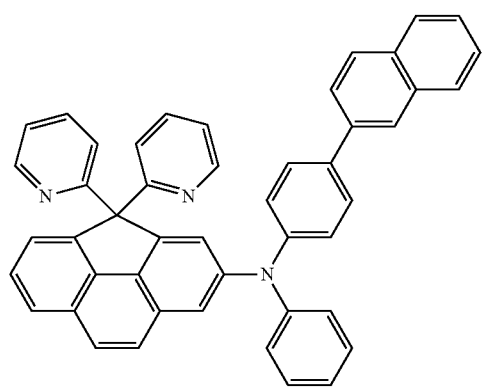
16
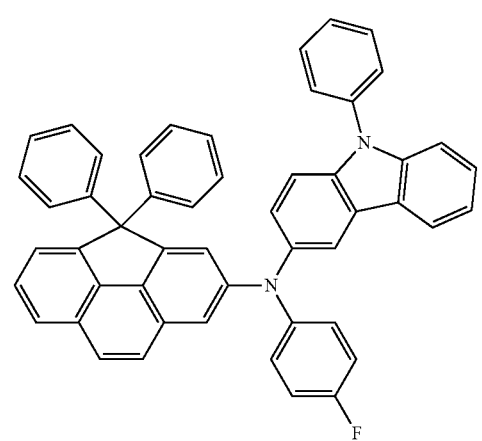
17
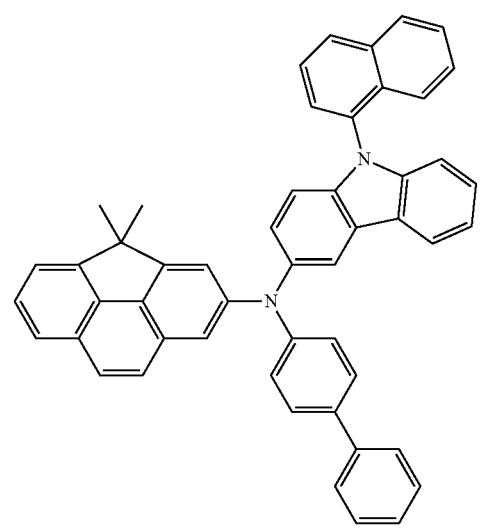
18
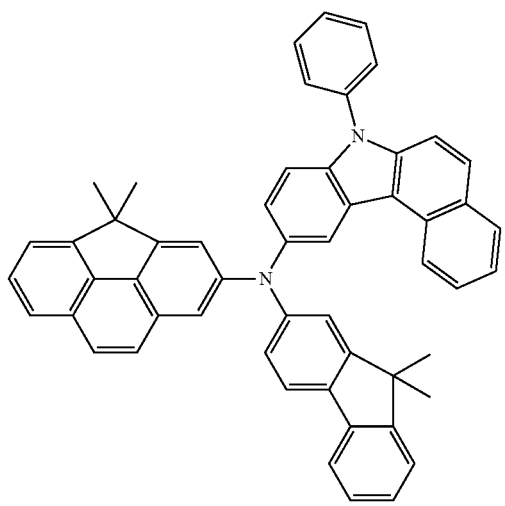
19
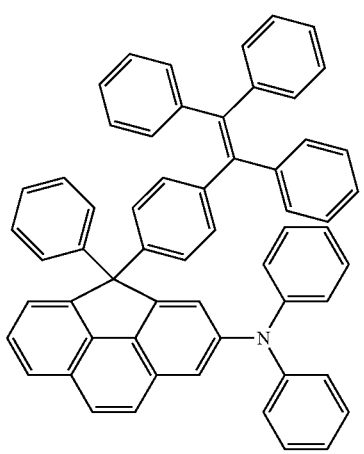
20
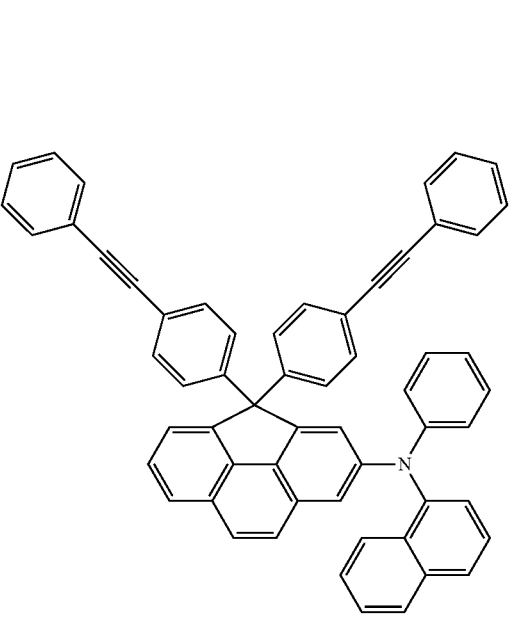

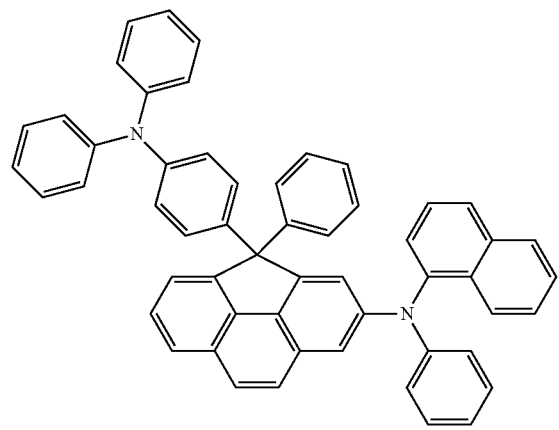
21
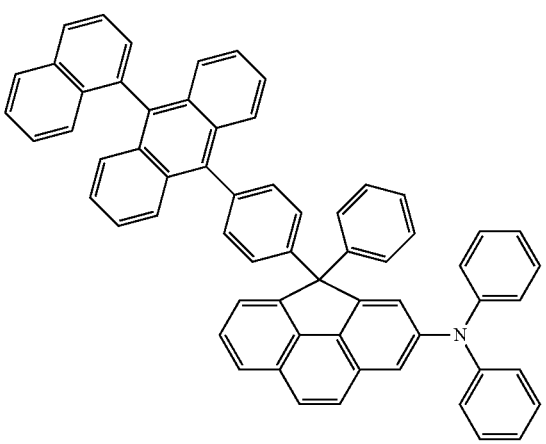
24
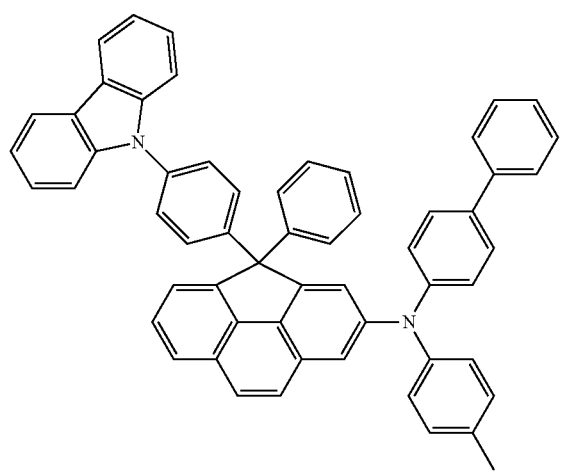
22
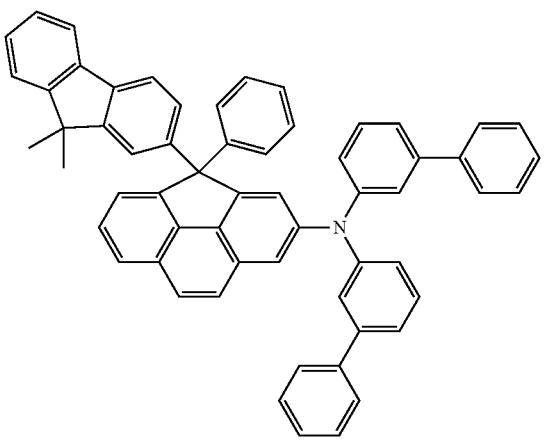
25
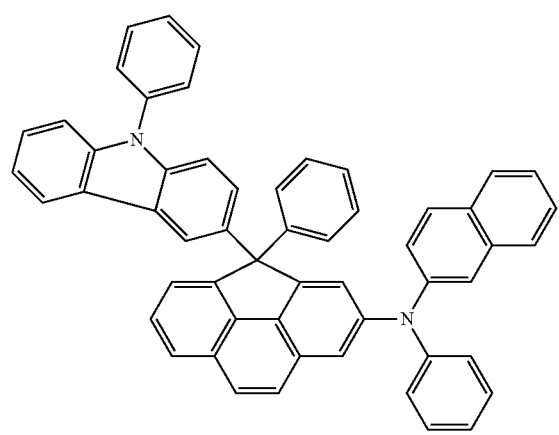
23
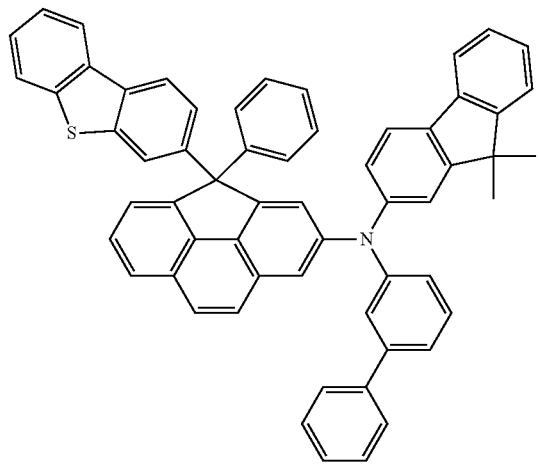
26

-continued
27
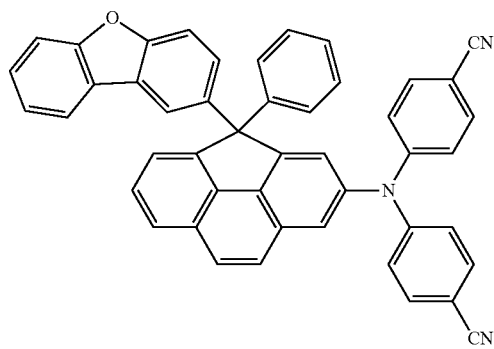
28
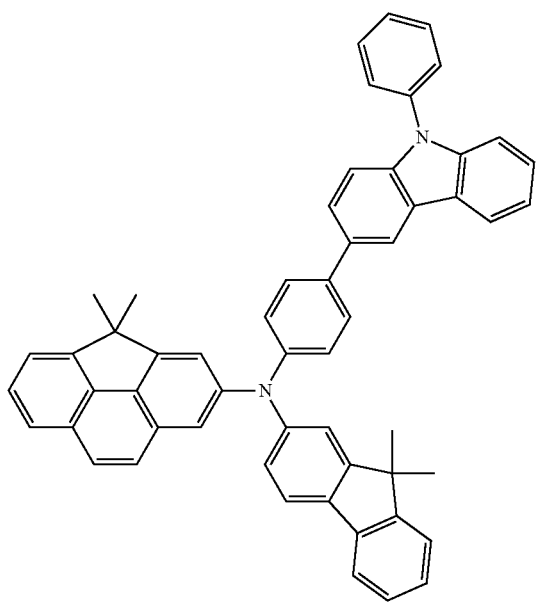
29
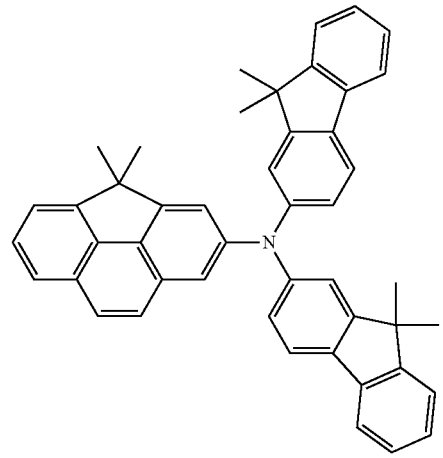
-continued
30
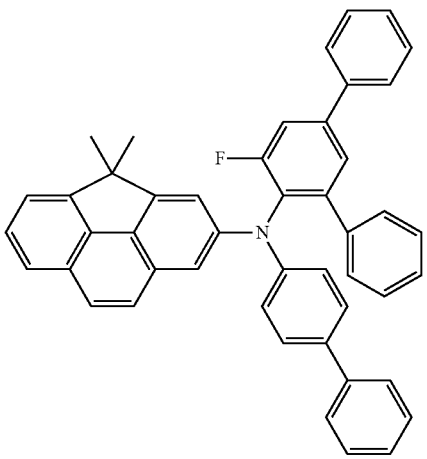
31
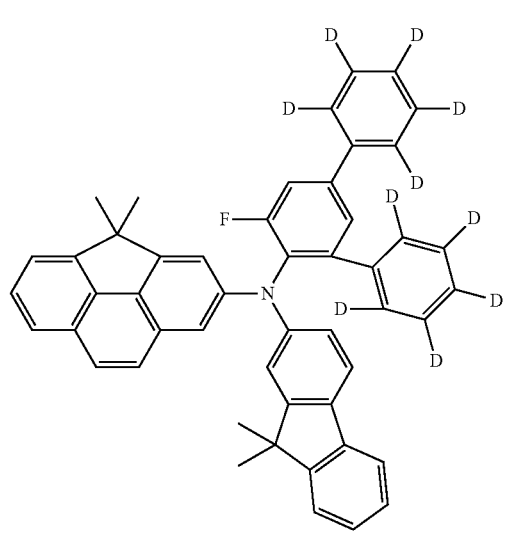
32
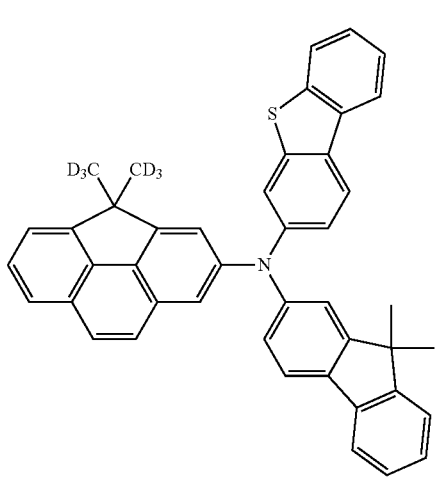

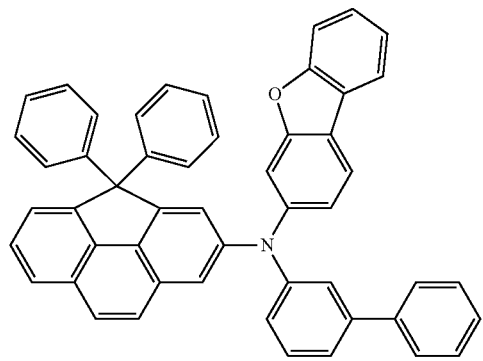
33
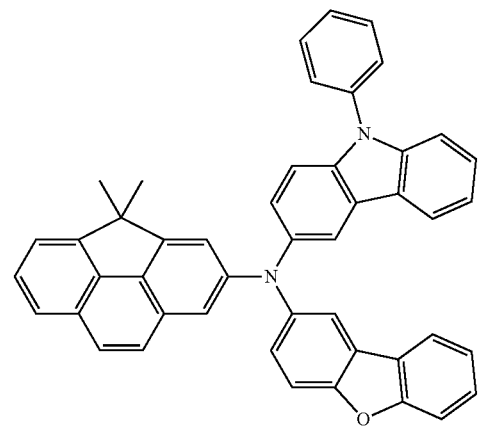
34
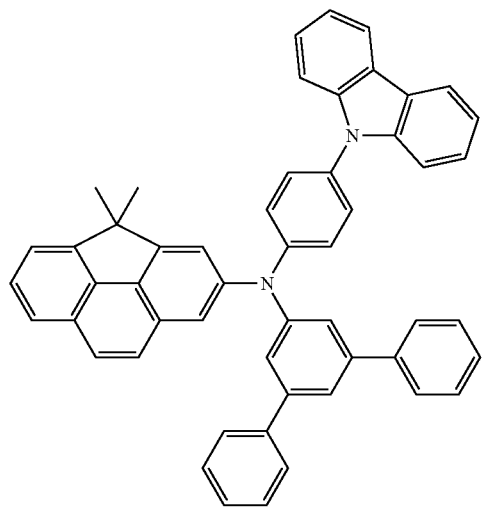
35
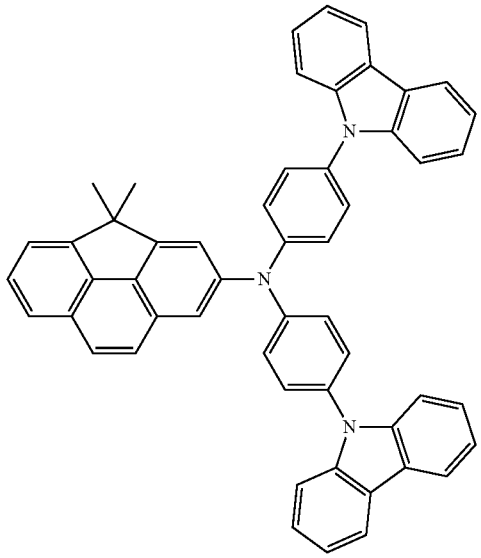
36
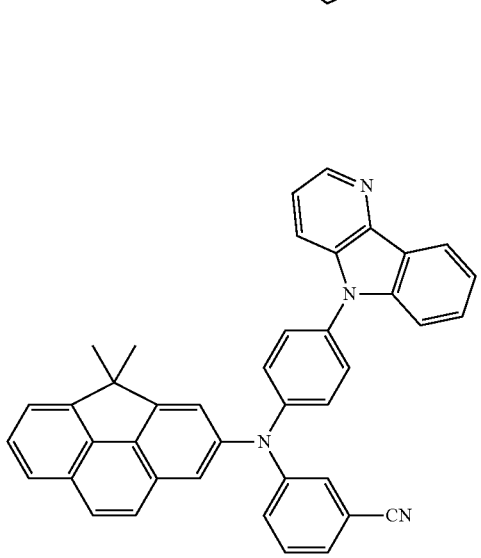
37
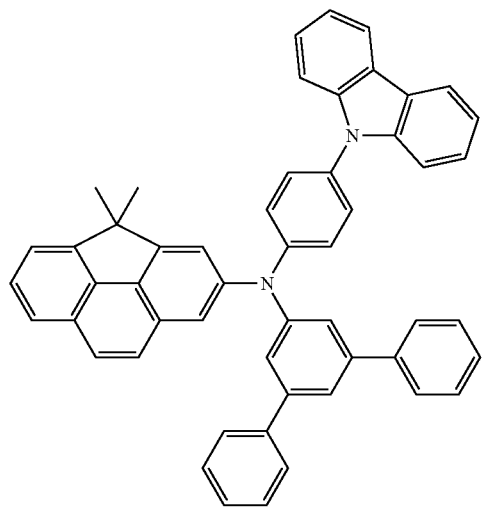
38

39

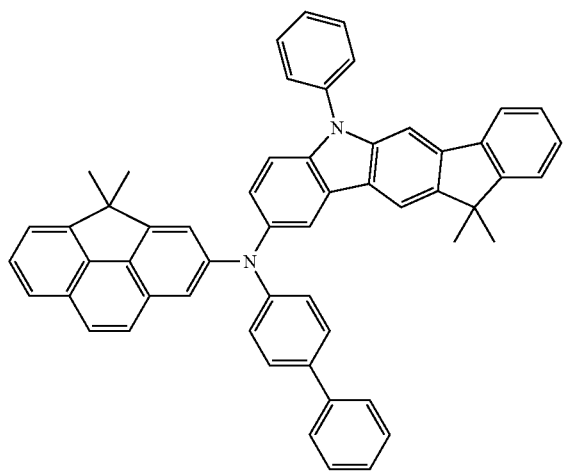

40

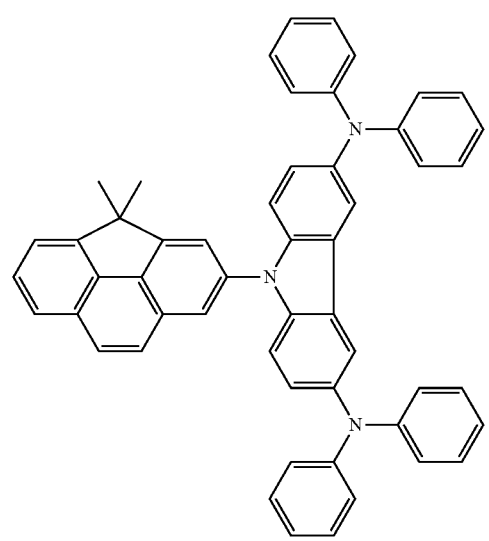

49

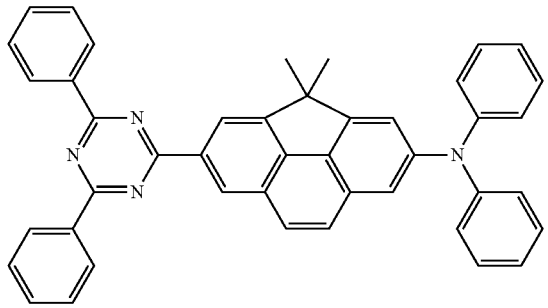

50

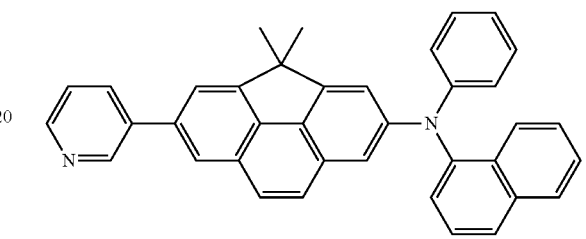

51

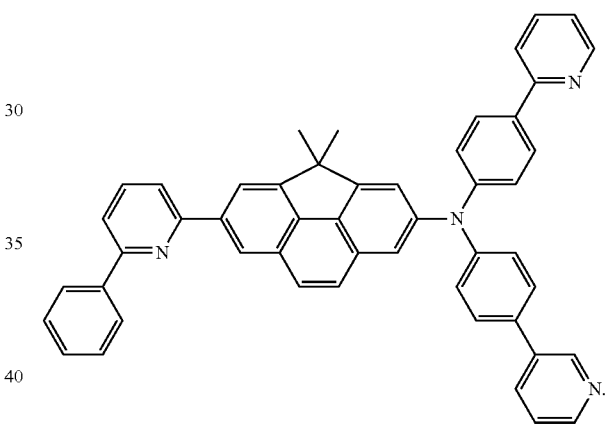

7. An organic light-emitting diode comprising:
a first electrode;
a second electrode; and
an organic layer between the first electrode and the second electrode, the organic layer comprising the compound according to claim 1.

8. The organic light-emitting diode of claim 7, wherein the organic layer is an emission layer, and the compound represented by Formula 1 is a fluorescent host or a phosphorescent host.

9. The organic light-emitting diode of claim 7, wherein the organic layer is an emission layer, and the compound represented by Formula 1 is a fluorescent dopant.

10. The organic light-emitting diode of claim 7, wherein the organic layer is a hole injection layer, a hole transport layer, or a functional layer having hole injection and hole transport abilities.

11. The organic light-emitting diode of claim 7, wherein the organic layer is a hole transport layer.

12. The organic light-emitting diode of claim 7, wherein the organic light-emitting diode comprises an emission layer, a hole injection layer, a hole transport layer, or a functional layer having hole injection and hole transport abilities, wherein the emission layer, the hole injection layer, the hole transport layer, or the functional layer having hole injection and hole transport abilities comprises the compound according to claim 1, and the emission layer comprises an anthracene-based compound, an arylamine-based compound, or a styryl-based compound.

13. The organic light-emitting diode of claim 7, wherein the organic light-emitting diode comprises an emission layer, a hole injection layer, a hole transport layer, or a functional layer having hole injection and hole transport abilities, wherein the hole injection layer, the hole transport layer, or the functional layer having hole injection and hole transport abilities comprises the compound according to claim 1, and any one of a red layer, a green layer, a blue layer, or a white layer of the emission layer comprises a phosphorescent compound.

14. The organic light-emitting diode of claim 13, wherein the hole injection layer, the hole transport layer, or the functional layer having hole injection and hole transport abilities comprises a charge-generating material.

15. The organic light-emitting diode of claim 14, wherein the charge-generating material is a p-dopant, wherein the p-dopant is a quinone derivative, a metal oxide, or a cyano-containing compound.

16. The organic light-emitting diode of claim 7, wherein the organic layer comprises an electron transport layer, wherein the electron transport layer comprises an electron transporting organic compound and a metal complex.

17. The organic light-emitting diode of claim 7, wherein the organic layer is formed using the compound according to claim 1 using a wet process.

18. A flat panel display device comprising the organic light-emitting diode of claim 7, wherein the first electrode of the organic light-emitting diode is electrically connected to a source electrode or a drain electrode of a thin film transistor.

* * * * *